United States Patent
Stulen et al.

(10) Patent No.: US 10,231,747 B2
(45) Date of Patent: Mar. 19, 2019

(54) TRANSDUCER FEATURES FOR ULTRASONIC SURGICAL INSTRUMENT

(71) Applicant: Ethicon Endo-Surgery, Inc., Cincinnati, OH (US)

(72) Inventors: Foster B. Stulen, Mason, OH (US); Michael R. Lamping, Cincinnati, OH (US); Scott A. Nield, Hamilton, OH (US); Timothy G. Dietz, Wayne, PA (US); John B. Schulte, West Chester, OH (US); Sora Rhee, Cincinnati, OH (US); Jacob S. Gee, Cincinnati, OH (US); Stephen J. Balek, Springboro, OH (US); William D. Dannaher, Cincinnati, OH (US); Gavin M. Monson, Oxford, OH (US)

(73) Assignee: Ethicon LLC, Guaynabo, PR (US)

( * ) Notice: Subject to any disclaimer, the term of this patent is extended or adjusted under 35 U.S.C. 154(b) by 1377 days.

(21) Appl. No.: 14/032,842

(22) Filed: Sep. 20, 2013

(65) Prior Publication Data
US 2015/0088178 A1    Mar. 26, 2015

(51) Int. Cl.
*A61B 17/32* (2006.01)
*H01L 41/047* (2006.01)
(Continued)

(52) U.S. Cl.
CPC ........ *A61B 17/320068* (2013.01); *A61N 7/02* (2013.01); *H01L 41/0475* (2013.01);
(Continued)

(58) Field of Classification Search
CPC ...... A61B 17/320068; A61B 17/22004; A61B 17/2202; A61B 2017/22027; A61B 2017/22014
(Continued)

(56) References Cited

U.S. PATENT DOCUMENTS

| 4,065,687 A | 12/1977 | Mishiro |
| 5,152,695 A * | 10/1992 | Grabbe ............... H01R 13/245 |
| | | 439/66 |

(Continued)

FOREIGN PATENT DOCUMENTS

| CN | 1684635 A | 10/2005 |
| CN | 101772327 A | 7/2010 |

(Continued)

OTHER PUBLICATIONS

U.S. Appl. No. 13/538,588, filed Jun. 29, 2012.
(Continued)

*Primary Examiner* — Diane Yabut
*Assistant Examiner* — Majid Jamialahmadi
(74) *Attorney, Agent, or Firm* — Frost Brown Todd LLC

(57) ABSTRACT

An apparatus for operating on tissue includes a body, a shaft, an ultrasonic blade, and an acoustic assembly. The shaft extends distally from the body. The blade is disposed at the distal end of the shaft. The acoustic assembly comprises an acoustic waveguide coupled with the blade, a piezoelectric transducer element, a fastener, and a coupling member. The transducer element defines an inner diameter surface and an outer diameter surface. The fastener is configured to secure the transducer element relative to the waveguide. The coupling member is configured to provide electrical continuity between the fastener and the inner diameter surface of the transducer element. The outer diameter surface of the transducer element includes an annular recess. Another coupling member is configured to provide electrical continuity between the annular recess of the piezoelectric transducer element and a power source while permitting the piezoelectric transducer element to rotate relative to the body.

20 Claims, 64 Drawing Sheets

(51) Int. Cl.
  *A61N 7/02* (2006.01)
  *A61B 17/22* (2006.01)
  *A61B 17/00* (2006.01)

(52) U.S. Cl.
  CPC .............. *A61B 17/320092* (2013.01); *A61B 2017/00477* (2013.01); *A61B 2017/22027* (2013.01)

(58) Field of Classification Search
  USPC .......................................... 606/169; 600/459
  See application file for complete search history.

(56) References Cited

U.S. PATENT DOCUMENTS

| | | | |
|---|---|---|---|
| 5,322,055 A | 6/1994 | Davison et al. | |
| 5,873,873 A | 2/1999 | Smith et al. | |
| 5,980,510 A | 11/1999 | Tsonton et al. | |
| 6,024,718 A * | 2/2000 | Chen ................. | A61B 17/2202 604/22 |
| 6,325,811 B1 | 12/2001 | Messerly | |
| 6,773,444 B2 | 8/2004 | Messerly | |
| 6,783,524 B2 | 8/2004 | Anderson et al. | |
| 6,809,508 B2 | 10/2004 | Donofrio | |
| 8,461,744 B2 | 6/2013 | Wiener et al. | |
| 2005/0049712 A1* | 3/2005 | Ondrla ................. | A61F 2/4059 623/22.12 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2009/0105750 A1 | 4/2009 | Price et al. | |
| 2010/0069940 A1 | 3/2010 | Miller et al. | |
| 2011/0087212 A1 | 4/2011 | Aldridge et al. | |
| 2011/0196400 A1* | 8/2011 | Robertson ........ | A61B 17/22004 606/169 |
| 2012/0029546 A1 | 2/2012 | Robertson | |
| 2012/0112687 A1 | 5/2012 | Houser et al. | |
| 2012/0116261 A1 | 5/2012 | Mumaw et al. | |
| 2012/0116265 A1 | 5/2012 | Houser et al. | |
| 2012/0116389 A1 | 5/2012 | Houser et al. | |
| 2013/0197550 A1 | 8/2013 | Dietz et al. | |
| 2014/0081299 A1* | 3/2014 | Dietz ............. | A61B 17/320068 606/169 |

FOREIGN PATENT DOCUMENTS

| | | |
|---|---|---|
| CN | 103027720 A | 4/2013 |
| JP | H06-217989 A | 8/1994 |
| JP | 2002-248111 A | 9/2002 |
| JP | 2004-503324 A | 2/2004 |
| JP | 2004-130096 A | 4/2004 |
| JP | 2008-264773 A | 11/2008 |
| JP | 2013-081776 A | 5/2013 |
| WO | WO 2007/049717 A1 | 5/2007 |
| WO | WO 2012/061641 A2 | 5/2012 |

OTHER PUBLICATIONS

U.S. Appl. No. 13/657,553, filed Oct. 22, 2012.
U.S. Appl. No. 61/410,603, filed Nov. 5, 2010.
International Search Report and Written Opinion dated May 19, 2015 re Application No. PCT/US2014/053857.
Chinese Office Action, The Frist Office Action, dated Feb. 5, 2018 for Application No. CN 201480063418.5, 7 pgs.
Chinese Search Report dated Jan. 22, 2018, for Application No. CN 201480063418.5, 2 pgs.
European Exam Report dated Jan. 22, 2018 for Application No. EP 14 767 219.0, 8 pgs.
Japanese Office Action, Notification of Reasons for Refusal, dated Jun. 26, 2018 for Application No. JP 2016-515379, 4 pgs.
Japanese Search Report by Registered Searching Organization, Kosaido Co., Ltd., dated May 31, 2018 for Application No. JP 2016-515379, 23 pgs.

* cited by examiner

US 10,231,747 B2

TRANSDUCER FEATURES FOR ULTRASONIC SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 8,461,744 on May 5, 2013, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, issued as U.S. Pat. No. 8,591,536 on Nov. 26, 2013, entitled "Ultrasonic Surgical Instrument Blades," published Feb. 2, 2012, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2015, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, issued as U.S. Pat. No. 9,393,037 on Jul. 19, 2016, entitled "Surgical Instruments with Articulating Shafts," the disclosure of which is incorporated by reference herein; and U.S. patent application Ser. No. 13/657,553, filed Oct. 22, 2012, issued as U.S. Pat. No. 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
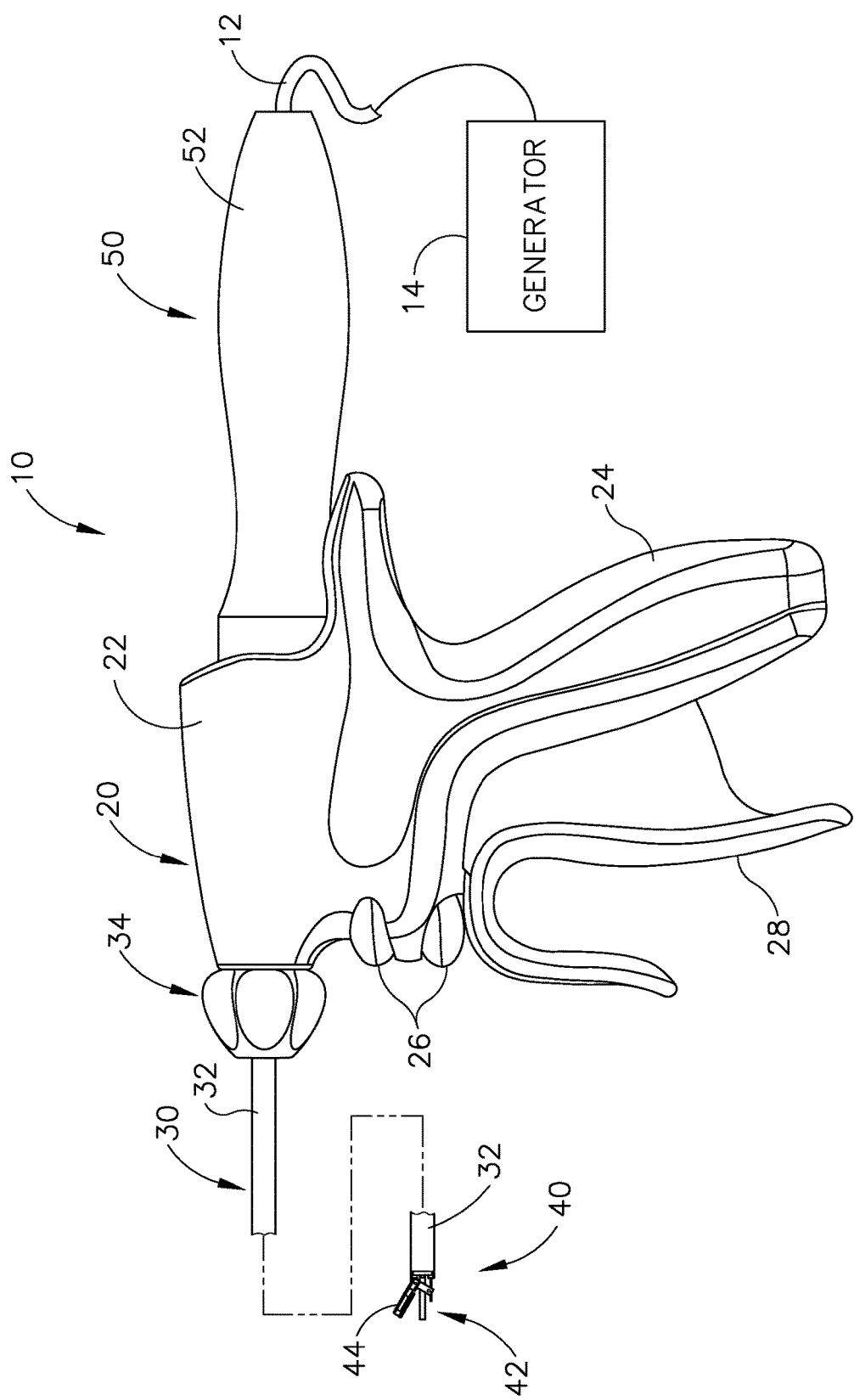
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 illustrates an exemplary ultrasonic surgical instrument (10). At least part of instrument (10) may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,773,444; U.S. Pat. No. 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, issued as U.S. Pat. No. 8,623,027 on Jan. 7, 2014; U.S. Pub. No. 2010/0069940, issued a U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. patent application Ser. No. 13/538,588, issued as U.S. Pat. No. 9,393,037 on Jun. 19, 2016; U.S. patent application Ser. No. 13/657,553, issued as U.S. Pat. No. 9,095,367 on Aug. 4, 2015; and/or U.S. Pat. App. No. 61/410,603. The disclosures of each of the foregoing patents, publications, and applications are incorporated by reference herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handle assembly (20), a shaft assembly (30), and an end effector (40). Handle assembly (20) comprises a body housing (22) including a pistol grip (24). Handle assembly (20) also comprises a pair of buttons (26) and a trigger (28) that is pivotable toward and away from pistol grip (24). It should be understood, however, that various other suitable configurations may be used, including but not limited to a scissor grip configuration. End effector (40) includes an ultrasonic blade (42) and a pivoting clamp arm (44). Clamp arm (44) is coupled with trigger (28) such that clamp arm (44) is pivotable toward ultrasonic blade (42) in response to pivoting of trigger (28) toward pistol grip (24); and such that clamp arm (44) is pivotable away from ultrasonic blade (42) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (50) extends proximally from body (22) of handle assembly (20). Transducer assembly (50) includes a shroud housing (52) that encompasses part of an acoustic assembly (100) as will be described in greater detail below. In the present example, shroud housing (52) is formed of an electrically insulative material (e.g., plastic, etc.). Transducer assembly (50) is coupled with a generator (14) via a cable (12). The acoustic assembly (100) of transducer assembly (50) receives electrical power from generator (14) and converts that power into ultrasonic vibrations through piezoelectric principles. Generator (14) may include a power source and control module that is configured to provide a power profile to transducer assembly (50) that is particularly suited for the generation of ultrasonic vibrations through transducer assembly (50). By way of example only, generator (14) may comprise a GEN 300 sold by Ethicon Endo-Surgery, Inc. of Cincinnati, Ohio. In addition or in the alternative, generator (14) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (14) may be integrated into handle assembly (20), and that handle assembly (20) may even include a battery or other on-board power source such that cable (12) is omitted. Still other suitable forms that generator (14) may take, as well as various features and operabilities that generator (14) may provide, will be apparent to those of ordinary skill in the art in view of the teachings herein.

Figure 2:
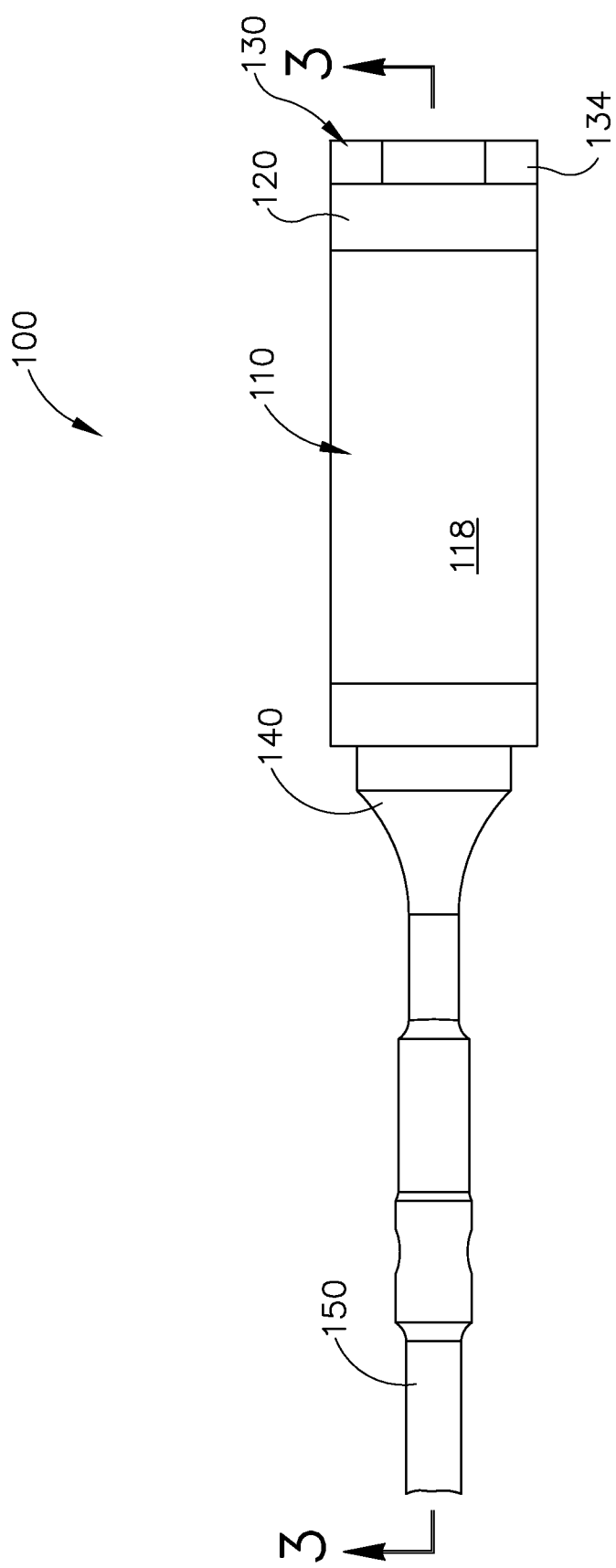
FIG. 2 depicts a partial side elevational view of an acoustic assembly of the instrument of FIG. 1.
Figure 3:
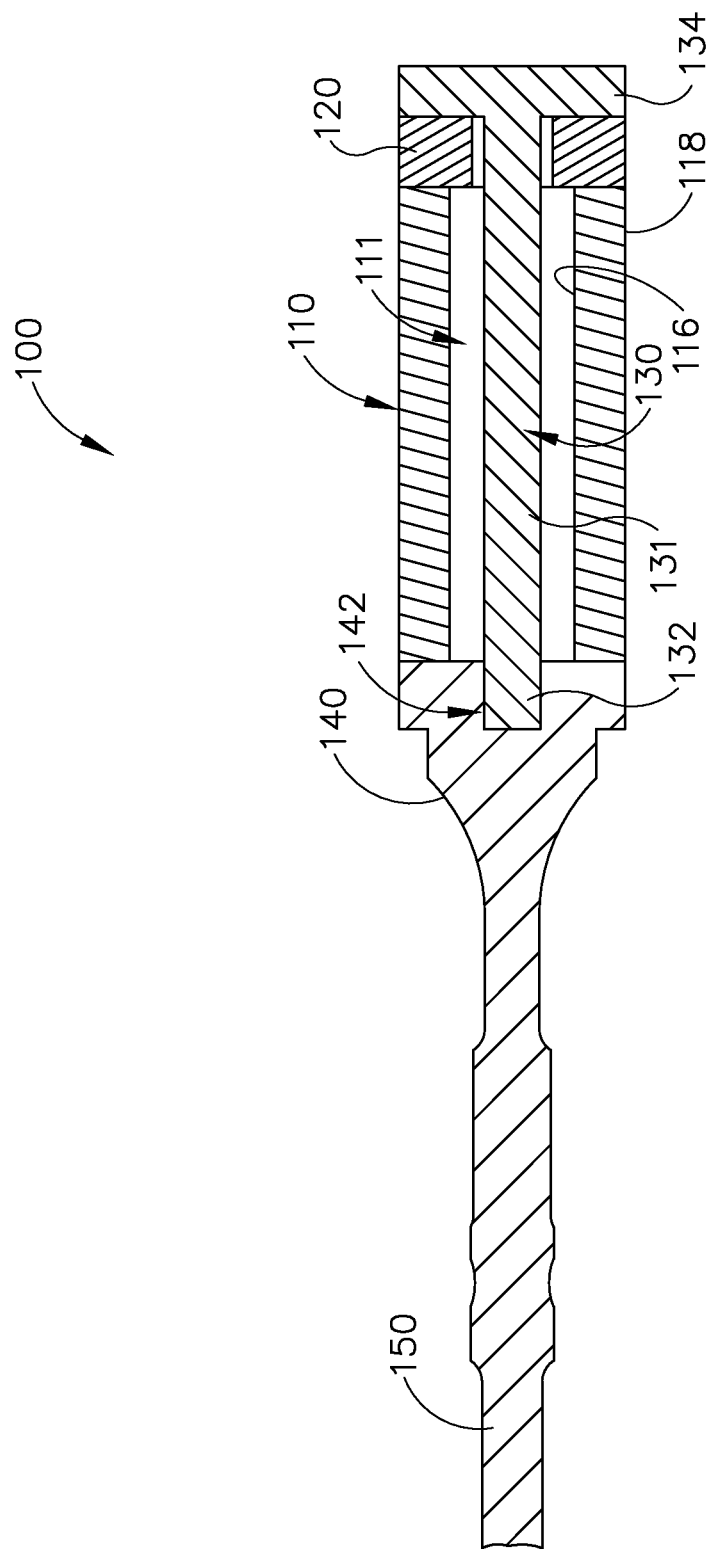
FIG. 3 depicts a cross-sectional view of the acoustic assembly of FIG. 2, taken along line 3-3 of FIG. 2.
Figure 4:
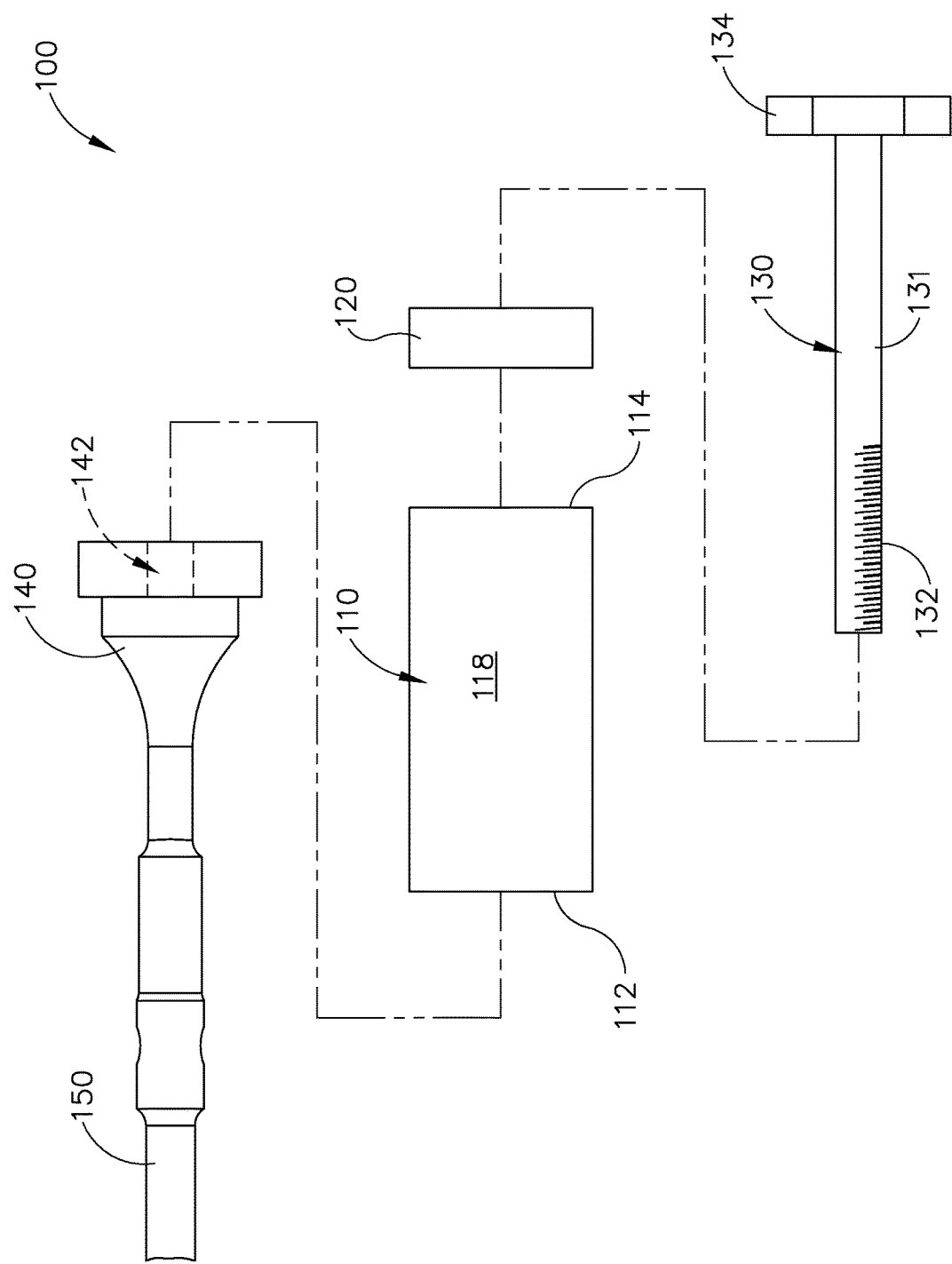
FIG. 4 depicts an exploded side view of the acoustic assembly of FIG. 2.

FIGS. 2-4 show a proximal portion of acoustic assembly (100) of the present example. Acoustic assembly (100) comprises a monolithic piezoelectric transducer element (110), an endmass (120), a bolt (130), a horn (140), and an acoustic waveguide (150). It should be understood that transducer element (110), endmass (120), bolt (130), and horn (140) are all contained within shroud housing (52) in this example. Waveguide (150) extends distally through shaft assembly (30) and terminates in ultrasonic blade (42). In some versions, transducer assembly (50) and shaft assembly (30), including the full length of acoustic assembly (100), are rotatable together relative to handle assembly (20). In particular, the knob (34) shown in FIG. 1 may be manipulated to rotate transducer assembly (50) and shaft assembly (30).

Figure 5:
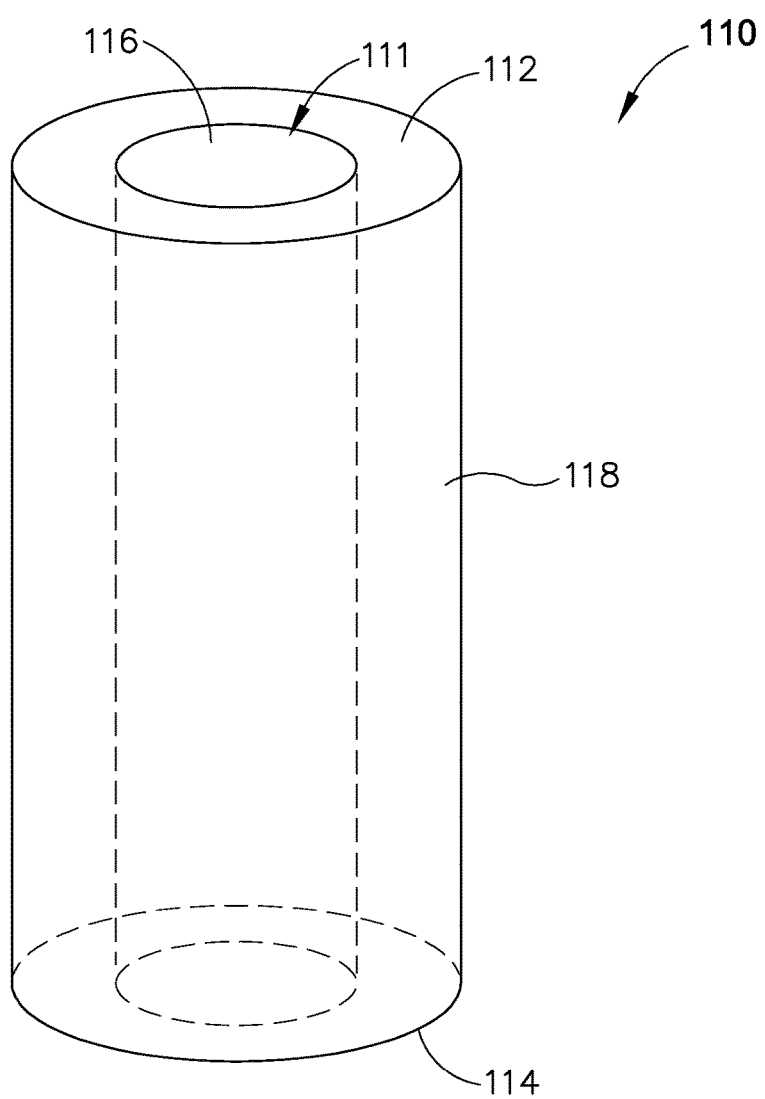
FIG. 5 depicts a perspective view of a monolithic piezoelectric transducer element of the acoustic assembly of FIG. 2.

As best seen in FIGS. 3-4, bolt (130) includes a shank (131) having a threaded distal end (132) that is configured to screw into a complimentarily threaded recess (142) at the proximal end of horn (140). Bolt (130) also includes a head (134) that is configured to compress endmass (120) and transducer element (110) against horn (140) when bolt (130) is tightened relative to horn (140). As best seen in FIG. 5, transducer element (110) of the present example consists of a single, monolithic piece of piezoelectric material that defines a bore (111), such that transducer element (110) has a hollow, elongate, cylindraceous configuration. Transducer element (110) thus includes a distal face (112), a proximal face (114), an inner diameter surface (116), and an outer diameter surface (118). Faces (112, 114) are electrically insulated (e.g., by a coating, film, other feature, etc.); while surfaces (116, 118) are electrically conductive (e.g., with a metallic plating, etc.). Transducer element (110) is configured to convert electrical power into ultrasonic vibrations when a voltage is applied to surfaces (116, 118) (e.g., with surface (116) serving as a ground or neutral path). By way of example only, transducer element (110) may be configured in accordance with at least some of the teachings of U.S. patent application Ser. No. 13/745,385, entitled "Ultrasonic Surgical Apparatus with Silicon Waveguide," filed Jan. 18, 2013, published as 2013/0197550, issued as U.S. Pat. No. 9,797,735 on Aug. 22, 2017, the disclosure of which is incorporated by reference herein. Various examples of how transducer element (110) may receive electrical power will be described in detail below. The ultrasonic vibrations generated by transducer element (110) are communicated via horn (140) to waveguide (150), ultimately reaching blade (42).

In the present example, the distal end of blade (42) is located at a position corresponding to an anti-node associated with resonant ultrasonic vibrations communicated through acoustic assembly (100), in order to tune acoustic assembly (100) to a preferred resonant frequency $f_o$ when the acoustic assembly is not loaded by tissue. When acoustic assembly (100) is energized, the distal end of blade (42) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When acoustic assembly (100) of the present example is activated, these mechanical oscillations are transmitted through waveguide (150) to reach blade (42), thereby providing oscillation of blade (42) at the resonant ultrasonic frequency. Thus, when tissue is secured between blade (42) and clamp arm (44), the ultrasonic oscillation of blade (42) may simultaneously sever the tissue and denature the proteins in adjacent tissue cells, thereby providing a coagulative effect with relatively little thermal spread. In some versions, an electrical current may also be provided through blade (42) and clamp arm (44) to also cauterize the tissue. Still other suitable configurations for an acoustic assembly (100) will be apparent to one or ordinary skill in the art in view of the teachings herein. Similarly, other suitable configurations for end effector (40) will be apparent to those of ordinary skill in the art in view of the teachings herein.

In some versions, shaft assembly (30) includes an articulation section (not shown) that allows end effector (40) to be deflected at various angles relative to the longitudinal axis defined by the outer sheath (32) of shaft assembly. Waveguide (150) may include a flexible section passing through such an articulation section of shaft assembly, allowing waveguide to bend (150) while still communicating ultrasonic vibrations through waveguide (150). By way of example only, such an articulation section and variation of waveguide may be constructed in accordance with at least some of the teachings of U.S. patent application Ser. No. 13/538,588, issued as U.S. Pat. No. 9,393,037 on Jul. 19, 2016, and/or U.S. patent application Ser. No. 13/657,553, issued as U.S. Pat. No. 9,095,367 on Aug. 4, 2015, the disclosures of which are incorporated by reference herein. Of course, articulation is merely optional, such that shaft assembly (30) may simply lack an articulation section in some versions.

II. Exemplary Electrical Coupling Features for Transducer

As noted above, transducer element (110) is configured to convert electrical power into ultrasonic vibrations when a voltage is applied to surfaces (116, 118). The following examples include various features that may be used to apply a voltage to surfaces (116,118) of transducer element (110).

It should be understood that the features described below may be readily incorporated into instrument (10) in numerous ways. Other suitable features that may be used to apply a voltage to surfaces (116,118) of transducer element (110) will be apparent to those of ordinary skill in the art in view of the teachings herein.

A. Exemplary Conductive Coatings for Transducer Element

Figure 6:
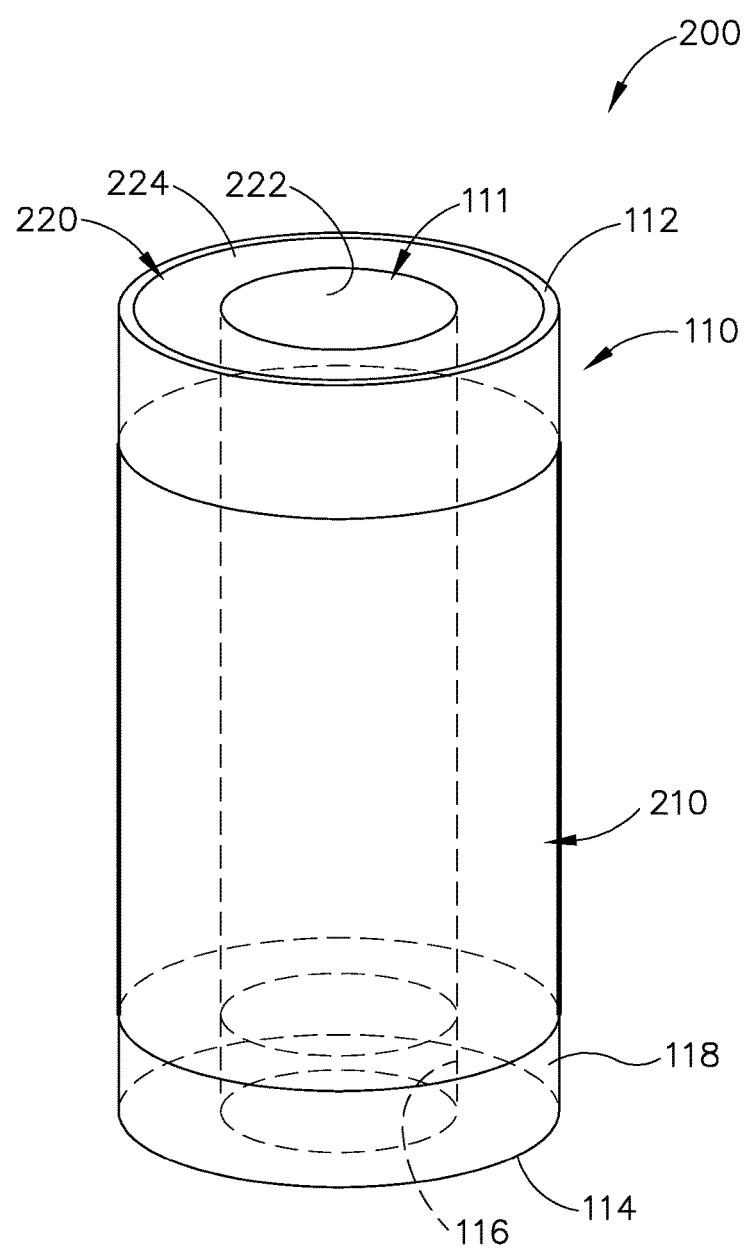
FIG. 6 depicts a perspective view of a monolithic piezoelectric transducer element with an exemplary electrode configuration, suitable for use in the acoustic assembly of FIG. 2.
Figure 7:
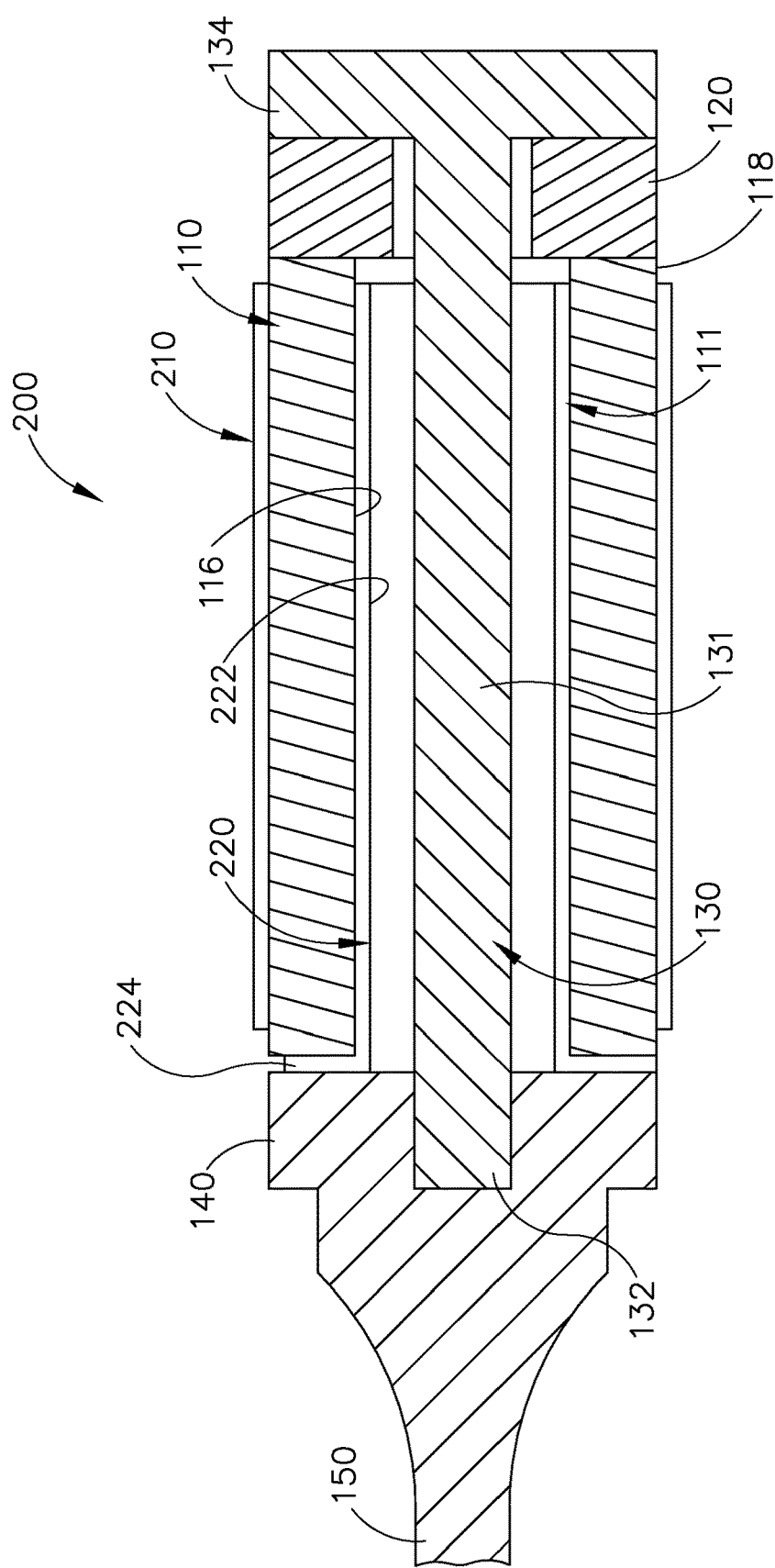
FIG. 7 depicts a cross-sectional view of an exemplary acoustic assembly incorporating the transducer element of FIG. 6.

FIGS. 6-7 show an assembly (200) that includes transducer element (110) with a first electrode assembly (210) and a second electrode assembly (220). First electrode assembly (210) is positioned about outer diameter surface (118) of transducer element (110). First electrode assembly (210) terminates at each end before reaching faces (112, 114). Thus, when transducer element (110) is secured between an endmass (120) and a horn (140), first electrode assembly (210) does not contact endmass (120) or horn (140). By way of example only, first electrode assembly (212) may terminate approximately 0.20 inches from distal face (112); and approximately 0.20 inches from proximal face (114)). Second electrode assembly (220) includes a cylindraceous portion (222) that is positioned along a portion of inner diameter surface (116); and a flange portion (224) that is positioned along distal face (112). Second electrode assembly (220) terminates at one end before reaching proximal face (114); and at the other end before reaching outer diameter surface (118). By way of example only, second electrode assembly (220) may terminate approximately 0.20 inches from proximal face (114); and approximately 0.20 inches from outer diameter surface (118). In some versions, second electrode assembly (220) extends along proximal face (114), with or without also extending along distal face (112). In the present example, electrode assembly (210) serves as an active electrode; while electrode assembly (220) serves as a ground or neutral electrode. Of course, these roles may be reversed, if desired.

Electrode assemblies (210, 220) are formed of conductive materials that are configured to communicate opposing charge to surfaces (116, 118), with the resulting voltage activating transducer element (110) to generate ultrasonic vibrations as noted above. In some versions, electrode assemblies (210, 220) are formed of beryllium copper (BeCu), brass, or some other copper alloy. Various other suitable materials that may be used to form electrode assemblies (210, 220) will be apparent to those of ordinary skill in the art in view of the teachings herein. It should also be understood that electrode assemblies (210, 220) may be formed in numerous different ways. By way of example only, electrode assemblies (210, 220) may be formed through a physical vapor deposition (PVD) process, a sputter coating process, or some other kind of process. Other suitable ways in which electrode assemblies (210, 220) may be formed will be apparent to those of ordinary skill in the art in view of the teachings herein. Furthermore, it should be understood that electrode assemblies (210, 220) may receive power in numerous different ways (e.g., from various kinds of components interposed between electrode assemblies (210, 220) and generator (14)). Several merely illustrative examples of how power may be communicated to the interior of a transducer element (110) and the exterior of a transducer element (110) will be described in greater detail below. It should be understood that, in some versions, assembly (200) may rotate about the longitudinal axis defined by waveguide (150) while assembly (200) receives continuous electrical power via electrode assemblies (210, 220).

In versions where bolt (130), horn (140), and waveguide (150) are formed of electrically conductive material, any of those components may be in contact with a component that provides electrical power (e.g., from generator (14), etc.), in order to electrically couple with inner diameter surface (116) via flange portion (224) and cylindraceous portion (222) of second electrode assembly (220). In other words, bolt (130), horn (140), waveguide (150), and second electrode assembly (220) may all be in electrical communication with inner diameter surface (116), such that bolt (130), horn (140), waveguide (150), and second electrode assembly (220) may all provide electrical continuity with inner diameter surface (116).

B. Exemplary Conductive Coatings with Conductive Tabs for Transducer Element

Figure 8:
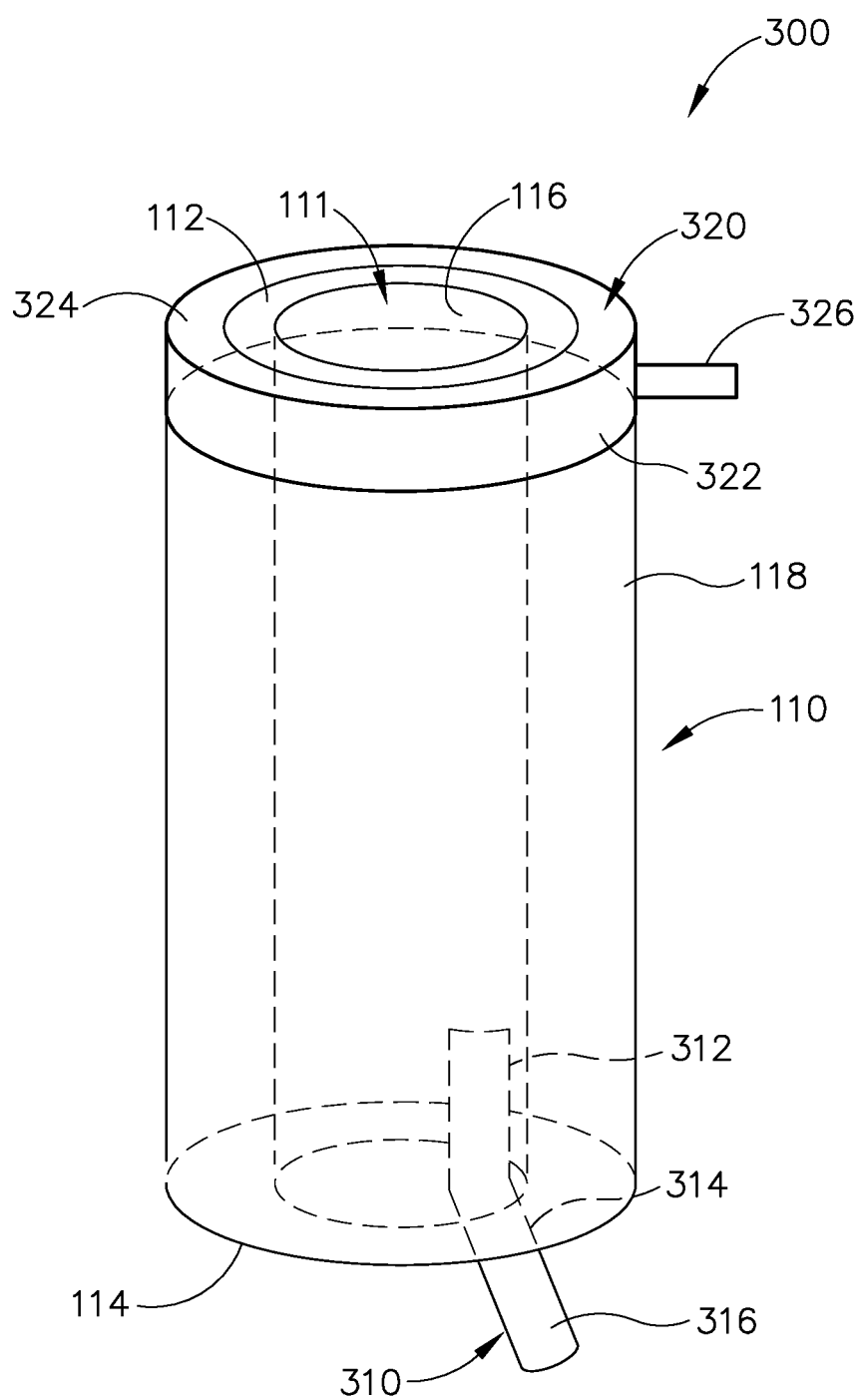
FIG. 8 depicts a perspective view of a monolithic piezoelectric transducer element with another exemplary electrode configuration, suitable for use in the acoustic assembly of FIG. 2.
Figure 9:
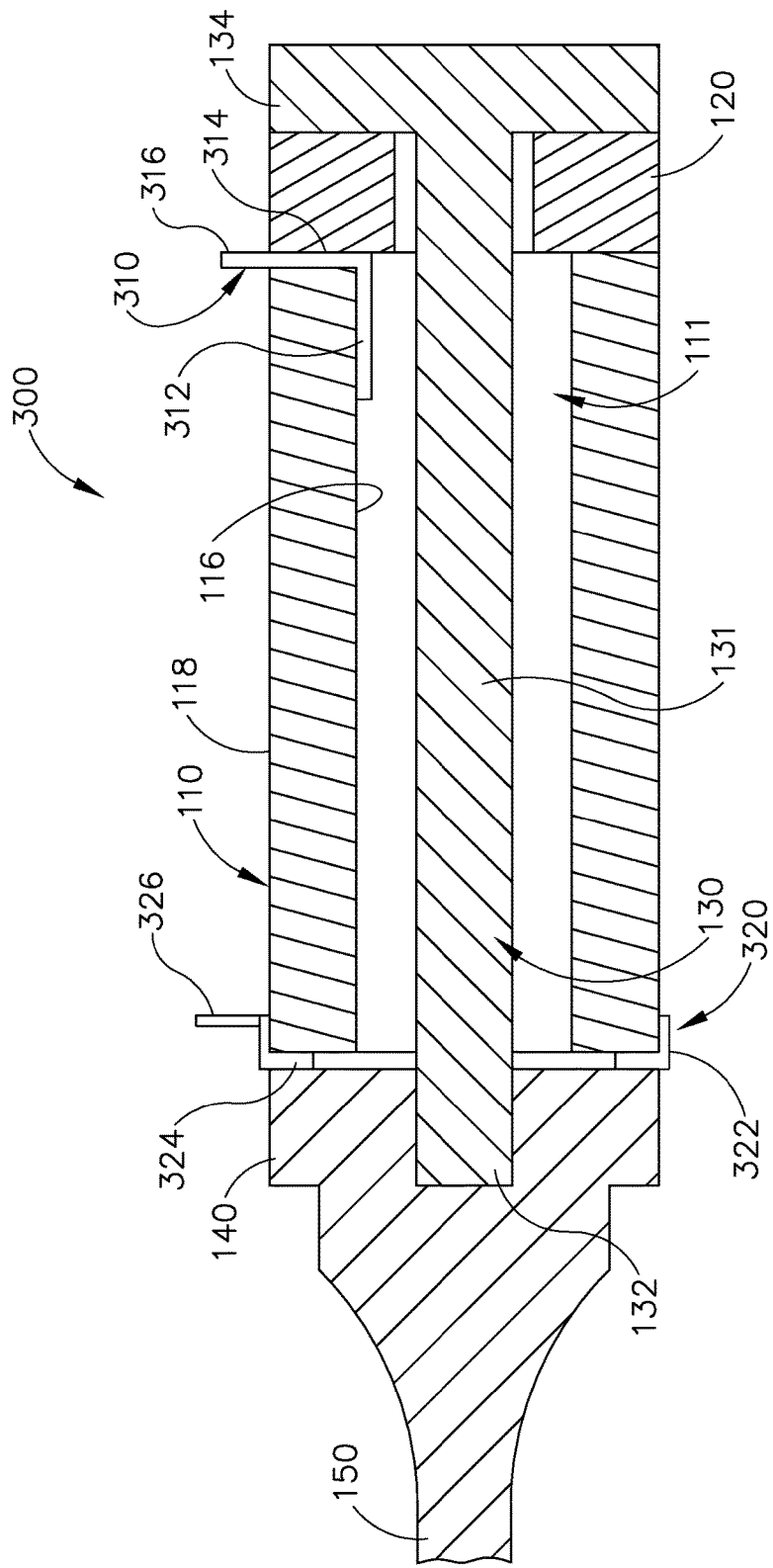
FIG. 9 depicts a cross-sectional view of an exemplary acoustic assembly incorporating the transducer element of FIG. 8.

FIGS. 8-9 show another exemplary assembly (300) that includes transducer element (110) with a first electrode assembly (310) and a second electrode assembly (320). First electrode assembly (310) includes a first portion (312) extending along a portion of inner diameter surface (116), a second portion (314) extending along a portion of proximal face (114), and an outwardly extending tab (316). In some versions, tab (316) is flexible. Second electrode assembly (320) includes a first portion (322) extending along a portion of outer diameter surface (118), a second portion (324) extending along a portion of distal face (112), and an outwardly extending tab (326). In some versions, tab (326) is flexible. In the present example, electrode assembly (310) serves as an active electrode; while electrode assembly (320) serves as a ground or neutral electrode. Of course, these roles may be reversed, if desired.

Electrode assemblies (310, 320) are formed of conductive materials that are configured to communicate opposing charge to surfaces (116, 118), with the resulting voltage activating transducer element (110) to generate ultrasonic vibrations as noted above. In some versions, electrode assemblies (310, 320) are formed of beryllium copper (BeCu), brass, or some other copper alloy. Various other suitable materials that may be used to form electrode assemblies (310, 320) will be apparent to those of ordinary skill in the art in view of the teachings herein. It should also be understood that electrode assemblies (310, 320) may be formed in numerous different ways. By way of example only, electrode assemblies (310, 220) may be formed through a physical vapor deposition (PVD) process, a sputter coating process, or some other kind of process. Other suitable ways in which electrode assemblies (310, 320) may be formed will be apparent to those of ordinary skill in the art in view of the teachings herein. Furthermore, it should be understood that electrode assemblies (310, 320) may receive power in numerous different ways (e.g., from various kinds of components interposed between electrode assemblies (310, 320) and generator (14)). Several merely illustrative examples of how power may be communicated to the interior of a transducer element (110) and the exterior of a transducer element (110) will be described in greater detail below.

In versions where bolt (130), horn (140), and waveguide (150) are formed of electrically conductive material, any of those components may be in contact with a component that provides electrical power (e.g., from generator (14), etc.), in order to electrically couple with either inner diameter surface (116) via first electrode assembly (310) or outer diameter surface (118) via second electrode assembly (320). In other words, bolt (130), horn (140), waveguide (150), and first electrode assembly (310) may all be in electrical communication with inner diameter surface (116), such that bolt (130), horn (140), waveguide (150), and first electrode assembly (310) may all provide electrical continuity with inner diameter surface (116). Alternatively, bolt (130), horn (140), waveguide (150), and second electrode assembly (320) may all be in electrical communication with outer diameter surface (118), such that bolt (130), horn (140), waveguide (150), and second electrode assembly (320) may all provide electrical continuity with outer diameter surface (118).

While not shown in the drawings, it should be understood that assembly (300) may also include one or more electrical insulator elements. For instance, both electrode assemblies (310, 320) may be electrically isolated relative to the assembly formed by endmass (120), bolt (130), and horn (140). In versions where one of the electrode assemblies (310, 320) is in electrical communication with the assembly formed by endmass (120), bolt (130), and horn (140), the other electrode assembly (310, 320) may be electrically isolated from the assembly formed by endmass (120), bolt (130), and horn (140). By way of example only, an electrical insulator element may include an insulative coating, an insulative washer, and/or various other types of components. As another merely illustrative example, in versions where second electrode assembly (320) is in electrical communication with horn (140), first electrode assembly (310) may be electrically isolated from horn (140) by using an electrically insulative endmass (120) and/or an electrically insulative bolt (130). Various other suitable ways in which appropriate electrical insulation may be provided in assembly (300) will be apparent to those of ordinary skill in the art in view of the teachings herein.

C. Exemplary Conductive Coatings with Conductive Shims for Transducer Element

Figure 10:
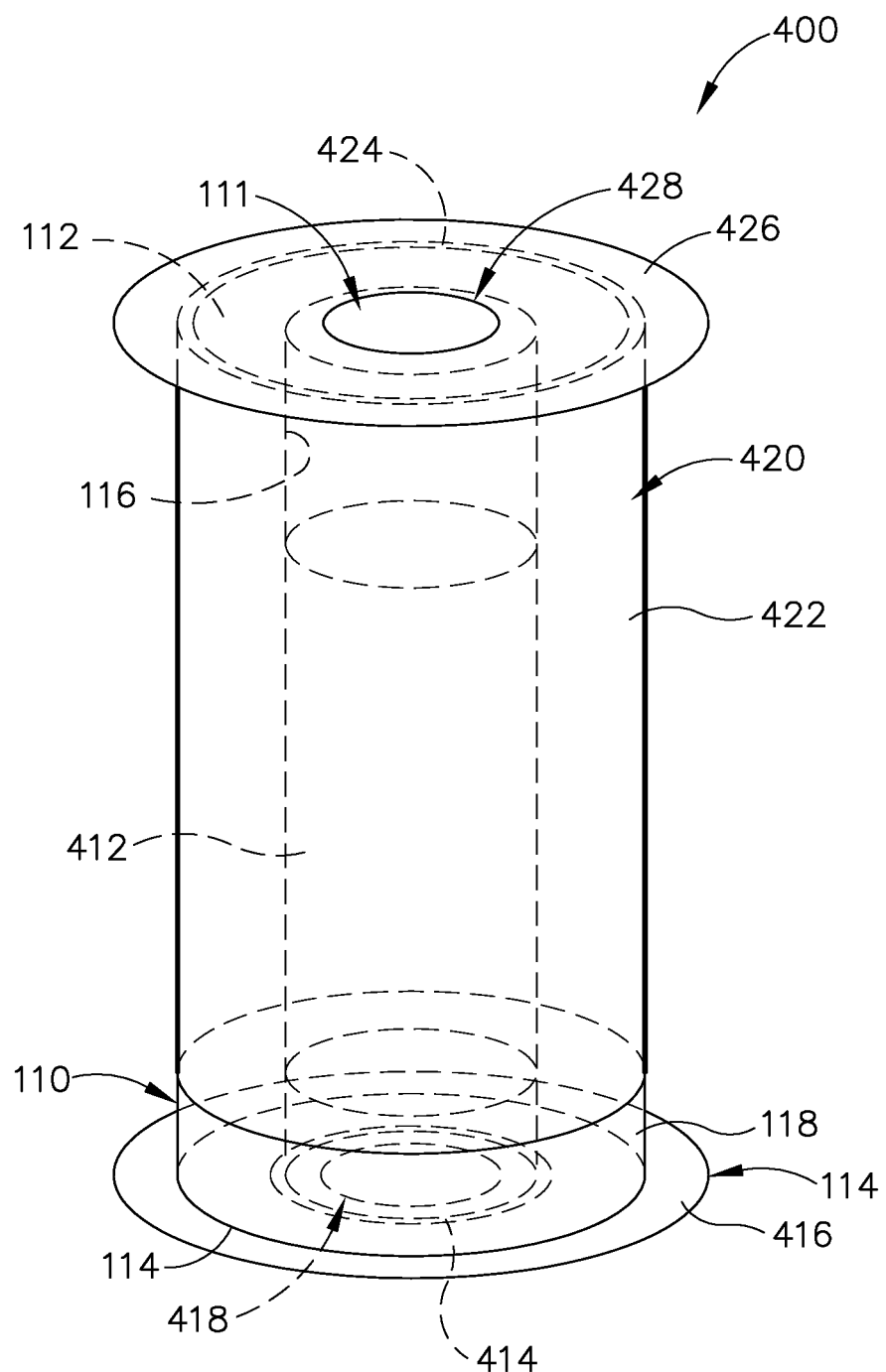
FIG. 10 depicts a perspective view of a monolithic piezoelectric transducer element with another exemplary electrode configuration, suitable for use in the acoustic assembly of FIG. 2.
Figure 11:
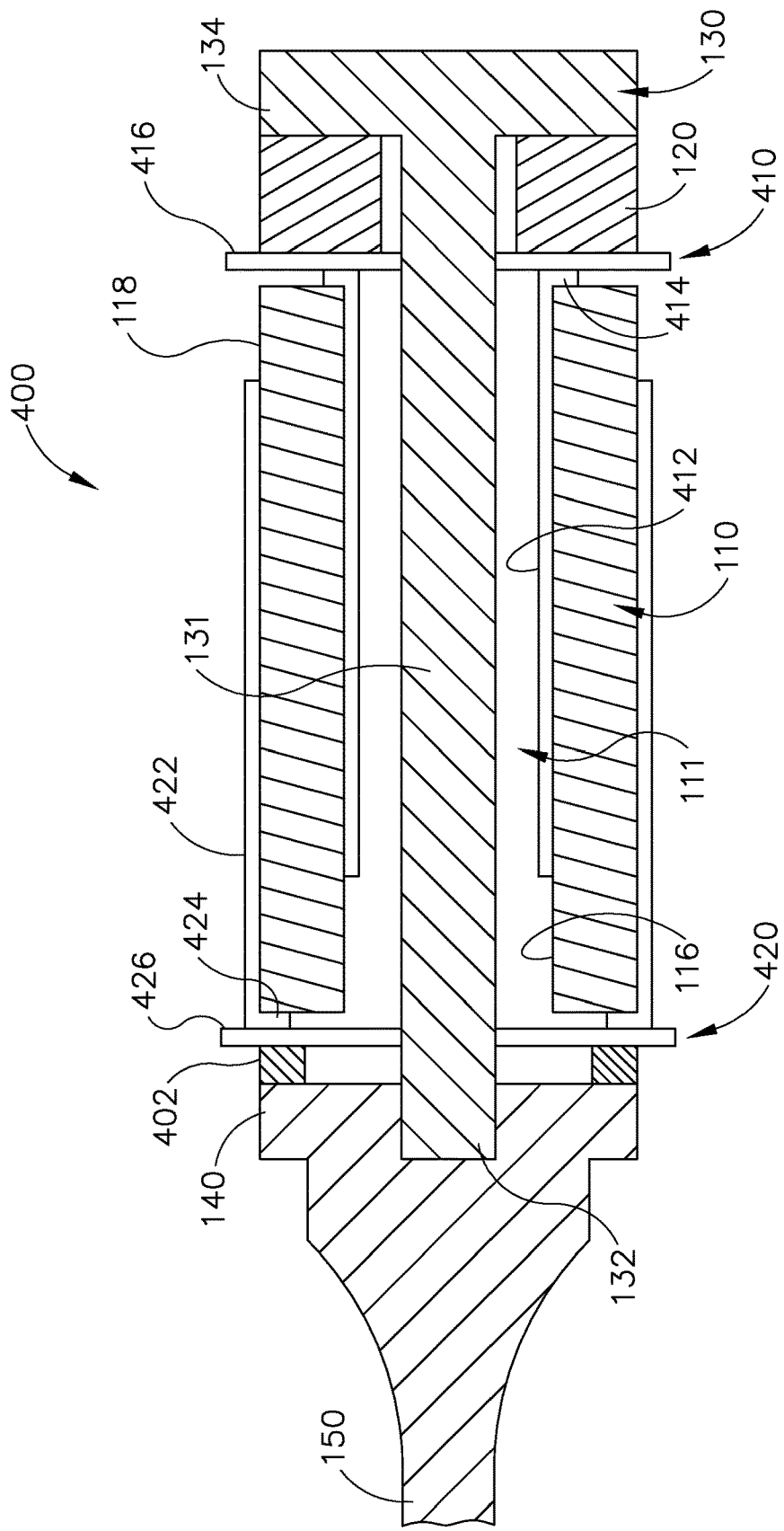
FIG. 11 depicts a cross-sectional view of an exemplary acoustic assembly incorporating the transducer element of FIG. 10.

FIGS. 10-11 show another exemplary assembly (400) that includes transducer element (110) with a first electrode assembly (410) and a second electrode assembly (420). First electrode assembly (410) includes a first portion (412) extending along a portion of inner diameter surface (116), a second portion (414) extending along a portion of proximal face (114), and an outwardly extending conductive shim (416). In some instances, first portion (412) terminates approximately 0.20 inches from distal face (112). In some instances, second portion (414) extends along approximately ⅓ of the radial width of proximal face (114). Other suitable dimensions will be apparent to those of ordinary skill in the art in view of the teachings herein. Shim (416) of the present example defines an opening (418) that is sized to receive shank (131) of bolt (130) without contacting shank (131).

Second electrode assembly (420) includes a first portion (422) extending along a portion of outer diameter surface (118), a second portion (424) extending along a portion of distal face (112), and an outwardly extending conductive shim (426). In some instances, second portion (424) extends along approximately ⅓ of the radial width of distal face (112). In some instances, first portion (422) terminates approximately 0.20 inches from proximal face (114). In some instances, second portion (424) extends along approximately ⅓ of the radial width of distal face (112). Other suitable dimensions will be apparent to those of ordinary skill in the art in view of the teachings herein. Shim (426) of the present example defines an opening (428) that is sized to receive shank (131) of bolt (130) without contacting shank (131). In the present example, electrode assembly (410) serves as an active electrode; while electrode assembly (420) serves as a ground or neutral electrode. Of course, these roles may be reversed, if desired.

Electrode assemblies (410, 420) are formed of conductive materials that are configured to communicate opposing charge to surfaces (116, 118), with the resulting voltage activating transducer element (110) to generate ultrasonic vibrations as noted above. In some versions, electrode assemblies (410, 420) are formed of beryllium copper (BeCu), brass, or some other copper alloy. Various other suitable materials that may be used to form electrode assemblies (410, 420) will be apparent to those of ordinary skill in the art in view of the teachings herein. It should also be understood that electrode assemblies (410, 420) may be formed in numerous different ways. By way of example only, shims (416, 426) may be formed by stamping/die-cutting sheet metal while the rest of electrode assemblies (410, 420) are formed through a physical vapor deposition (PVD) process, a sputter coating process, or some other kind of process. Other suitable ways in which electrode assemblies (410, 420) may be formed will be apparent to those of ordinary skill in the art in view of the teachings herein. Furthermore, it should be understood that electrode assemblies (410, 420) may receive power in numerous different ways (e.g., from various kinds of components interposed between electrode assemblies (410, 420) and generator (14)). By way of example only, shims (416, 426) may be in contact with respective conductive brushes, leaf springs, or other types of electrical contact members. It should be understood that, in some versions, assembly (400) may rotate about the longitudinal axis defined by waveguide (150) while assembly (400) receives continuous electrical power via electrode assemblies (410, 420).

In versions where bolt (130), horn (140), and waveguide (150) are formed of electrically conductive material, any of those components may be in contact with a component that provides electrical power (e.g., from generator (14), etc.), in order to electrically couple with either inner diameter surface (116) via first electrode assembly (410) or outer diameter surface (118) via second electrode assembly (420). In other words, bolt (130), horn (140), waveguide (150), and first electrode assembly (410) may all be in electrical communication with inner diameter surface (116), such that bolt (130), horn (140), waveguide (150), and first electrode assembly (410) may all provide electrical continuity with inner diameter surface (116). Alternatively, bolt (130), horn (140), waveguide (150), and second electrode assembly (420) may all be in electrical communication with outer diameter surface (118), such that bolt (130), horn (140), waveguide (150), and second electrode assembly (420) may all provide electrical continuity with outer diameter surface (118).

As shown in FIG. 11, assembly of the present example includes an electrically insulative washer (402) interposed between horn (140) and shim (426) of second electrode assembly (420). Washer (402) thus electrically isolates second electrode assembly (420) and outer diameter surface (118) from the assembly of bolt (130), horn (140), and waveguide (150). Washer (402) may be formed of ceramic and/or any other suitable electrically insulative material(s). In addition to or as an alternative to washer (402) being interposed between horn (140) and shim (426) of second electrode assembly (420), a washer (402) may be interposed between shim (416) of first electrode assembly (410) and endmass (120) (or between endmass (120) and head (134) of bolt (134), etc.) in order to electrically isolate first electrode assembly (410) and inner diameter surface (116) from the assembly of bolt (130), horn (140), and waveguide (150). Various other suitable ways in which appropriate electrical insulation may be provided in assembly (400) will be apparent to those of ordinary skill in the art in view of the teachings herein.

D. Exemplary Conductive Foam Assembly for Transducer Element

Figure 12:
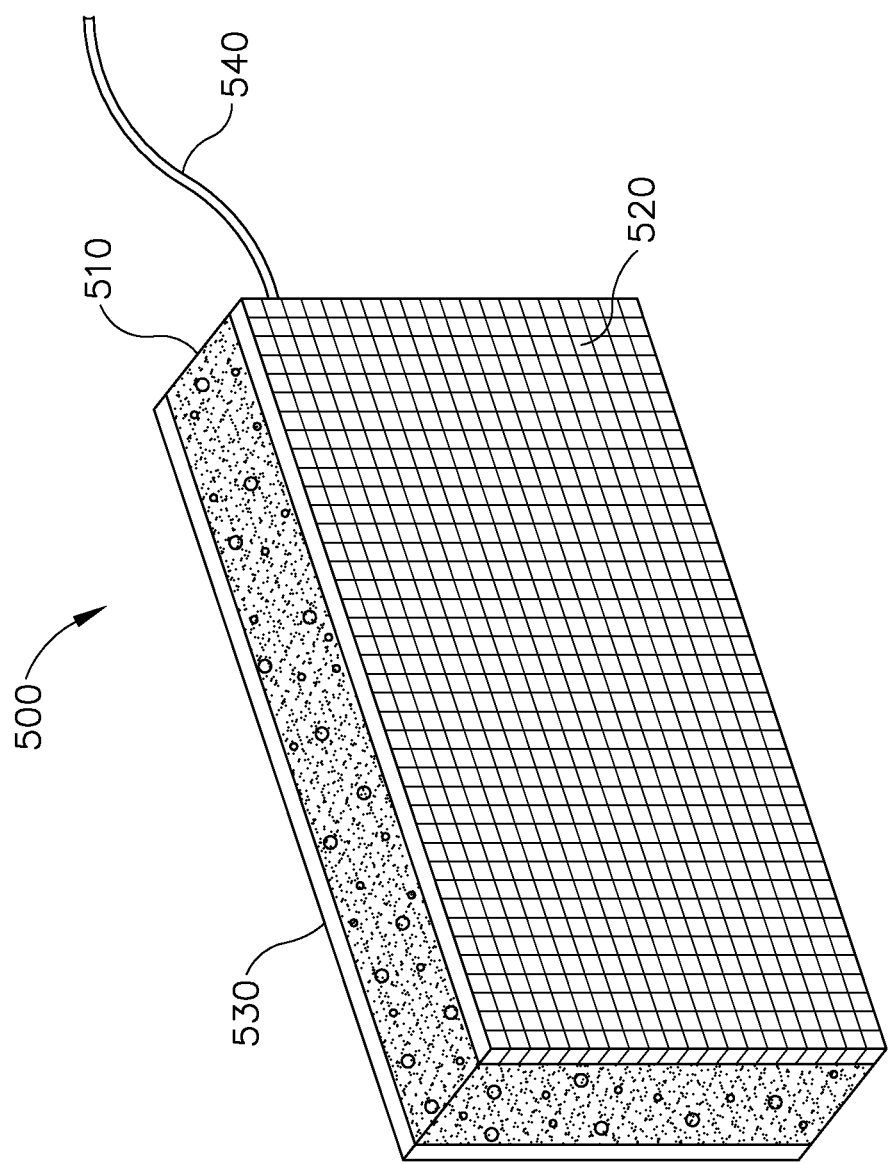
FIG. 12 depicts a perspective view of an exemplary conductor pad.
Figure 13:
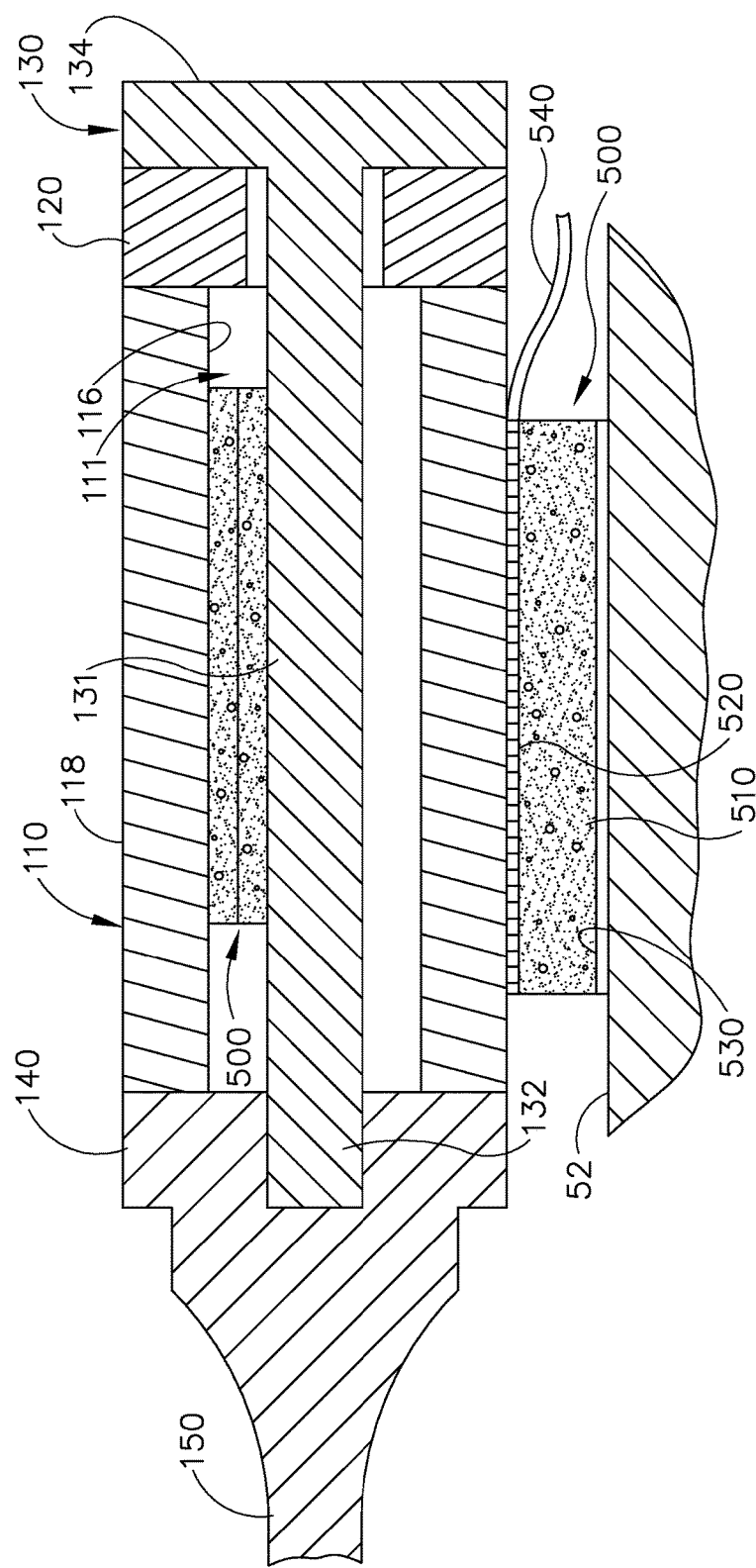
FIG. 13 depicts a cross-sectional view of an exemplary acoustic assembly incorporating the conductor pad of FIG. 12.
Figure 14:
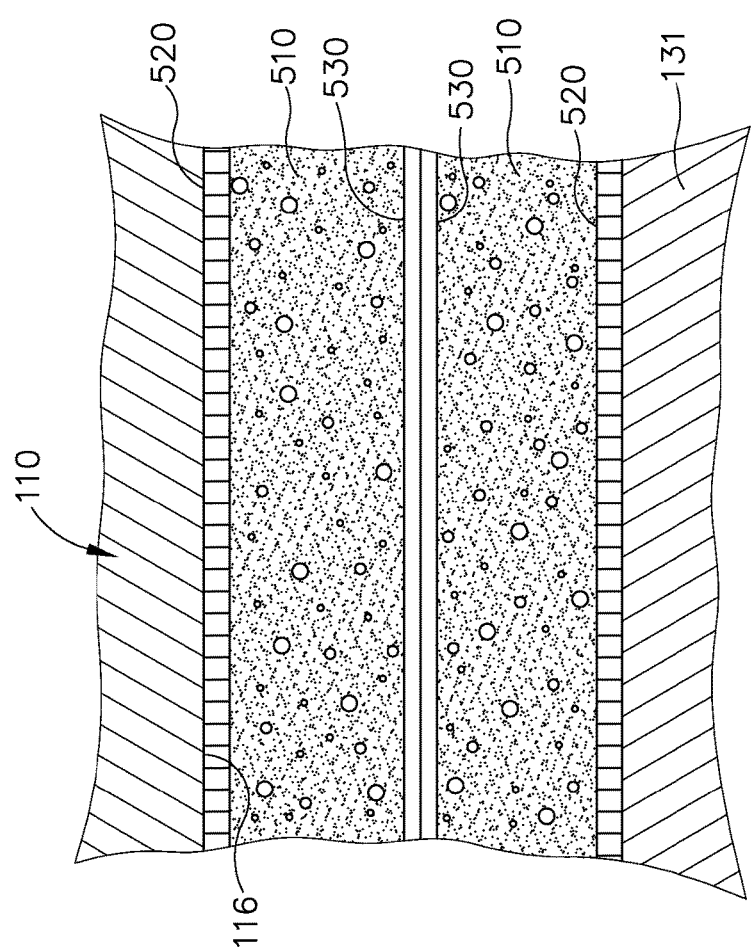
FIG. 14 shows an enlarged cross-sectional view of an interior conductor pad in the assembly of FIG. 13.

FIGS. 12-14 show an exemplary foam assembly (500) that may be used to provide electrical contact for surfaces (116, 118) of transducer element (110). As best seen in FIG. 12, foam assembly (500) comprises a foam pad (510) that is interposed between a conductive layer (520) and an adhesive layer (530). A wire (540) extends from conductive layer (520) and provides electrical communication with conductive layer (520). Wire (540) is further coupled with generator (14). Foam pad (510) of the present example is electrically insulative and is also resiliently biased to assume the expanded configuration shown in FIG. 12. Various suitable materials that may be used to form foam pad (510) will be apparent to those of ordinary skill in the art in view of the teachings herein. Conductive layer (520) may be formed of a conductive foil (e.g., copper or copper alloy, etc.), a conductive mesh or fabric (e.g., a fabric with copper or copper alloy threads woven in, etc.), a set of conductive strips, etc. Various other suitable ways in which conductive layer (520) may be formed will be apparent to those of ordinary skill in the art in view of the teachings herein. Adhesive layer (530) may include a pressure sensitive adhesive and/or any other suitable kind of pressure sensitive adhesive. In some other versions, adhesive layer (530) is omitted. By way of example only, some versions of foam assembly (500) may be held in place due to friction and the resilient bias provided by foam pad (510).

FIG. 13 shows two foam assemblies (500) engaging transducer element (110). In particular, one foam assembly (500) is interposed between outer diameter surface (118) of transducer element (110) and shroud housing (52) of transducer assembly (50). Conductive layer (520) bears against outer diameter surface (118) due to the resilience of foam pad (510). Adhesive layer (530) secures foam assembly (500) to shroud housing (52). While not shown in FIG. 13, it should be understood that outer diameter surface (118) may include an electrode like first electrode assembly (210) and/or some other feature that is in electrically communicative contact with conductive layer (520). It should also be understood that transducer element (110) may rotate about the longitudinal axis defined by waveguide (150) while outer diameter surface (118) maintains contact (and, hence, electrical continuity) with conductive layer (520).

As also shown in FIG. 13, but as best seen in FIG. 14, another foam assembly (500) is positioned in bore (111) of transducer element (110), interposed between shank (131) of bolt (130) and inner diameter surface (116) of transducer element (110). This foam assembly (500) is folded in half, with two regions of adhesive layer (530) in apposition. Thus, one region of conductive layer (520) is in contact with shank (131) of bolt (130) while another region of conductive layer (520) is in contact with inner diameter surface (116). These regions of conductive layer (520) bear against shank (131) and inner diameter surface (116) due to the resilience of foam pad (510). It should be understood that inner diameter surface (116) may include an electrode (e.g., a coating of copper or copper alloy, etc.) in accordance with any of the various teachings herein. It should also be understood this foam assembly (500) in bore (111) provides a path for electrical communication between shank (131) of bolt (130) and inner diameter surface (116) of transducer element (110). One merely illustrative example of how bolt (130) may be electrically coupled with generator (14) (or some other kind of power source) will be described in greater detail below with reference to FIGS. 15-16. Other suitable examples will be apparent to those of ordinary skill in the art in view of the teachings herein.

III. Exemplary Alternative Contact Features for Inner Diameter of Cylindraceous Piezoelectric Transducer Element The examples described above include various features that may be used to provide electrical communication with surfaces (116, 118) of transducer element (110), to thereby activate transducer element (110) to generate ultrasonic vibrations through waveguide (150). The examples described below include various other features that may be used to provide electrical communication with inner diameter surface (116) in particular. It should be understood that the examples described below may be readily combined with any of the teachings herein relating to ways in which electrical communication may be provided to outer diameter surface (118). Other suitable instrument configurations in which the below teachings may be applied will be apparent to those of ordinary skill in the art.

The examples described below include various features that are configured to contact either inner diameter surface (116) directly or some conductive material that is deposited on or otherwise applied to inner diameter surface (116). By way of example only, inner diameter surface (116) may include a conductive coating or insert (e.g., BeCu, brass, some other copper alloy, etc.) that is in contact with any of the various features described below, in order to provide electrical communication with inner diameter surface (116). It should also be understood that each of the various below-described electrical contact features may be longitudinally positioned at (or positioned to make contact at) a location corresponding to a node associated with resonant ultrasonic vibrations communicated through acoustic assembly (100). To the extent that the electrical contact features are not initially positioned at such nodal locations, some such electrical contact features may eventually migrate to such positions after a certain time period during which acoustic assembly (100) is activated. In other words, the vibrations communicated through acoustic assembly (100) may eventually drive electrical contact features to nodal locations.

A. Exemplary Conductive Bolt Cap

Figure 15:
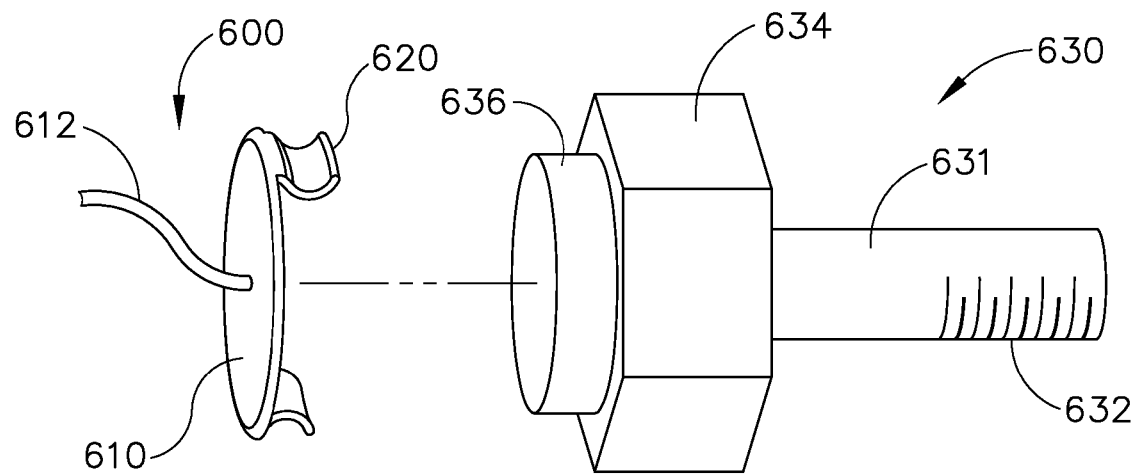
FIG. 15 depicts an exploded perspective view of an exemplary head clip and bolt assembly.
Figure 16:
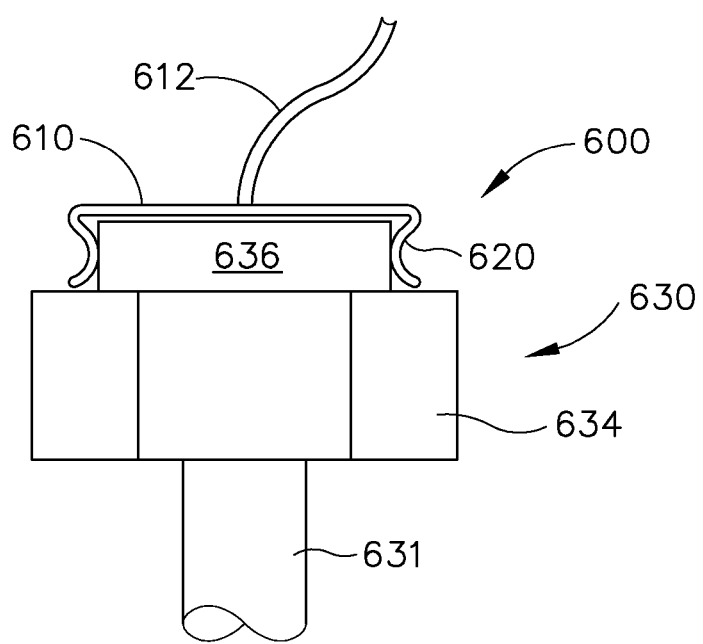
FIG. 16 depicts a partial side elevational view of the head clip and bolt assembly of FIG. 15.

The various examples of electrical contact features described below are configured to provide a path for electrical communication between bolt (130) and inner diameter surface (116) of transducer element (110). In other words, the various electrical contact features described below cooperate with bolt (130) to provide electrical continuity between generator (14) (or some other power source) and inner diameter surface (116) of transducer element (110). It should be understood that various kinds of features may be interposed between bolt (130) and generator (14) (or some other power source) in order to provide such electrical continuity. FIGS. 15-16 show one merely illustrative example of a feature that may be used to provide electrical continuity between bolt (130) and generator (14) (or some other power source). In particular, FIGS. 15-16 show a cap (600) that may be coupled with a modified bolt (630).

Bolt (630) of the present example is formed of a conductive material and includes a shank (631) having a distal threaded region (632), a head (634), and a cylindraceous contact portion (636) formed in head (634). It should be understood that bolt (630) may readily serve as a substitute for bolt (130) in any of the examples described herein. Cap (600) of the present example is also formed of a conductive material and comprises a plate (610) with a pair of resilient arms (620). Cap (600) is configured such that plate (610) fits over contact portion (636) while arms (620) contact the sidewall of contact portion (636). Arms (620) are preformed to define a gap that is less than the diameter of contact portion (636), such that arms (620) resiliently bear against the sidewall of contact portion (636). While only two arms (620) are shown, it should be understood that any suitable number of arms (620) may be used. A wire (612) is coupled with plate (610). Wire (612) is also further coupled with generator (14) (or some other power source), such that wire (612) and cap (600) provide a path for electrical communication between bolt (630) and generator (14) (or some other power source).

In some instances, bolt (630) (and the rest of acoustic assembly (100) that is distal to bolt (630)) is rotatable relative to handle assembly (20), such as to re-orient end effector (40) about the longitudinal axis defined by shaft assembly (30). Cap (600) and wire (612) may remain stationary during such rotation. Arms (620) may provide sliding engagement with contact portion (636), such that cap (600) maintains electrical continuity with bolt (630) even as bolt (630) rotates relative to cap (600). Other suitable relationships that may be provided between cap (600) and bolt (630) will be apparent to those of ordinary skill in the art in view of the teachings herein.

It should be understood that cap (600) may be incorporated into any of the below described examples of configurations that may be used to provide electrical continuity between a bolt (130) (or a variation thereof) and inner diameter surface (116) of transducer element (110). In other words, the below described examples may be implemented to provide electrical continuity between a bolt (130) (or a variation thereof) and inner diameter surface (116) of transducer element (110); while cap (600) may be implemented to provide electrical continuity between the same bolt (130) (or variation thereof) and generator (14) (or some other power source). Alternatively, any other suitable structures may be used to provide electrical continuity between a bolt (130) (or variation thereof) and generator (14) (or some other power source) as will be apparent to those of ordinary skill in the art in view of the teachings herein.

B. Exemplary Resiliently Biased Contact Features for Inner Diameter of Cylindraceous Piezoelectric Transducer Element In some instances, an electrical contact feature may be resiliently biased to assume an expanded configuration. In some such instances, the electrical contact feature may be compressed to fit within bore (111) of transducer element (110), such that the electrical contact feature resiliently bears outwardly on inner diameter surface (116) to maintain contact with (and, hence, electrical continuity with) inner diameter surface (116). Another portion of such a resiliently biased electrical contact feature may be coupled with (and, hence, in electrical continuity with) bolt (130). Various illustrative examples of resiliently biased electrical contact features will be described in greater detail below, while further examples will be apparent to those of ordinary skill in the art in view of the teachings herein.

1. Exemplary Wrapped Conductor with Resiliently Biased Arm Pairs

Figure 17:
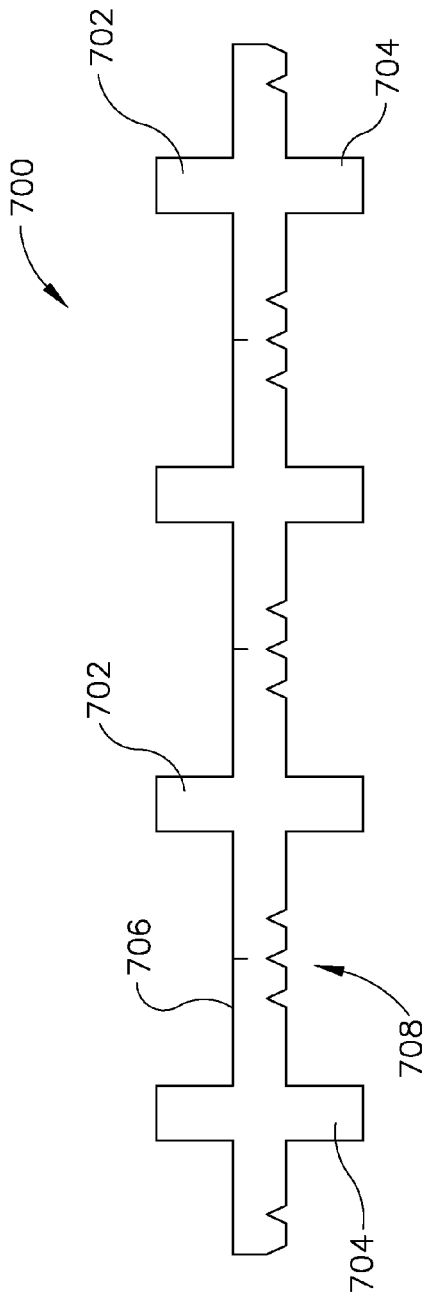
FIG. 17 depicts an exemplary conductor in a flat, unwrapped configuration.
Figure 18:
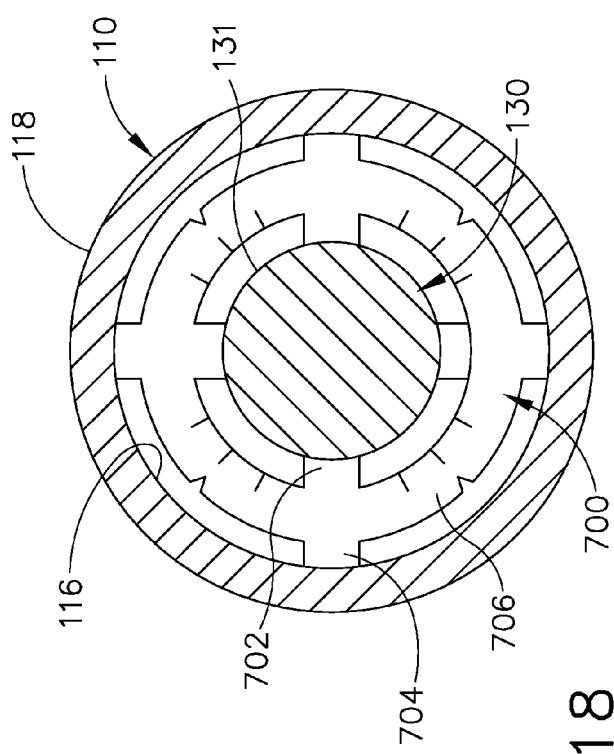
FIG. 18 depicts a cross-sectional end view of an exemplary acoustic assembly incorporating the conductor of FIG. 17.
Figure 19:
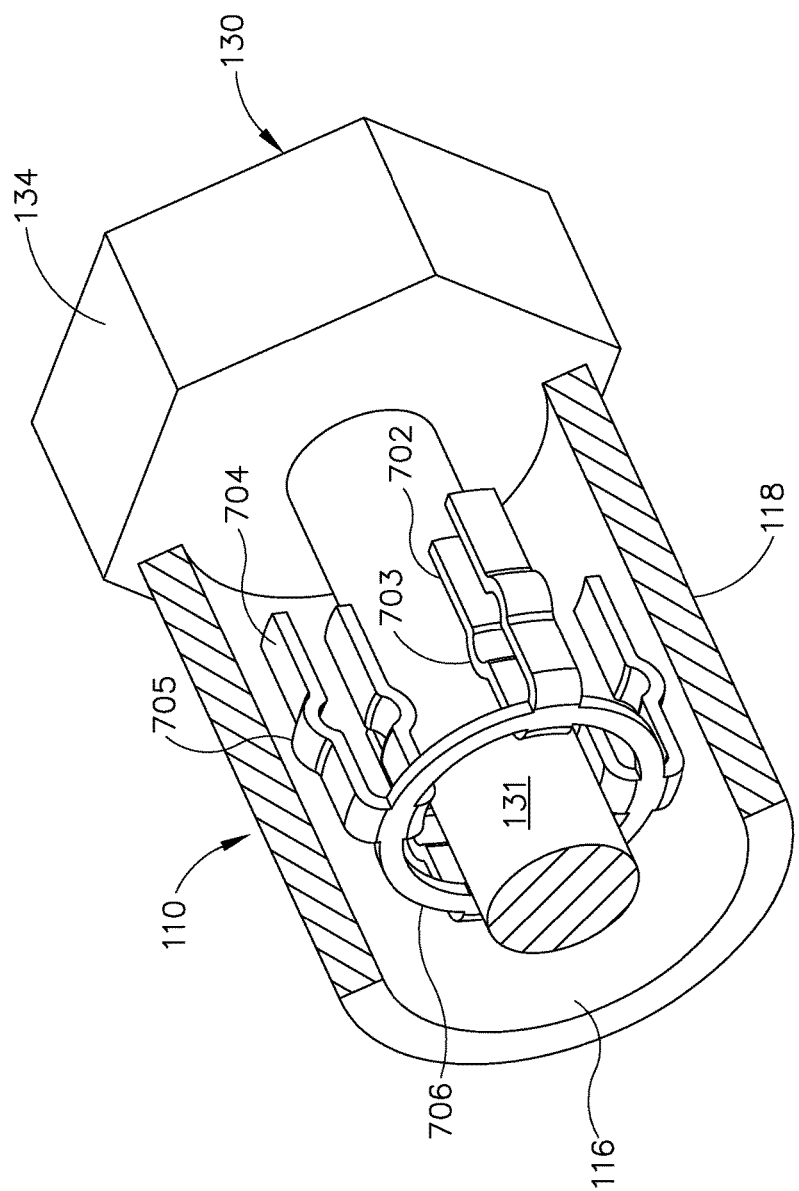
FIG. 19 depicts a partial perspective view of the assembly of FIG. 18, with a transducer element in cross-section.

FIG. 17 shows an exemplary electrical contact member (700) in a flat state. Contact member (700) of this example comprises a first series of arms (702), a second series of arms (704), and a band (706) that joins arms (702, 704) together. Band (706) includes several cutouts (708) that facilitate formation of band (706) into an annular configuration as shown in FIGS. 18-19. Contact member (700) may be formed of a copper alloy and/or any other suitable conductive material(s). Contact member (700) may also be formed using a stamping process and/or any other suitable process (es). Various suitable materials and processes that may be used to form contact member (700) will be apparent to those of ordinary skill in the art in view of the teachings herein.

As shown in FIGS. 18-19, contact member (700) may be deformed from the flat state shown in FIG. 17 into a state where band (706) forms an annular shape and opposing pairs of arms (702, 704) are bent to form a series of "U" shapes. In particular, arms (702) are bent to bear resiliently inwardly on shank (131) of bolt (130) while arms (704) are bent to bear resiliently outwardly on inner diameter surface (116) of transducer element (110). Because contact member (700) is formed of a conductive material, contact member (700) thus provides electrical continuity between bolt (130) and inner diameter surface (116) of transducer element (110). In some instances, each arm (702) includes a protrusion (703) and each arm (704) includes a protrusion (705), as shown in FIG. 19. Protrusions (703, 705) may be configured to provide a reduced size point of contact between arm (702) and shank (131), and between arm (704) and inner diameter surface (116). For instance, this may assist in localizing the contact to locations that correspond to a node associated with resonant ultrasonic vibrations communicated through acoustic assembly (100). Other variations of contact member (700) will be apparent to those of ordinary skill in the art in view of the teachings herein.

2. Exemplary Conductor with Resiliently Biased Curved Arms

Figure 20:
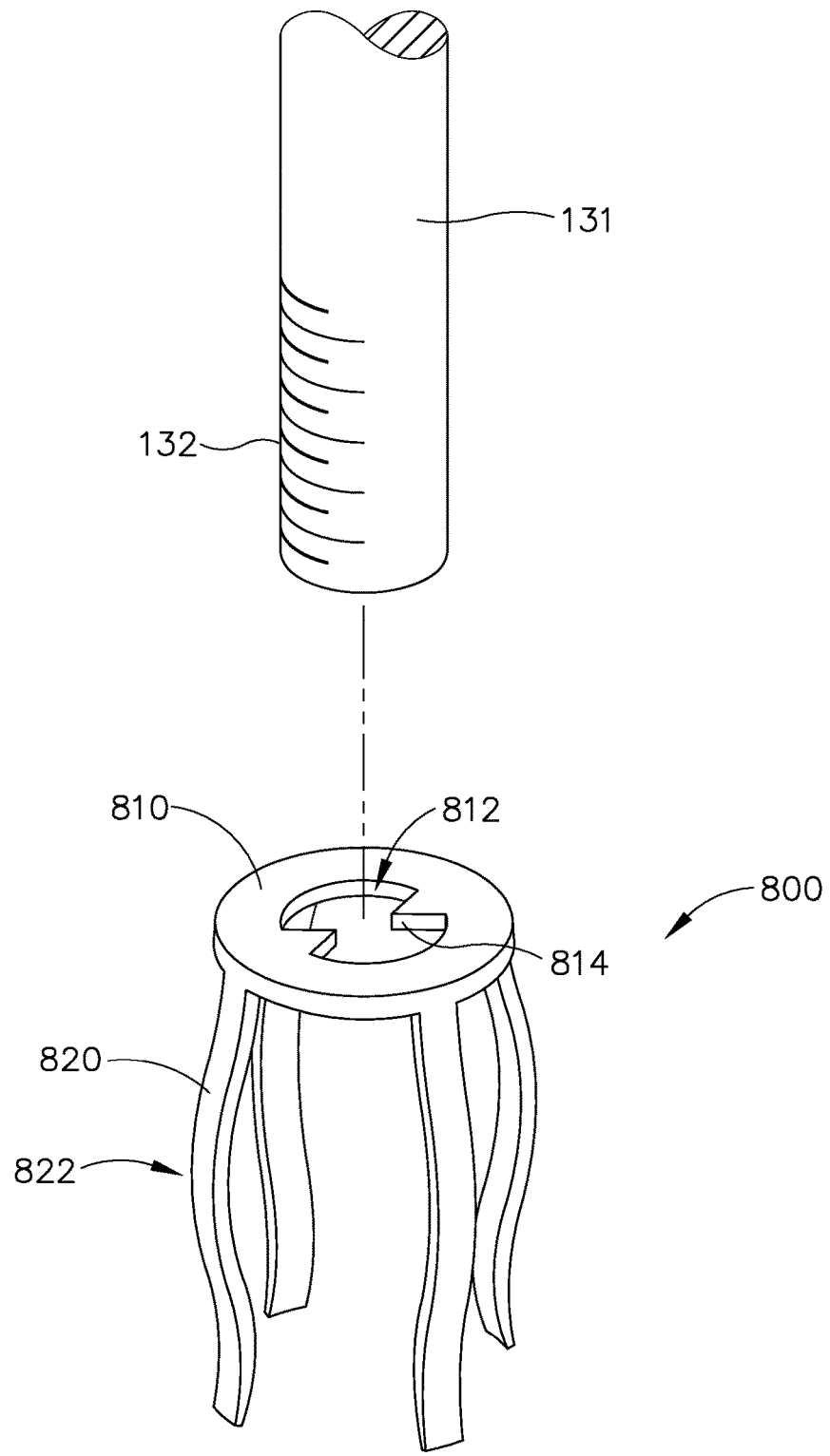
FIG. 20 depicts an exploded perspective view of an exemplary conductor and bolt assembly.
Figure 21:
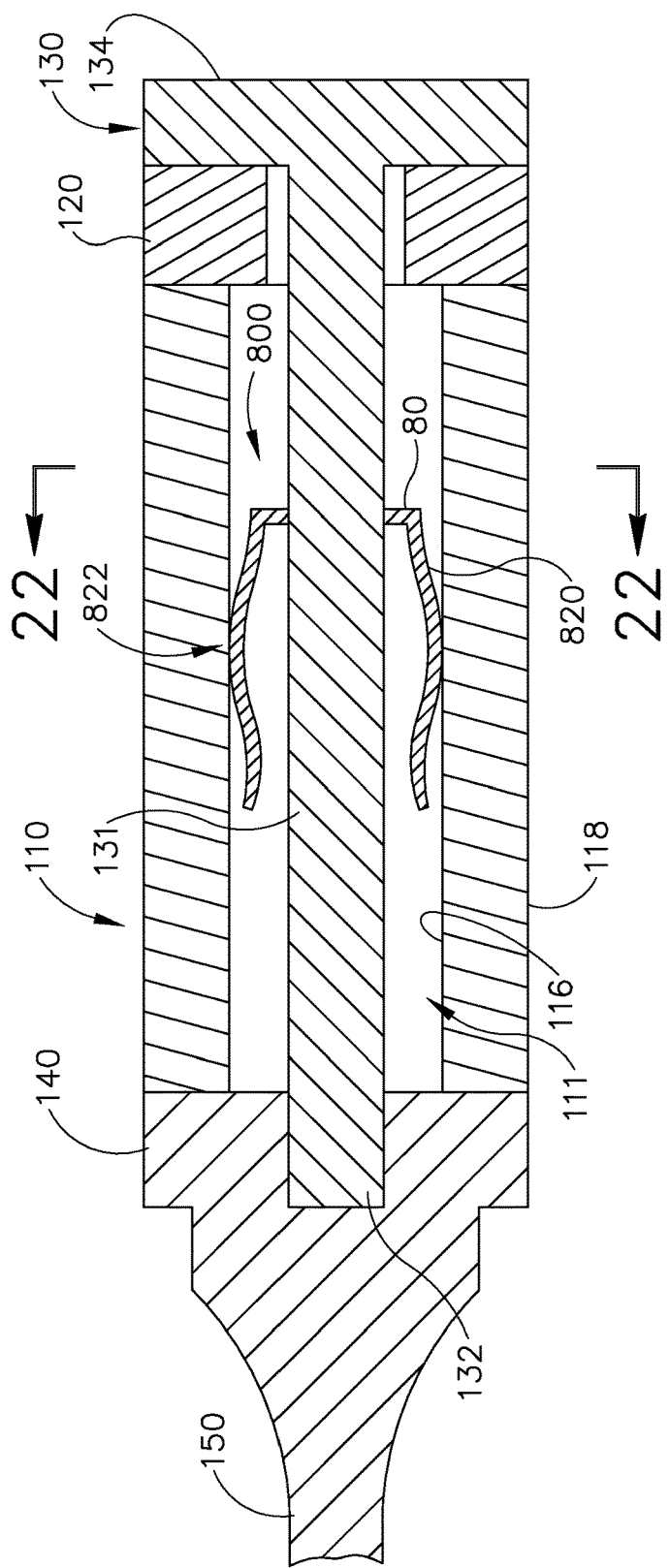
FIG. 21 depicts a cross-sectional side view of an exemplary acoustic assembly incorporating the conductor and bolt assembly of FIG. 20.
Figure 22:
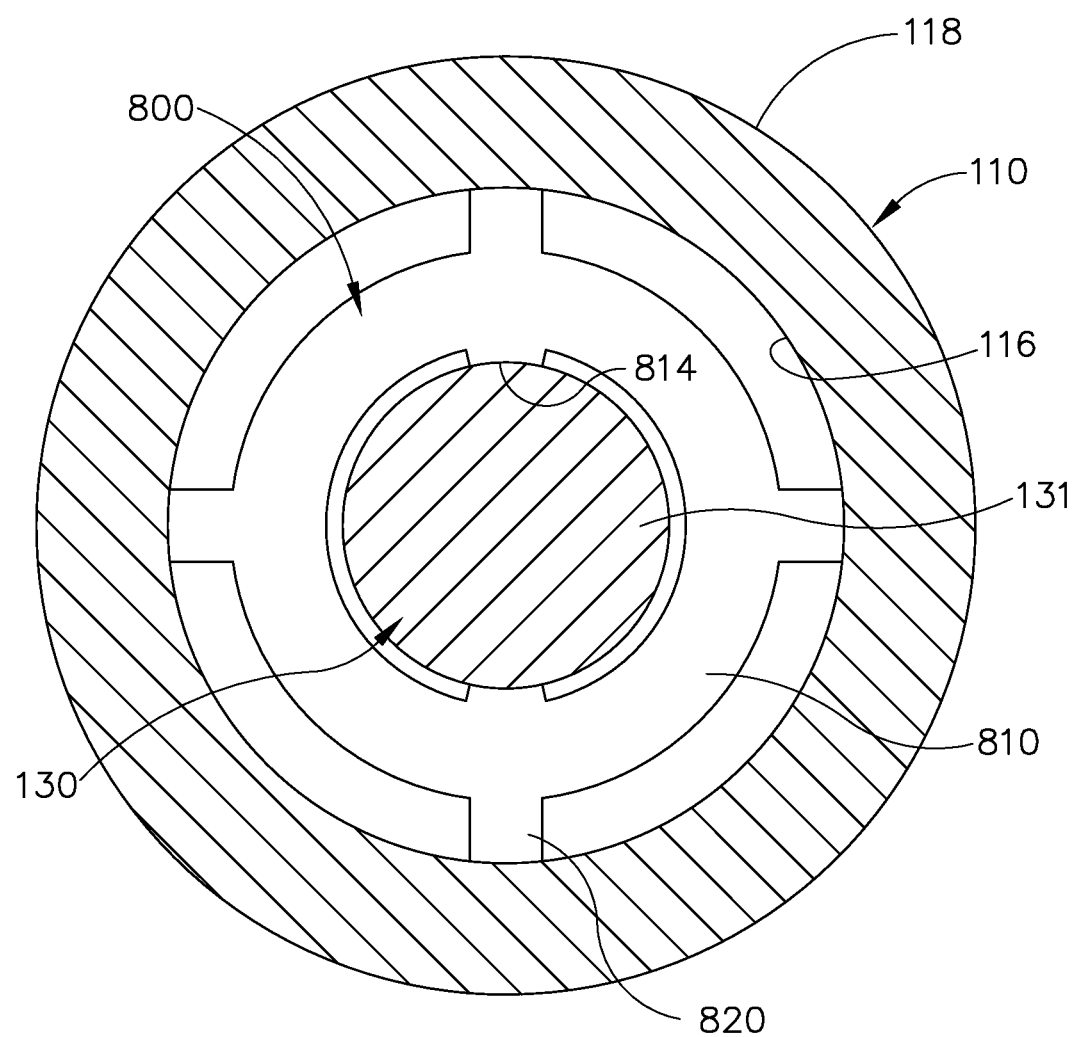
FIG. 22 depicts a cross-sectional end view of the assembly of FIG. 21.

FIGS. 20-22 show another exemplary electrical contact member (800). Contact member (800) of this example comprises a hub member (810) having a plurality of arms (820) extending therefrom. Contact member (800) may be formed of a copper alloy and/or any other suitable conductive material(s). Contact member (800) may also be formed using a stamping process and/or any other suitable process (es). Various suitable materials and processes that may be used to form contact member (800) will be apparent to those of ordinary skill in the art in view of the teachings herein. Hub member (810) defines an opening (812) that includes a pair of inwardly directed projections (814). Opening (812) is configured to receive shank (131) of bolt (130). As best seen in FIG. 22, projections (814) deformingly engage shank (131). Even with such deformation, the pointed configuration of projections (814) provides engagement that substantially maintains the longitudinal position of contact member (800) along shank (131). For instance, projections (814) may be configured to "bite into" shank (131). In some other versions, projections (814) are omitted and opening (812) instead defines a threading that complements the threading of distal end (132) of shank (131). Contact member (800) may thus be threaded on to shank (131) like a nut. Other suitable kinds of relationships between contact member (800) and shank (131) will be apparent to those of ordinary skill in the art in view of the teachings herein. It should be understood that contact member (800) of the present example is electrically coupled with bolt (130) due to contact between hub member (810) and shank (131).

Each arm (820) includes an outwardly oriented curved section (822). Curved sections (822) are configured to bear outwardly on inner diameter surface (116) of transducer element (110) when contact member (800) is disposed in bore (111) of transducer element (110), as shown in FIGS. 21-22. Because contact member (800) is formed of a conductive material, contact member (800) thus provides electrical continuity between bolt (130) and inner diameter surface (116) of transducer element (110). In the present example, curved sections (822) are configured such that the regions of arms (820) that contact inner diameter surface (116) are centered at locations that correspond to a node associated with resonant ultrasonic vibrations communicated through acoustic assembly (100). Other variations of contact member (800) will be apparent to those of ordinary skill in the art in view of the teachings herein. By way of example only, while four arms (820) are shown, any other suitable number of arms (820) may be provided.

3. Exemplary Conductor Pair with Resiliently Biased Curved Arms

Figure 23:
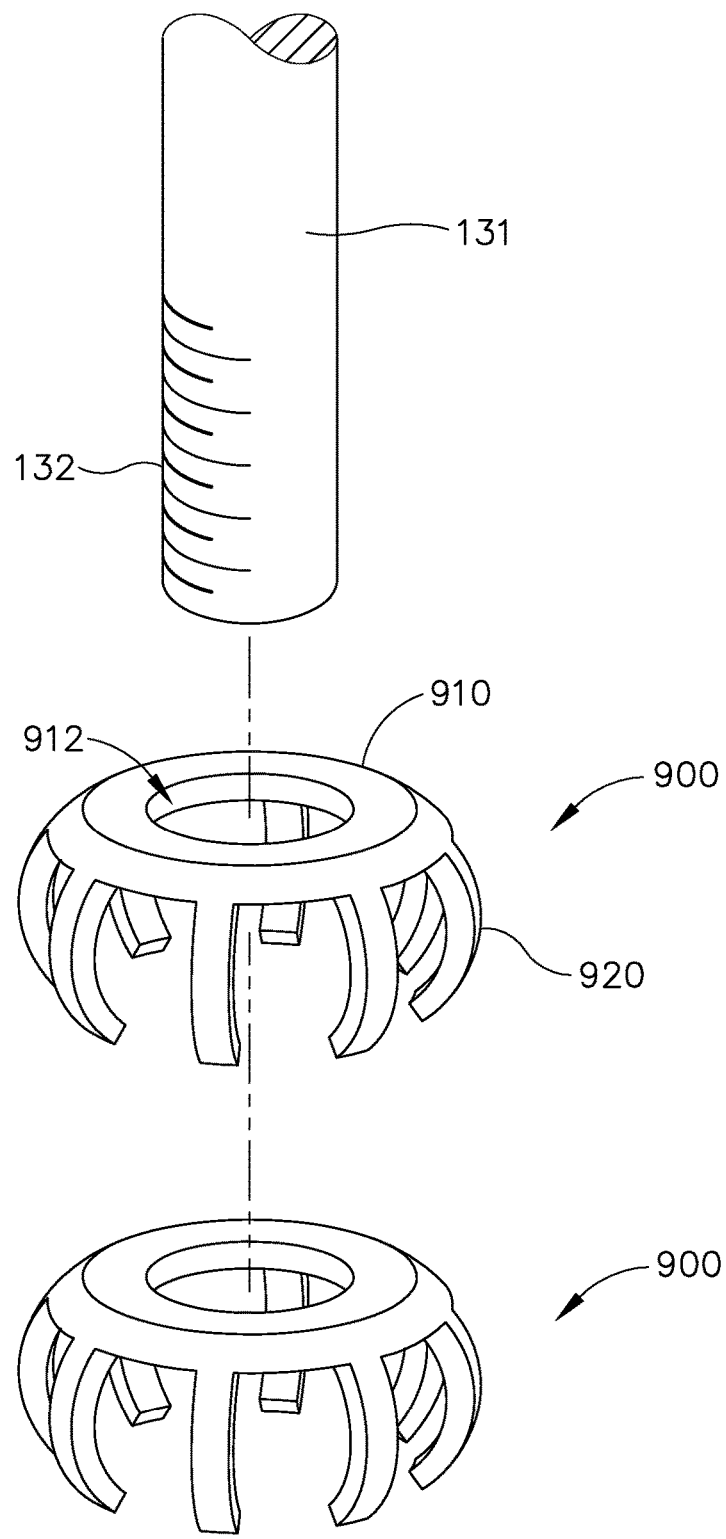
FIG. 23 depicts an exploded perspective view of an exemplary conductor pair and bolt assembly.
Figure 24:
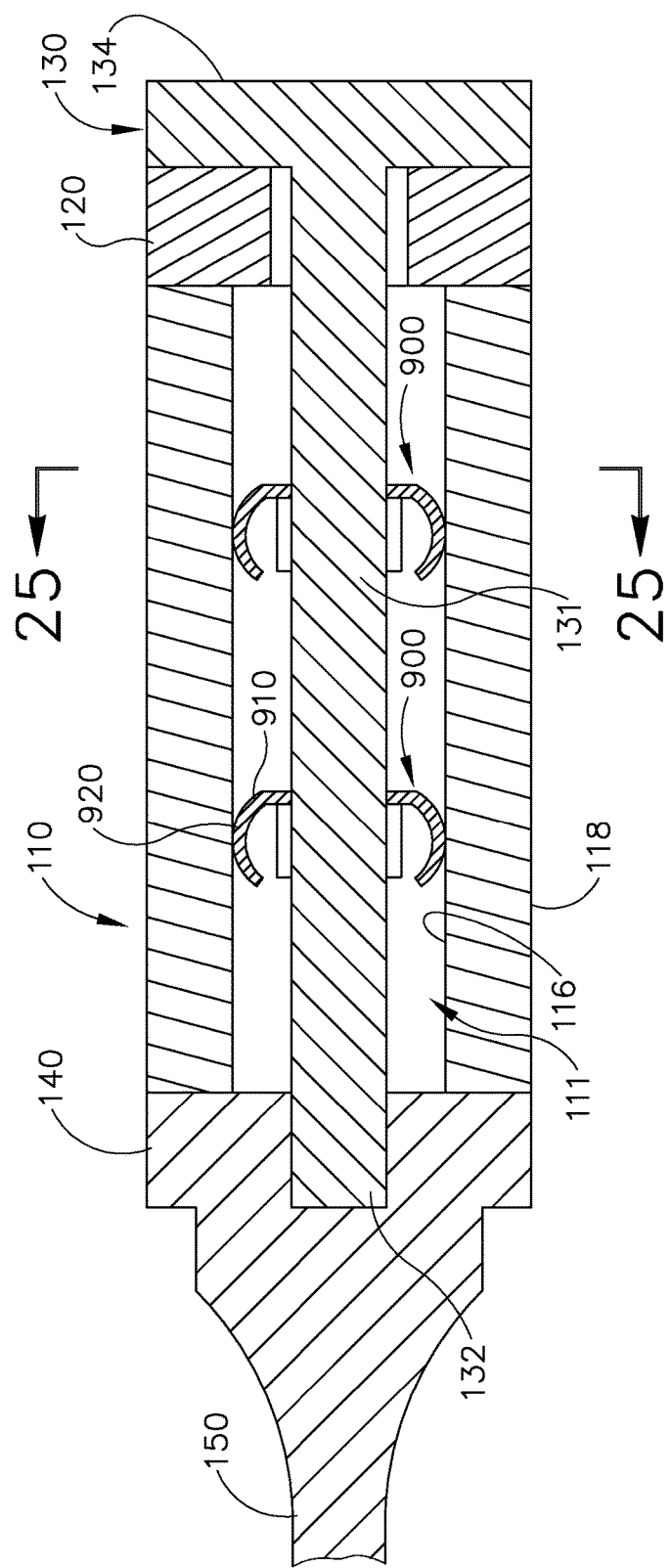
FIG. 24 depicts a cross-sectional side view of an exemplary acoustic assembly incorporating the conductor and bolt assembly of FIG. 23.
Figure 25:
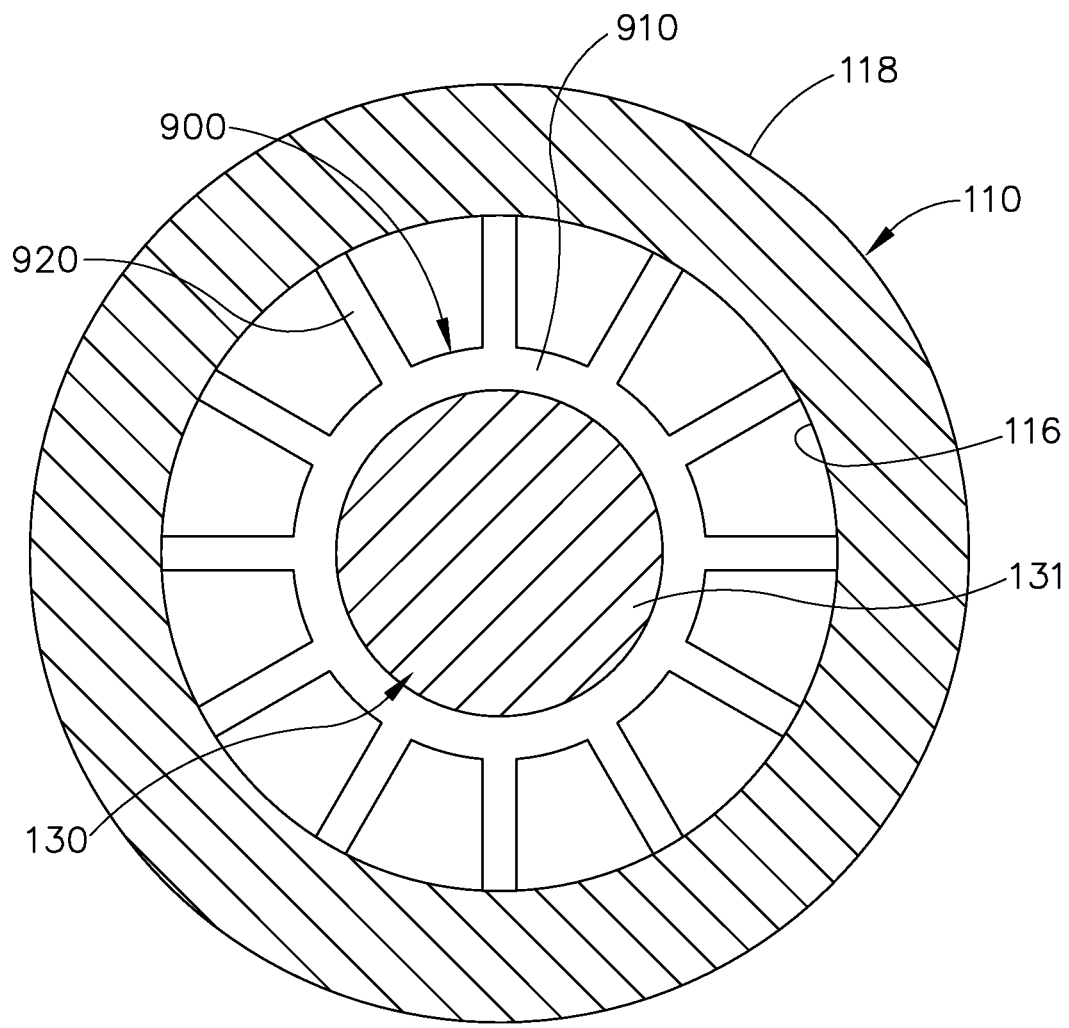
FIG. 25 depicts a cross-sectional end view of the assembly of FIG. 24.

FIGS. 23-25 show a pair of exemplary alternative electrical contact members (900). While two contact members (900) are shown in this example, it should be understood that any other suitable number of contact members (900) may be used. Each contact member (900) of this example comprises a hub member (910) having a plurality of arms (920) extending therefrom. Contact member (900) may be formed of a copper alloy and/or any other suitable conductive material(s). Contact member (900) may also be formed using a stamping process and/or any other suitable process(es). Various suitable materials and processes that may be used to form contact member (900) will be apparent to those of ordinary skill in the art in view of the teachings herein. Hub member (910) defines an opening (912) that is configured to receive shank (131) of bolt (130). Opening (912) is sized and configured such that contact member (900) may be threaded on to shank (131) like a nut. Other suitable kinds of relationships between contact member (900) and shank (131) will be apparent to those of ordinary skill in the art in view of the teachings herein. It should be understood that contact member (900) of the present example is electrically coupled with bolt (130) due to contact between hub member (910) and shank (131).

Each arm (920) has an outwardly curved oriented curve. Arms (920) are configured to bear outwardly on inner diameter surface (116) of transducer element (110) when contact member (900) is disposed in bore (111) of transducer element (110), as shown in FIGS. 24-25. Because contact member (900) is formed of a conductive material, contact member (900) thus provides electrical continuity between bolt (130) and inner diameter surface (116) of transducer element (110). Arms (920) are configured such that the regions of arms (920) that contact inner diameter surface (116) are centered at locations that correspond to a node associated with resonant ultrasonic vibrations communicated through acoustic assembly (100). Other variations of contact member (900) will be apparent to those of ordinary skill in the art in view of the teachings herein.

4. Exemplary Conductor with Arms on Living Hinges

Figure 26:
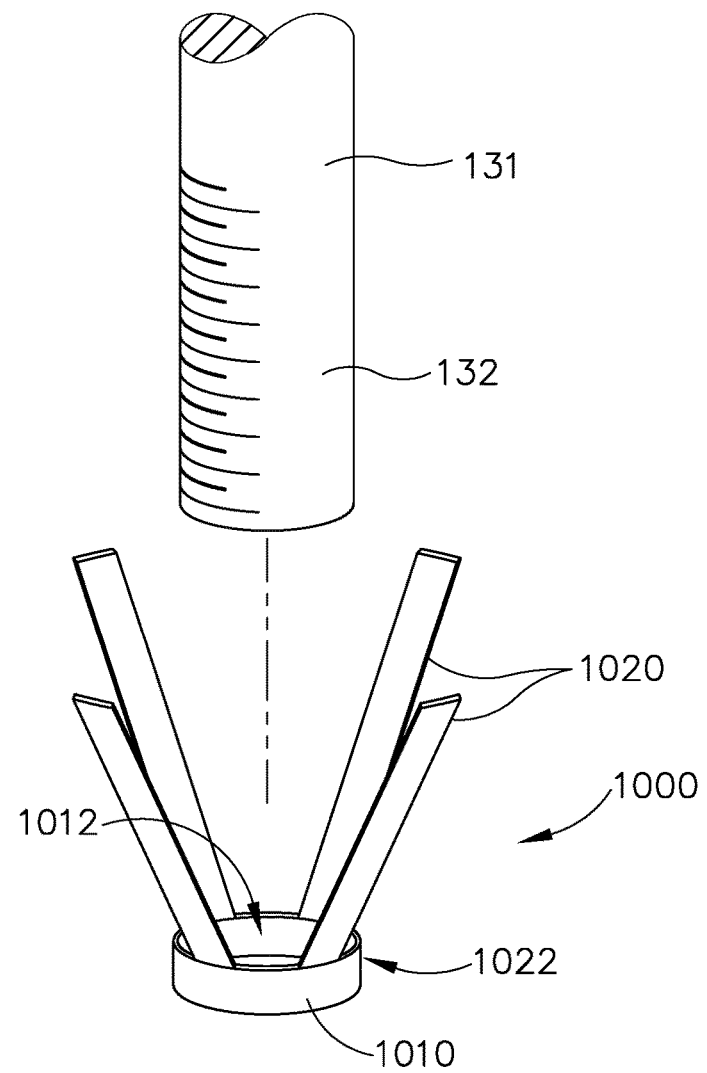
FIG. 26 depicts an exploded perspective view of another exemplary conductor and bolt assembly.
Figure 27:
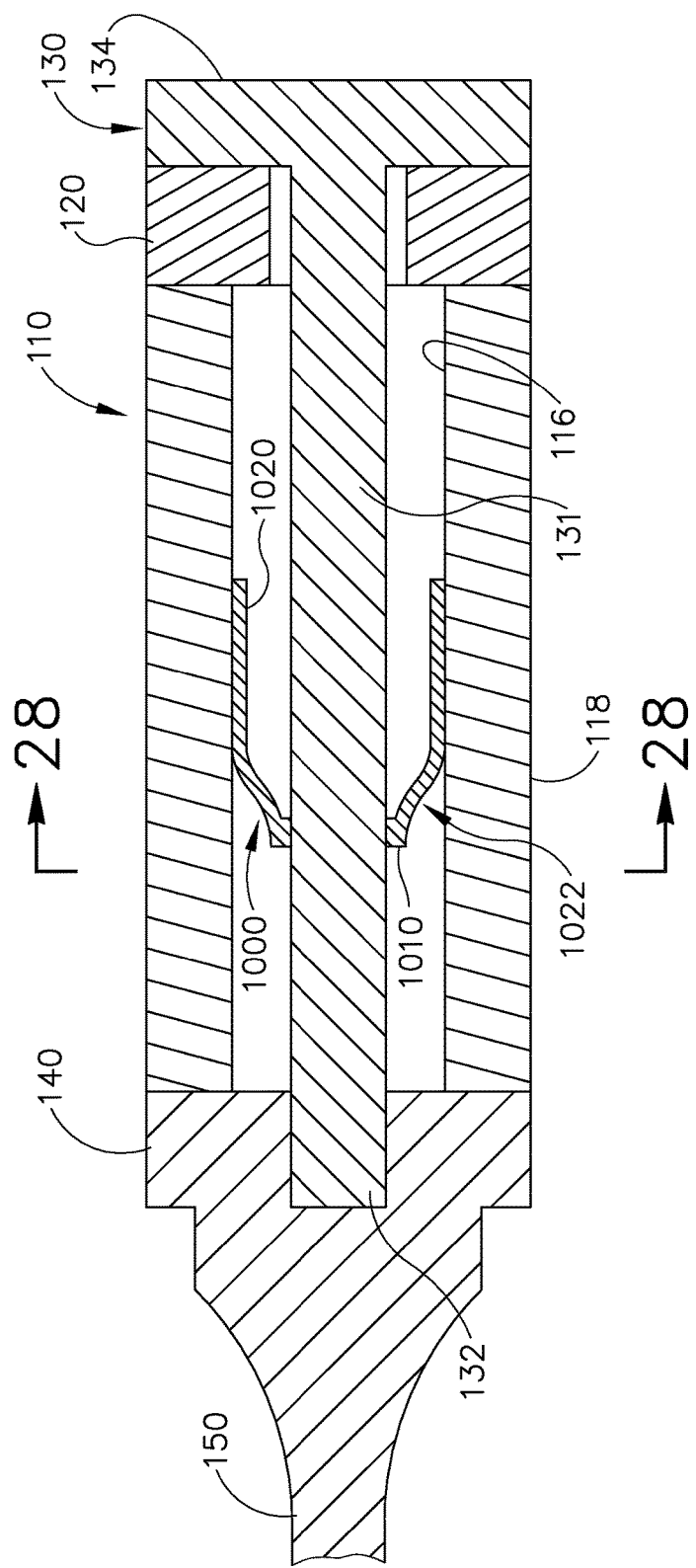
FIG. 27 depicts a cross-sectional side view of an exemplary acoustic assembly incorporating the conductor and bolt assembly of FIG. 26.
Figure 28:
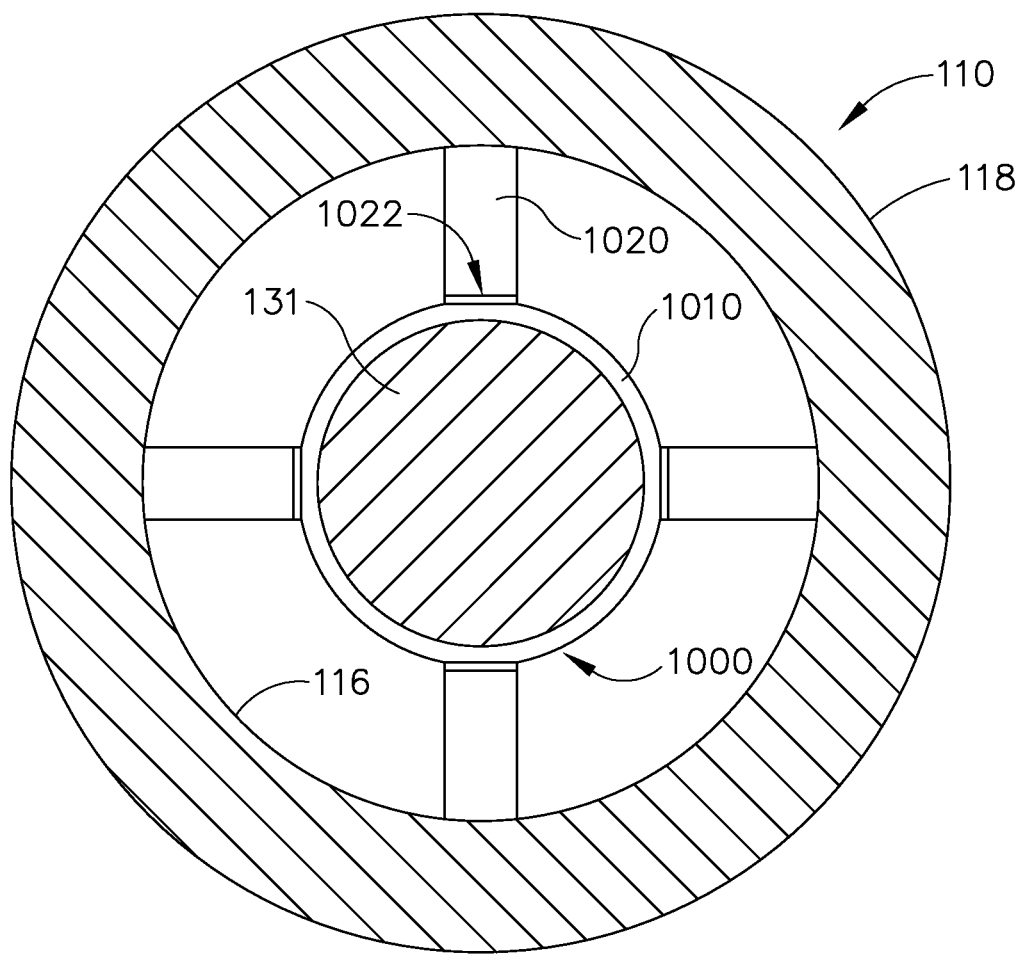
FIG. 28 depicts a cross-sectional end view of the assembly of FIG. 27.

FIGS. 26-28 show another exemplary electrical contact member (1000). Contact member (1000) of this example comprises a hub member (1010) having a plurality of arms (1020) extending therefrom. Contact member (1000) may be formed of a copper alloy and/or any other suitable conductive material(s). Contact member (1000) may also be formed using a stamping process and/or any other suitable process(es). Various suitable materials and processes that may be used to form contact member (1000) will be apparent to those of ordinary skill in the art in view of the teachings herein. Hub member (1010) defines an opening (1012) that is configured to receive shank (131) of bolt (130). Opening (1012) is sized and configured such that contact member (1000) may be threaded on to shank (131) like a nut. In some other versions, hub member (1010) is welded to or otherwise secured to shank (131) at a location proximal to the threading of distal end (132) of shank (131). Other suitable kinds of relationships between contact member (1000) and shank (131) will be apparent to those of ordinary skill in the art in view of the teachings herein. It should be understood that contact member (1000) of the present example is electrically coupled with bolt (130) due to contact between hub member (1010) and shank (131).

Arms (1020) are coupled with hub member (1010) via living hinges (1022). The resilience of arms (1020) and the resilience of living hinges (1022) cooperate to resiliently bias arms (1020) to an outwardly splayed configuration as shown in FIG. 26. Arms (1020) are thus configured to bear outwardly on inner diameter surface (116) of transducer element (110) when contact member (1000) is disposed in bore (111) of transducer element (110), as shown in FIGS. 27-28. Because contact member (1000) is formed of a conductive material, contact member (1000) thus provides electrical continuity between bolt (130) and inner diameter surface (116) of transducer element (110). Arms (1020) are configured such that the regions of arms (1020) that contact inner diameter surface (116) are centered at locations that correspond to a node associated with resonant ultrasonic vibrations communicated through acoustic assembly (100). Other variations of contact member (1000) will be apparent to those of ordinary skill in the art in view of the teachings herein.

5. Exemplary Conductor with Resiliently Biased Wings

Figure 29:
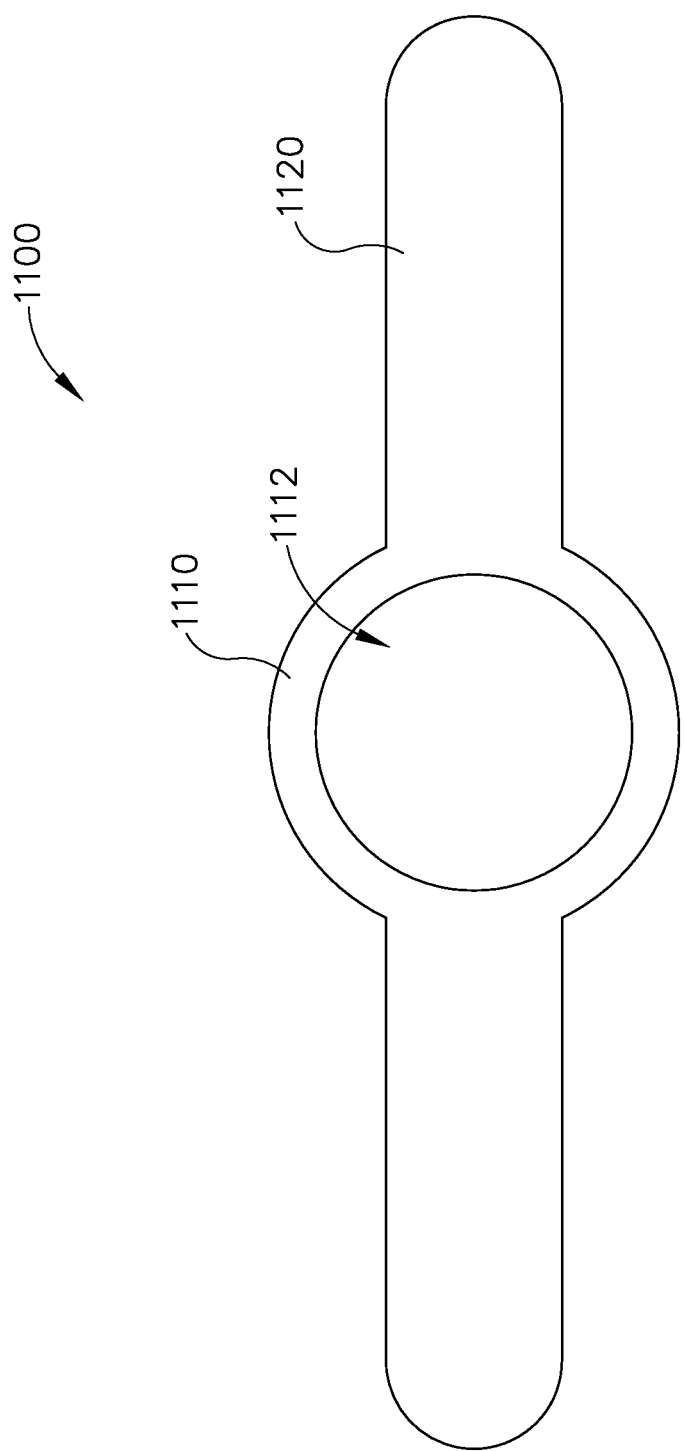
FIG. 29 depicts a top plan view of another exemplary conductor.
Figure 30:
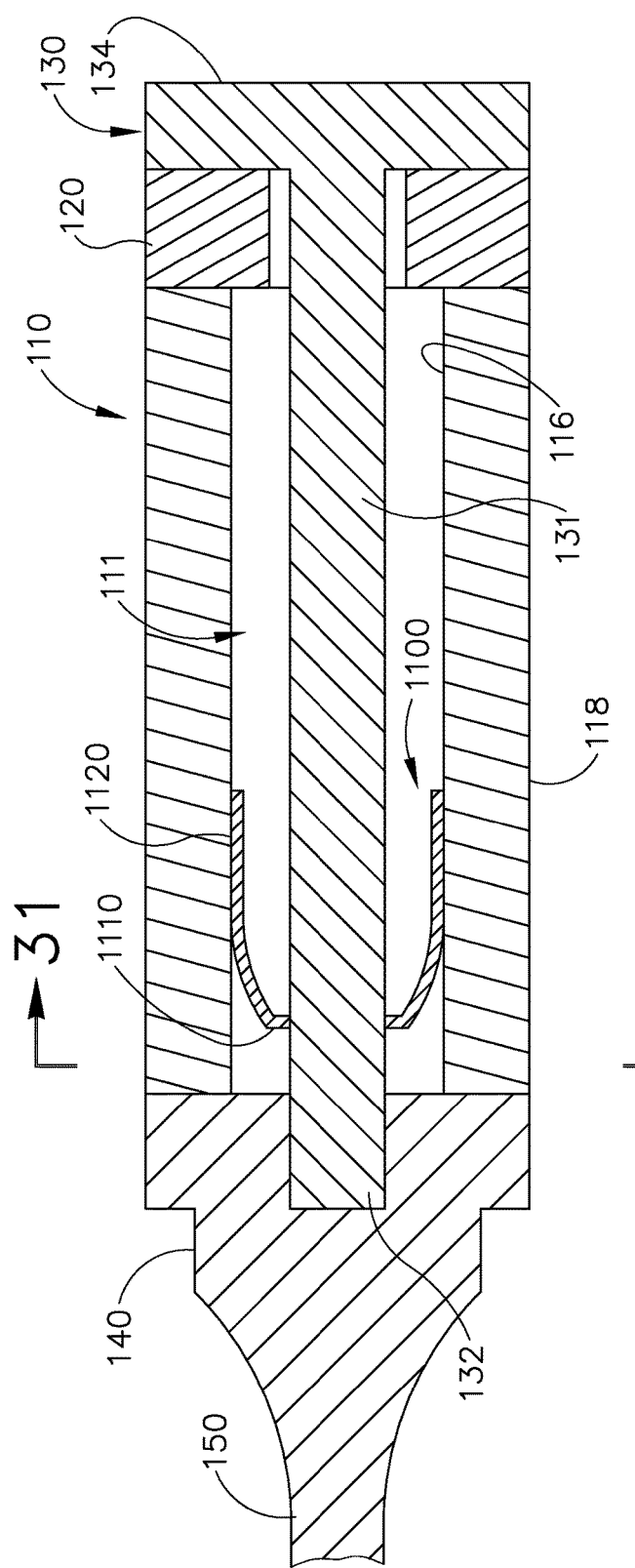
FIG. 30 depicts a cross-sectional side view of an exemplary acoustic assembly incorporating the conductor of FIG. 29.
Figure 31:
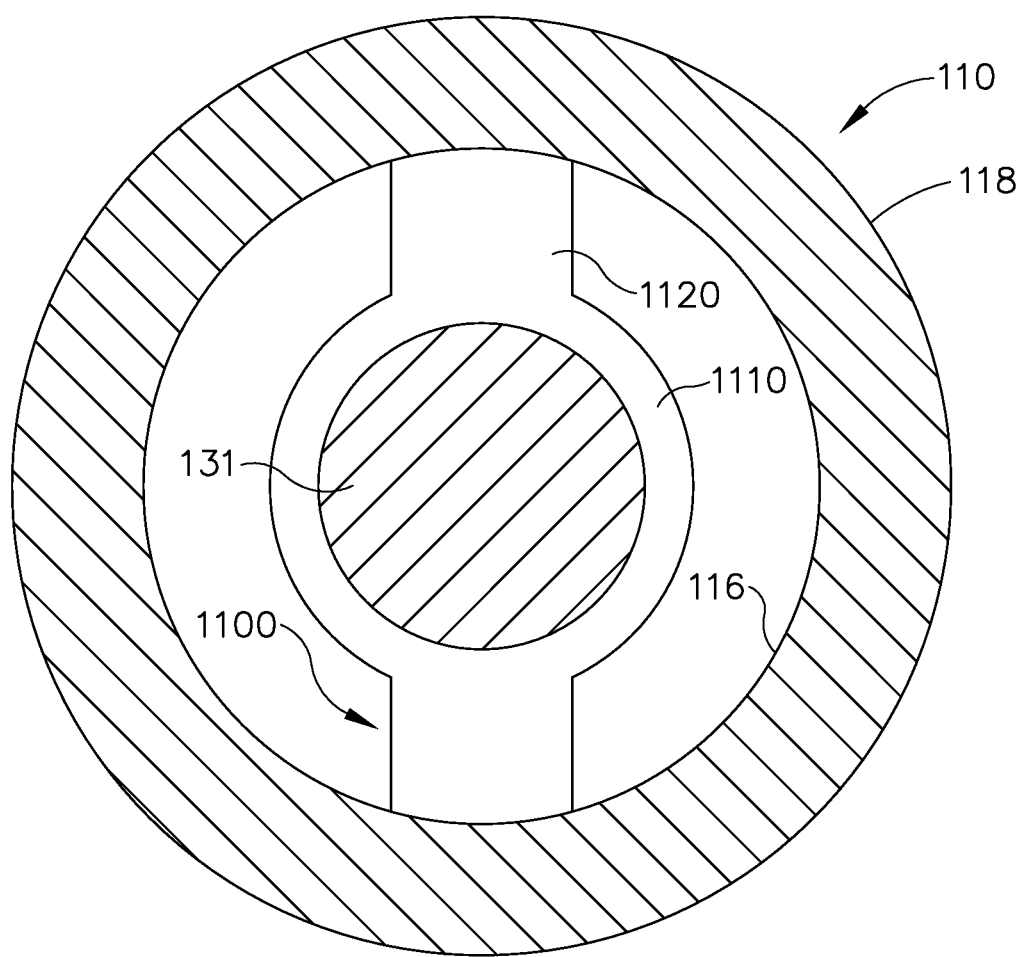
FIG. 31 depicts a cross-sectional end view of the assembly of FIG. 30.

FIGS. 29-31 show another exemplary electrical contact member (1100). Contact member (1100) of this example comprises a hub member (1110) having a pair of arms or wings (1120) outwardly therefrom. Contact member (1100) may be formed of a copper alloy and/or any other suitable conductive material(s). Contact member (1100) may also be formed using a stamping process and/or any other suitable process(es). Various suitable materials and processes that may be used to form contact member (1100) will be apparent to those of ordinary skill in the art in view of the teachings herein. Hub member (1110) defines an opening (1112) that is configured to receive shank (131) of bolt (130). Opening (1112) is sized and configured such that contact member (1100) may be threaded on to shank (131) like a nut. In some other versions, hub member (1110) is welded to or otherwise secured to shank (131) at a location proximal to the threading of distal end (132) of shank (131). Other suitable kinds of relationships between contact member (1100) and shank (131) will be apparent to those of ordinary skill in the art in view of the teachings herein. It should be understood that contact member (1100) of the present example is electrically coupled with bolt (130) due to contact between hub member (1110) and shank (131).

Wings (1120) are configured as unitary features of hub member (1110). The resilience of wings (1120) resiliently biases wings (1120) to an outwardly extending flat configuration as shown in FIG. 29. In other words, wins (1120) are resiliently biased to extend along a common plane with hub member (1110). Wings (1120) are thus configured to bear outwardly on inner diameter surface (116) of transducer element (110) when contact member (1100) is disposed in bore (111) of transducer element (110), as shown in FIGS. 30-31. Because contact member (1100) is formed of a conductive material, contact member (1100) thus provides electrical continuity between bolt (130) and inner diameter surface (116) of transducer element (110). Wings (1120) are configured such that the regions of wings (1120) that contact inner diameter surface (116) are centered at locations that correspond to a node associated with resonant ultrasonic vibrations communicated through acoustic assembly (100). Other variations of contact member (1100) will be apparent to those of ordinary skill in the art in view of the teachings herein.

6. Exemplary Rolled Conductor

Figure 32:
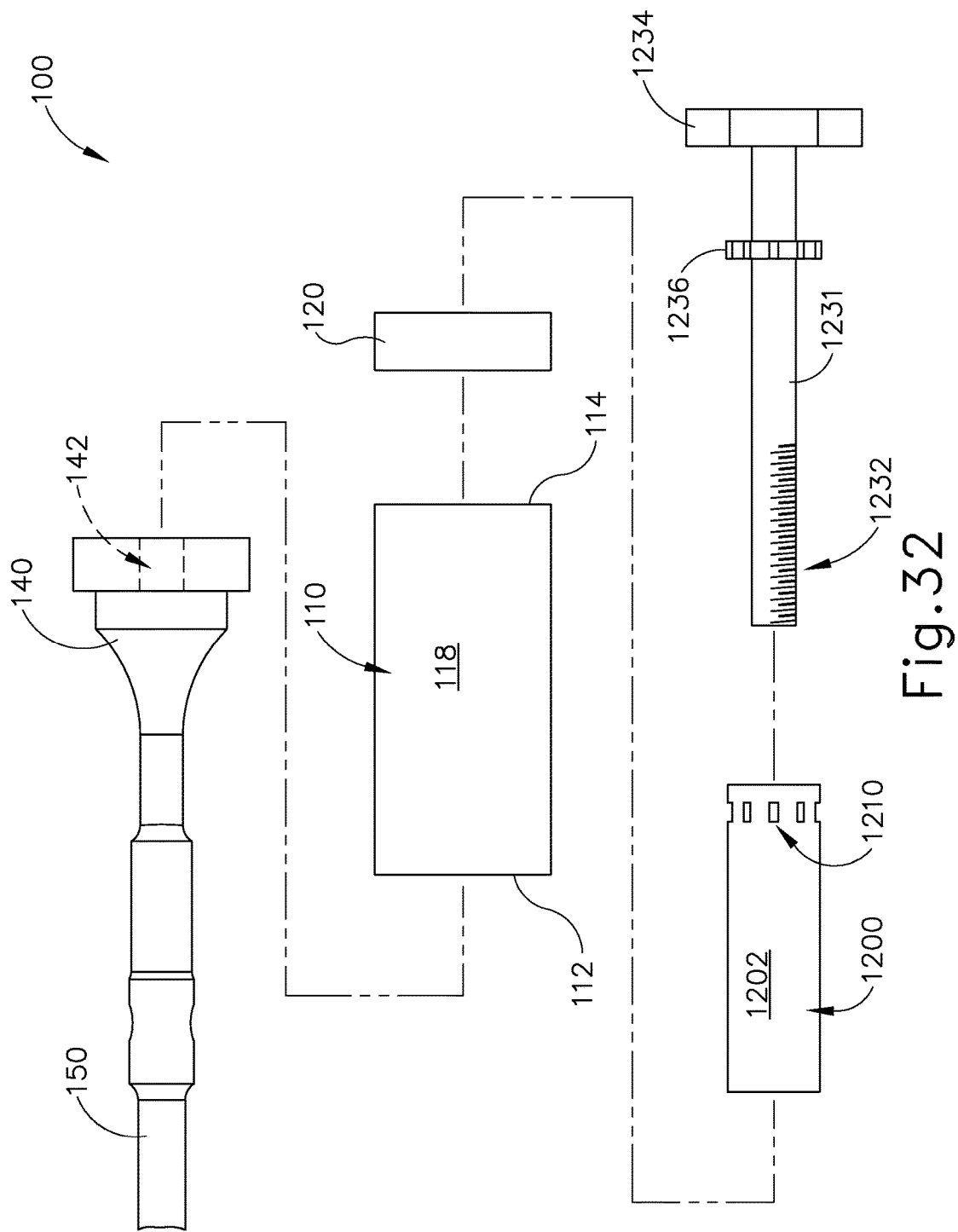
FIG. 32 depicts an exploded view of another exemplary acoustic assembly.
Figure 33:
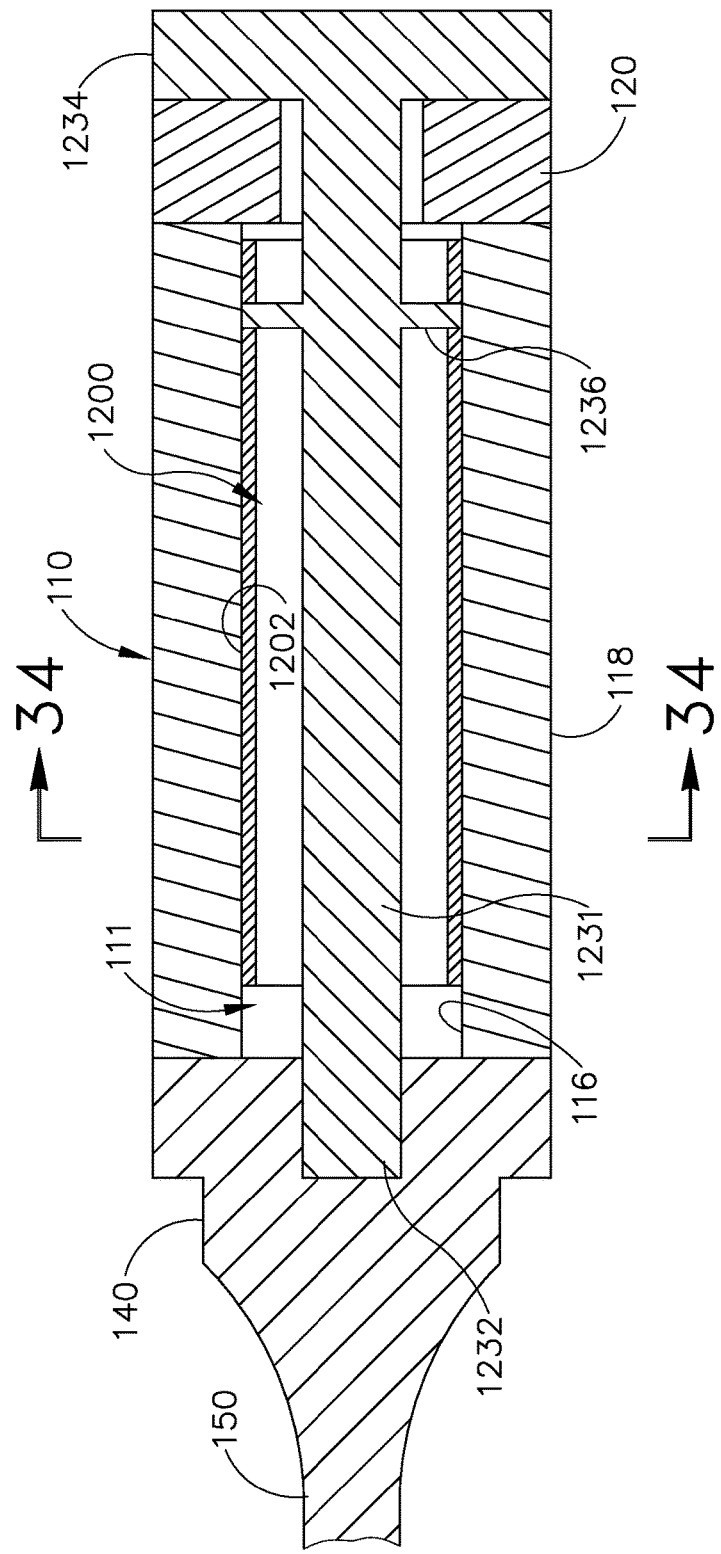
FIG. 33 depicts a cross-sectional side view of the assembly of FIG. 32.
Figure 34:
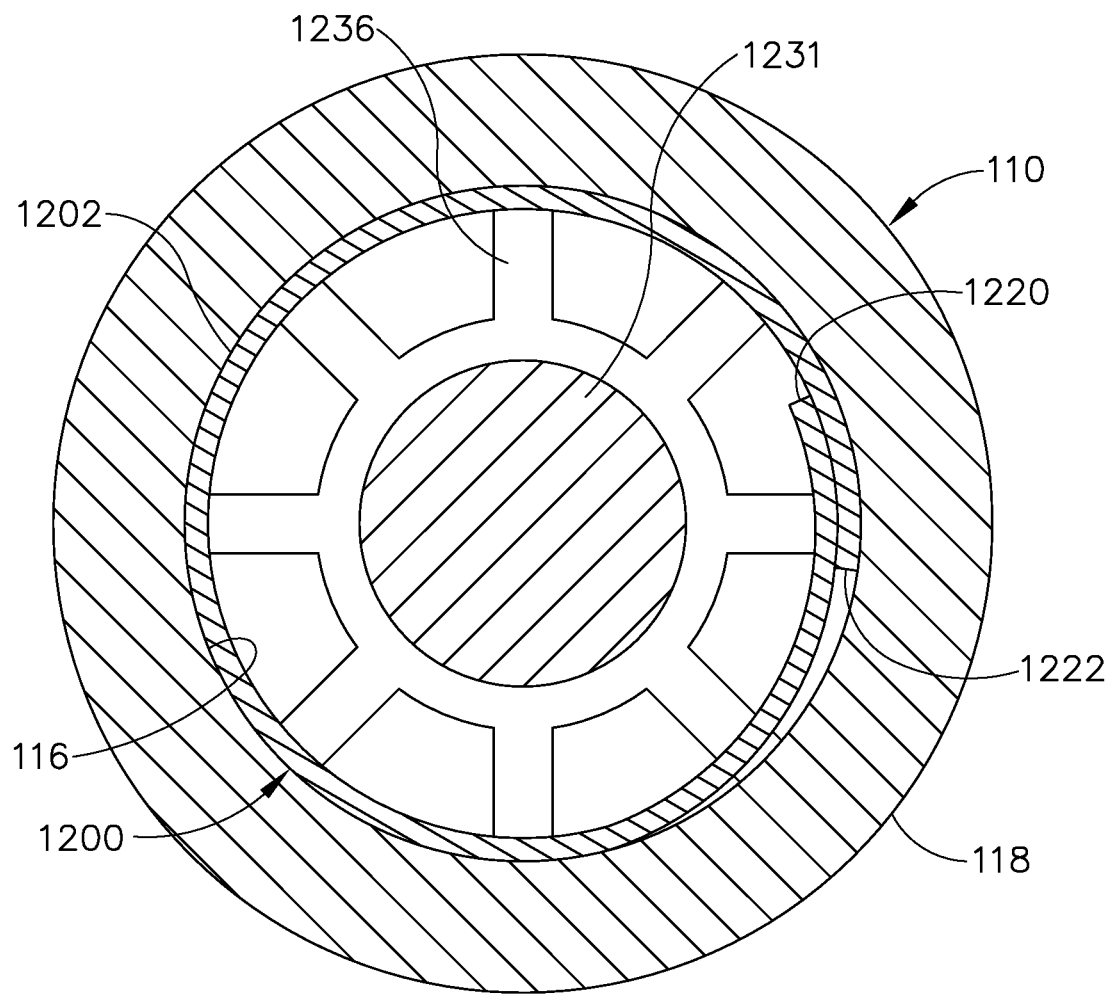
FIG. 34 depicts a cross-sectional view of the assembly of FIG. 32, taken along line 34-34 of FIG. 33.

FIGS. 32-34 show another exemplary electrical contact member (1200), which is configured for use with an exemplary alternative bolt (1230). Bolt (1230) is substantially identical to bolt (130) described above, except that bolt (1230) of this example includes an angular array of projections (1236) extending radially outwardly from shank (1231). Bolt (1231) also includes a threaded distal section (1230) and a head (1234), just like bolt (130). Contact member (1200) of this example comprises a sheet that is rolled into a cylindraceous shape, with a pair of opposing outer edges (1220, 1222) being positioned at an overlap as shown in FIG. 34. Contact member (1200) may be formed of a copper alloy and/or any other suitable conductive material(s). Contact member (1200) may also be formed using a stamping process and/or any other suitable process (es). Various suitable materials and processes that may be used to form contact member (1200) will be apparent to those of ordinary skill in the art in view of the teachings herein. Contact member (1200) of the present example defines an array of openings (1210). Openings (1210) are configured to receive projections (1236) of bolt (1230). It should be understood that contact member (1200) of the present example is electrically coupled with bolt (1230) due to contact between contact member (1200) with projections (1236) at openings (1210).

Contact member (1200) is resiliently biased to assume a substantially flat, unrolled configuration, such that contact member (1200) has a resilient bias similar to a torsion spring when contact member (1200) is in a coiled configuration as shown. Thus, an outer surface (1202) of contact member (1200) will resiliently bear outwardly on inner diameter surface (116) of transducer element (110) when contact member (1200) is disposed in bore (111) of transducer element (110), as shown in FIGS. 33-34. Because contact member (1200) is formed of a conductive material, contact member (1200) thus provides electrical continuity between bolt (130) and inner diameter surface (116) of transducer element (110). In some variations, contact member (1200) may be formed of nitinol that is coated with a conductive material (e.g., a copper alloy, etc.). Contact member (1200) may be preformed to have a rolled, cylindraceous configuration that has an effective outer diameter that is greater than the diameter of bore (111). Contact member (1200) may be shrunk to fit in bore (111), then subsequently heated to expand to the larger configuration to thereby bear against inner diameter surface (116). Other variations of contact member (1200) will be apparent to those of ordinary skill in the art in view of the teachings herein.

7. Exemplary Coiled Conductor with Longitudinal Bias

Figure 35A:
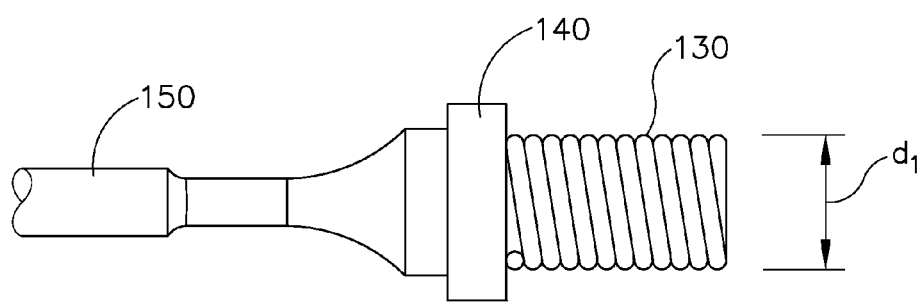
FIG. 35A depicts an exemplary horn with a resilient member in a shortened state.
Figure 35B:
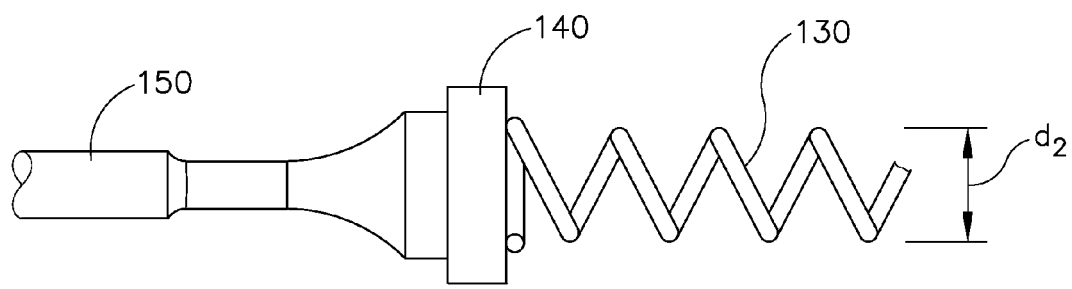
FIG. 35B depicts the horn of FIG. 35A with the resilient member in a stretched state.
Figure 36:
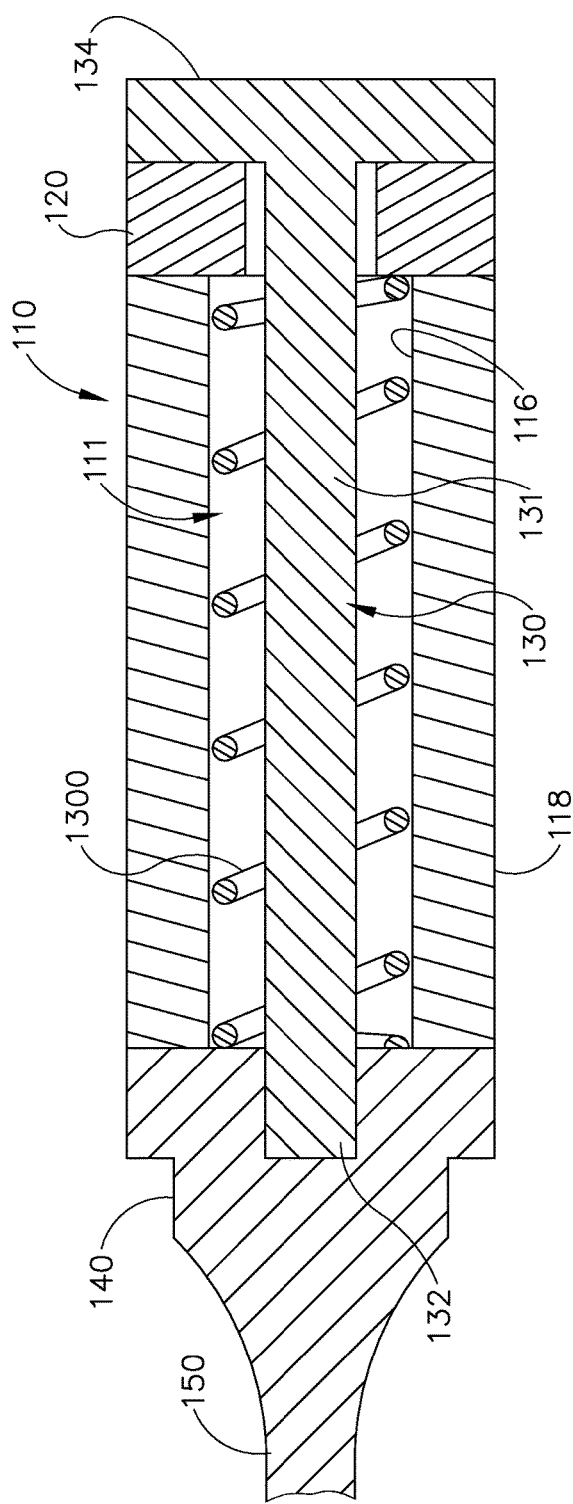
FIG. 36 depicts a cross-sectional side view of an exemplary acoustic assembly incorporating the horn and resilient member of FIG. 35A.

FIGS. 35A-36 show another exemplary electrical contact member (1300). Contact member (1300) of this example is in the form of a coil spring that is secured to the proximal end of horn (140). Contact member (1300) may comprise any suitable conductive material. Various suitable materials and processes that may be used to form contact member (1300) will be apparent to those of ordinary skill in the art in view of the teachings herein. Contact member (1300) is configured to assume a shortened configuration as shown in FIG. 35A; but is deformable to assume a stretched configuration as shown in FIG. 35B. It should be understood that contact member (1300) of the present example is electrically coupled with bolt (130) due to contact between contact member (1300) and horn (140); and due to contact between horn (140) and bolt (130).

As shown in FIG. 35A, contact member (1300) defines a first effective outer diameter ($d_1$) when contact member (1300) is in the shortened configuration. As shown in FIG. 35B, contact member (1300) defines a second effective outer diameter ($d_2$) when contact member (1300) is in the stretched configuration. As can be seen, the second effective outer diameter ($d_2$) is smaller than the first effective outer diameter ($d_1$). The second effective outer diameter ($d_2$) is also smaller than the diameter of bore (111) of transducer element (110); while the first effective outer diameter ($d_1$) is larger than the diameter of bore (111) of transducer element (110). This, when an acoustic assembly (100) having contact member (1300) is being assembled, contact member (1300) may be stretched to the configuration shown in FIG. 35B in order to facilitate fitting of contact member (1300) in bore (111). Once contact member (1300) is suitably positioned in bore (111), contact member (1300) may be released, thereby enabling contact member (1300) to transition back toward the shortened configuration shown in FIG. 35A. As contact member (1300) makes this transition, contact member (1300) eventually makes contact with inner diameter surface (116), thereby placing inner diameter surface (116) in electrical continuity with horn (140) and bolt (130). The final steps of assembling acoustic assembly (100) may then be completed in a normal fashion. Other variations of contact member (1300) will be apparent to those of ordinary skill in the art in view of the teachings herein. By way of example only, in some versions, one end of contact member (1300) may be secured directly to bolt (130), in addition to or in lieu of an end of contact member (1300) being secured to horn (140).

8. Exemplary Transducer Cap with Integral Conductor

Figure 37:
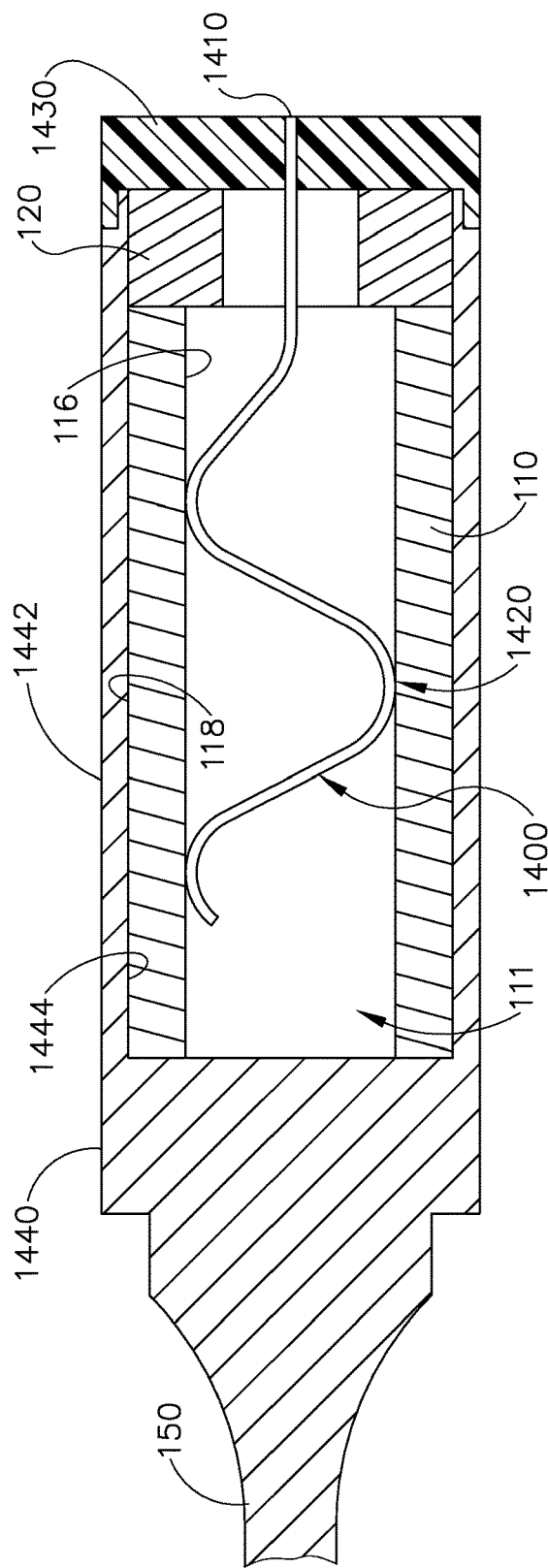
FIG. 37 depicts a cross-sectional side view of another exemplary acoustic assembly.

FIG. 37 shows another exemplary electrical contact member (1300), which is configured for use with an exemplary alternative horn (1440). Horn (1440) is substantially identical to horn (140) described above, except that horn (1440) of this example includes a proximally extending sleeve (1442) that is sized to insertingly receive transducer element (110). Sleeve (1442) also includes a threaded proximal end that is configured to receive a threaded cap (1430), which serves as a substitute for bolt (130). In particular, cap (1430) is configured to compress endmass (120) and transducer element (110) against horn (1440) when cap (1430) is tightened relative to sleeve (1442).

Sleeve (1442) is dimensioned such that the sleeve (1442) contacts outer diameter surface (118) of transducer element (110). Thus, horn (1440) may serve as an electrical path between outer diameter surface (118) and generator (14) (or some other power source). Cap (1430) is formed of an electrically insulative material, such that cap (1430) will not serve as an electrical path to/from horn (1440). Contact member (1400) is fixedly secured to cap (1430), with a proximal end of contact member (1400) being exposed relative to cap (1430). Contact member (1400) comprises an undulating strip that defines a plurality of peaks (1420) on each side of the longitudinal axis defined by transducer element (110). Contact member (1400) contacts inner diameter surface (116) of transducer element (110) at each peak (1420), and resiliently bears against inner diameter surface (116) at these points of contact, such that contact member (1400) acts like a leaf spring. Contact member (1400) may be formed of a copper alloy and/or any other suitable conductive material(s). Contact member (1400) may also be formed using a stamping process and/or any other suitable process(es). Various suitable materials and processes that may be used to form contact member (1400) will be apparent to those of ordinary skill in the art in view of the teachings herein. It should be understood that contact member (1400) may be placed in electrical communication with generator (14) (or some other power source) via the exposed portion of proximal end (1410). Contact member (1400) may thus serve as an electrical path between inner diameter surface (116) and generator (14) (or some other power source).

Figure 38:
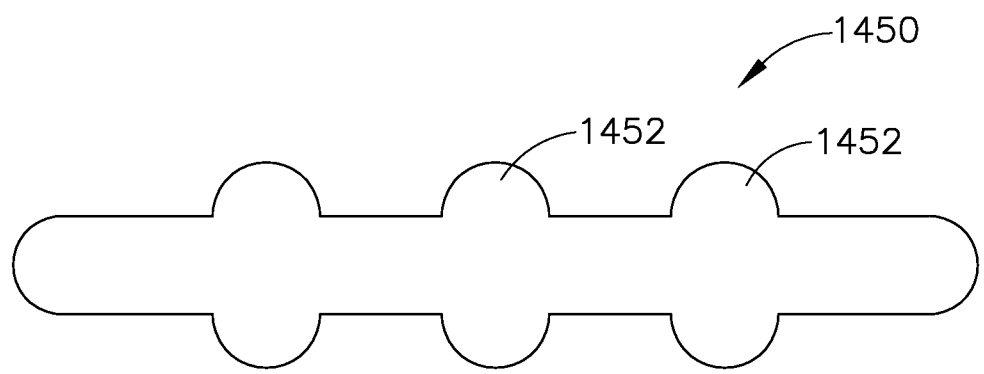
FIG. 38 depicts a top plan view of an exemplary conductor suitable for use in the assembly of FIG. 37.

FIG. 38 shows an exemplary variation of contact member (1400). In particular, FIG. 38 shows a contact member (1450) that includes enlarged regions (1452) that correspond with where peaks (1420) would be located. In other words, contact member (1450) would contact inner diameter surface (116) at enlarged regions (1452). Other variations of contact member (1400, 1450) will be apparent to those of ordinary skill in the art in view of the teachings herein. It should also be understood that horn (1440) and cap (1430) may be varied in numerous ways. By way of example only, sleeve (1442) may be an integral feature of cap (1430) instead of being an integral feature of horn (1440).

9. Exemplary Transducer Bolt with Integral Conductor Arms

Figure 39:
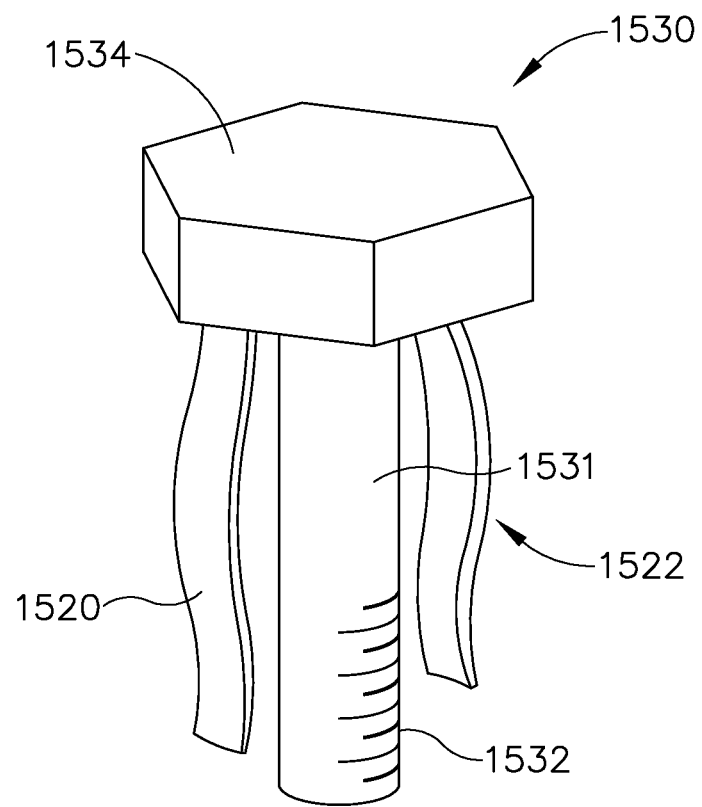
FIG. 39 depicts a perspective view of another exemplary conductor and bolt assembly.
Figure 40:
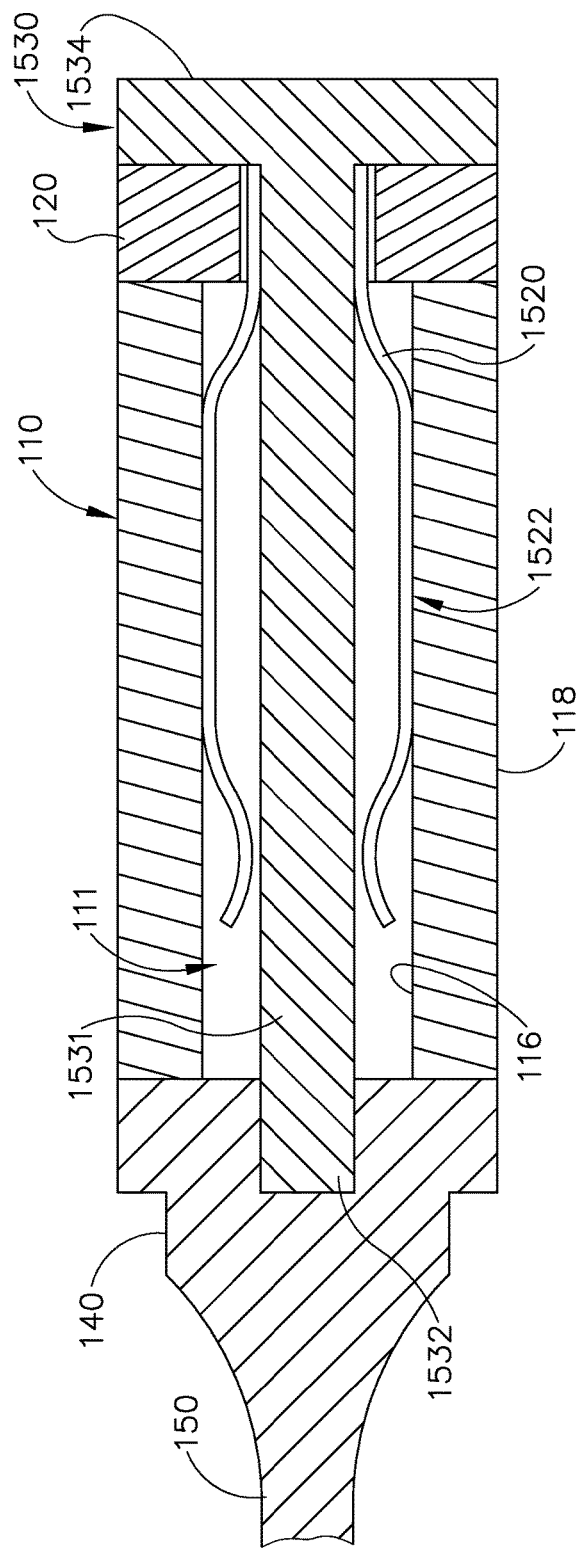
FIG. 40 depicts a cross-sectional side view of an exemplary acoustic assembly incorporating the conductor and bolt assembly of FIG. 39.

FIGS. 39-40 show another exemplary variation of bolt (130). In particular, FIGS. 39-40 show an exemplary bolt (1530) that includes a shank (1531) with a threaded distal end (1532), a head (1534), and a pair of resilient arms (1520) that are integral with head (1534). Each arm (1520) includes an outwardly oriented curved section (1522). Curved sections (1522) are configured to bear outwardly on inner diameter surface (116) of transducer element (110) when bolt (1530) is disposed in bore (111) of transducer element (110), as shown in FIG. 40, such that arms (1520) behave like outwardly biased leaf springs. Arms (1520) are formed of a conductive material, arms (1520) provide electrical continuity between bolt (1530) and inner diameter surface (116) of transducer element (110). In the present example, curved sections (1522) are configured such that the regions of arms (1520) that contact inner diameter surface (116) are centered at locations that correspond to a node associated with resonant ultrasonic vibrations communicated through acoustic assembly (100). Other variations of bolt (1530) and arms (1520) will be apparent to those of ordinary skill in the art in view of the teachings herein. By way of example only, while two arms (1520) are shown, any other suitable number of arms (1520) may be provided.

C. Exemplary Expandable Contact Features for Inner Diameter of Cylindraceous Piezoelectric Transducer Element Various examples above include electrical contact features that are resiliently biased to an expanded configuration, to thereby provide electrical continuity between a bolt (130) (or similar feature) and the inner diameter surface (116) of transducer element (110). In some other instances, an electrical contact feature may include a non-resilient material that is deformable to an expanded configuration, to thereby provide electrical continuity between a bolt (130) (or similar feature) and the inner diameter surface (116) of transducer element (110). In other words, an electrical contact feature may be positioned within bore (111) of transducer element (110); then be deformed by another component and/or action (e.g., longitudinal compression) in order to achieve electrical continuity between a bolt (130) (or similar feature) and the inner diameter surface (116) of transducer element (110). Various examples of electrical contact features that may be non-resiliently deformed to expand outwardly in response to longitudinal compression by other components will be described in greater detail below, while further examples will be apparent to those of ordinary skill in the art in view of the teachings herein.

1. Exemplary Waveguide Feature with Expandable Leaves

Figure 41:
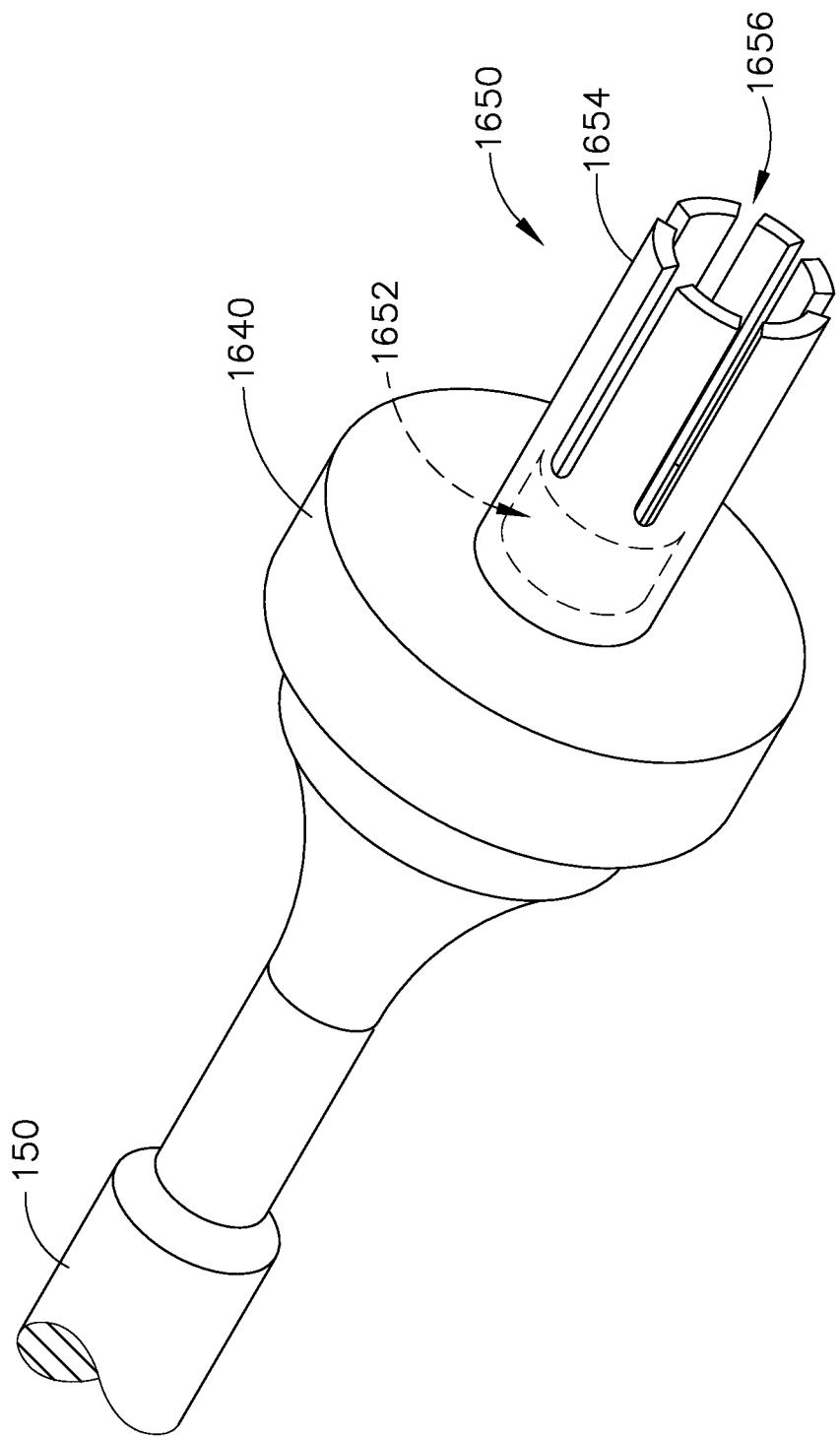
FIG. 41 depicts a perspective view of an exemplary horn with spreadable leaves.
Figure 42A:
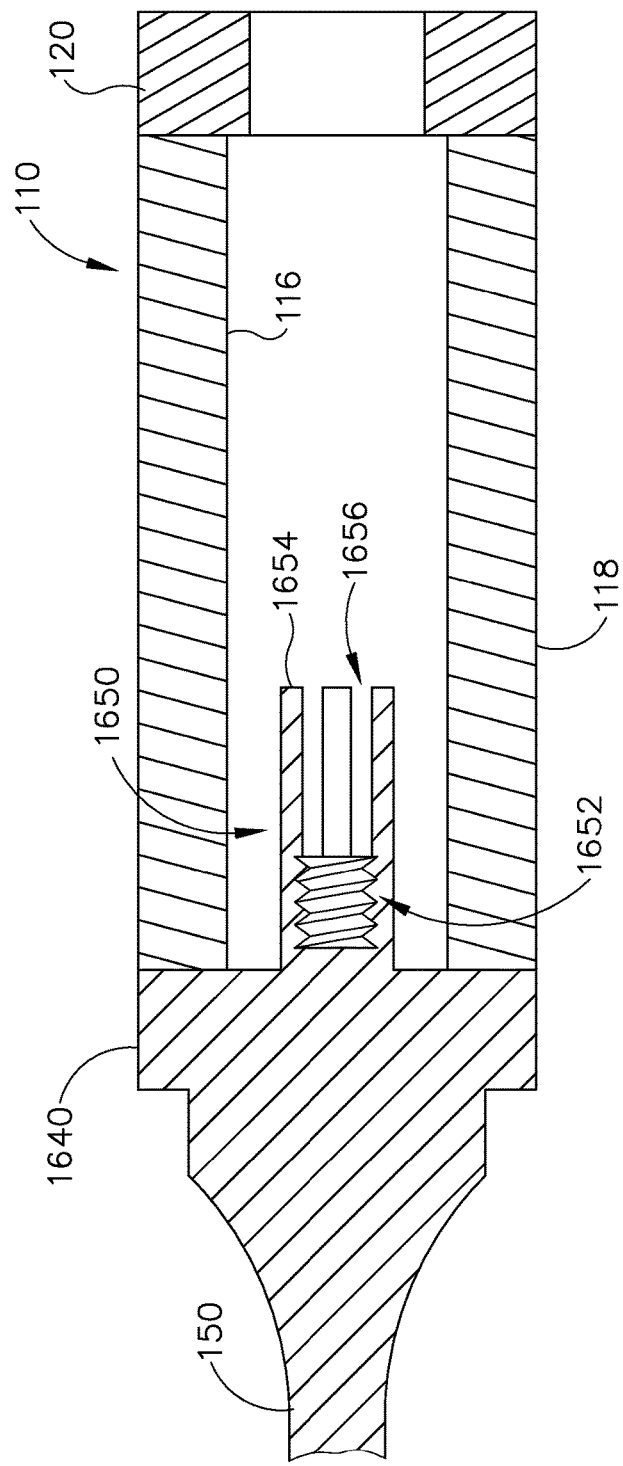
FIG. 42A depicts a cross-sectional side view of an exemplary acoustic assembly incorporating the horn of FIG. 41, with a bolt omitted.
Figure 42B:
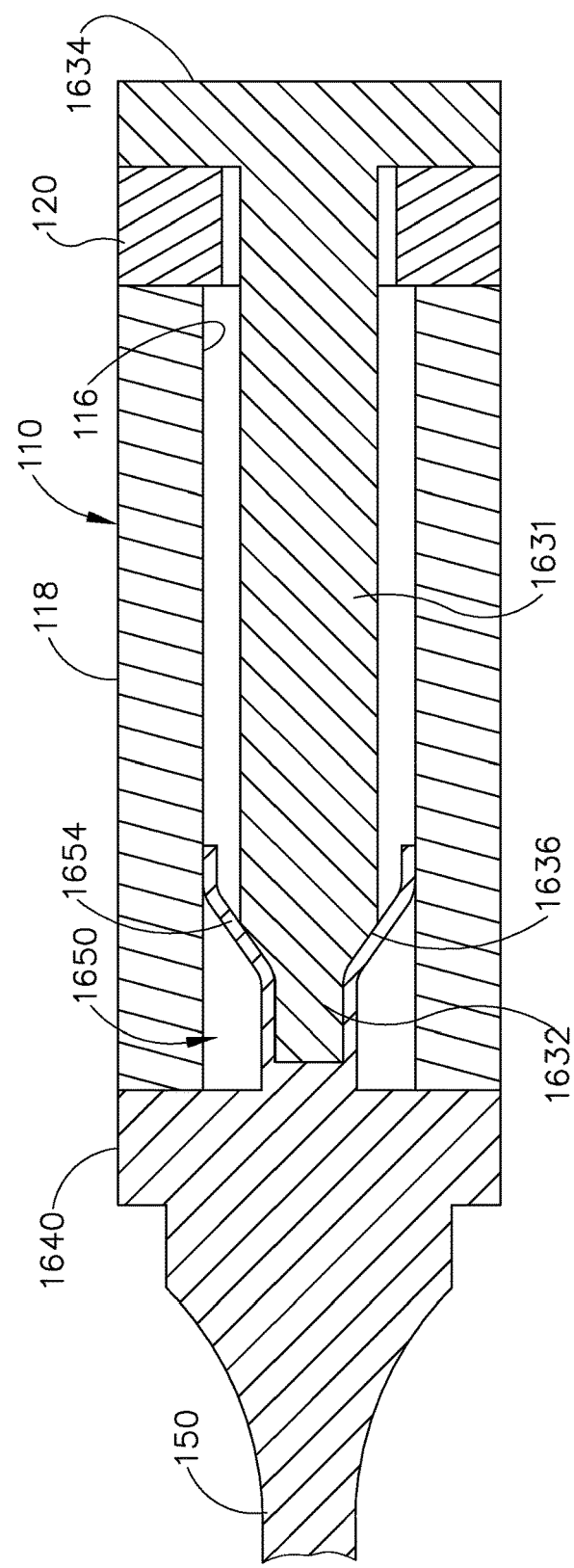
FIG. 42B depicts a cross-sectional side view of the assembly of FIG. 42A, with a tapered-tip bolt coupled with the horn to spread the leaves.

FIGS. 41-42B show an exemplary variation of horn (140) and bolt (130). In particular, FIGS. 41-42B show a horn (1640) that includes a deformable feature (1650). Deformable feature (1650) is configured like an internal collet. In particular, deformable feature (1650) defines an internal threading (1652) and includes a set of proximally extending leaves (1654). Leaves (1654) are separated by gaps (1656), which are configured to promote separation of leaves (1654) as will be described in greater detail below. In some versions, leaves (1654) are resiliently biased to assume the configuration shown in FIGS. 41-42A. In some other versions (1654) are malleable, and are initially formed to have the configuration shown in FIGS. 41-42A. Horn (1640) and deformable feature (1650) are electrically conductive. Various suitable materials and processes that may be used to form horn (1640) and deformable feature (1650) will be apparent to those of ordinary skill in the art in view of the teachings herein.

FIG. 42B shows bolt (1630), which includes a shank (1631) having a threaded distal end (1632), a head (1634), and a tapered region (1636) proximal to threaded distal end (1632). As shown in the transition from FIG. 42A to FIG. 42B, tapered region (1636) is configured to drive leaves (1654) outwardly and apart as threaded distal end (1632) is screwed into threading (1652) of deformable feature (1650). This deformation of leaves (1654) drives leaves (1654) into contact with inner diameter surface (116) of transducer element (110). Leaves (1654) thus provide a path for electrical continuity between horn (1640) and inner diameter surface (116). Various suitable ways in which horn (1640) may be further electrically coupled with generator (16) (or some other power source) will be apparent to those of ordinary skill in the art in view of the teachings herein. Similarly, numerous variations of deformable feature (1650) will be apparent to those of ordinary skill in the art in view of the teachings herein.

2. Exemplary Cylindraceous Member with Buckling Features

Figure 43:
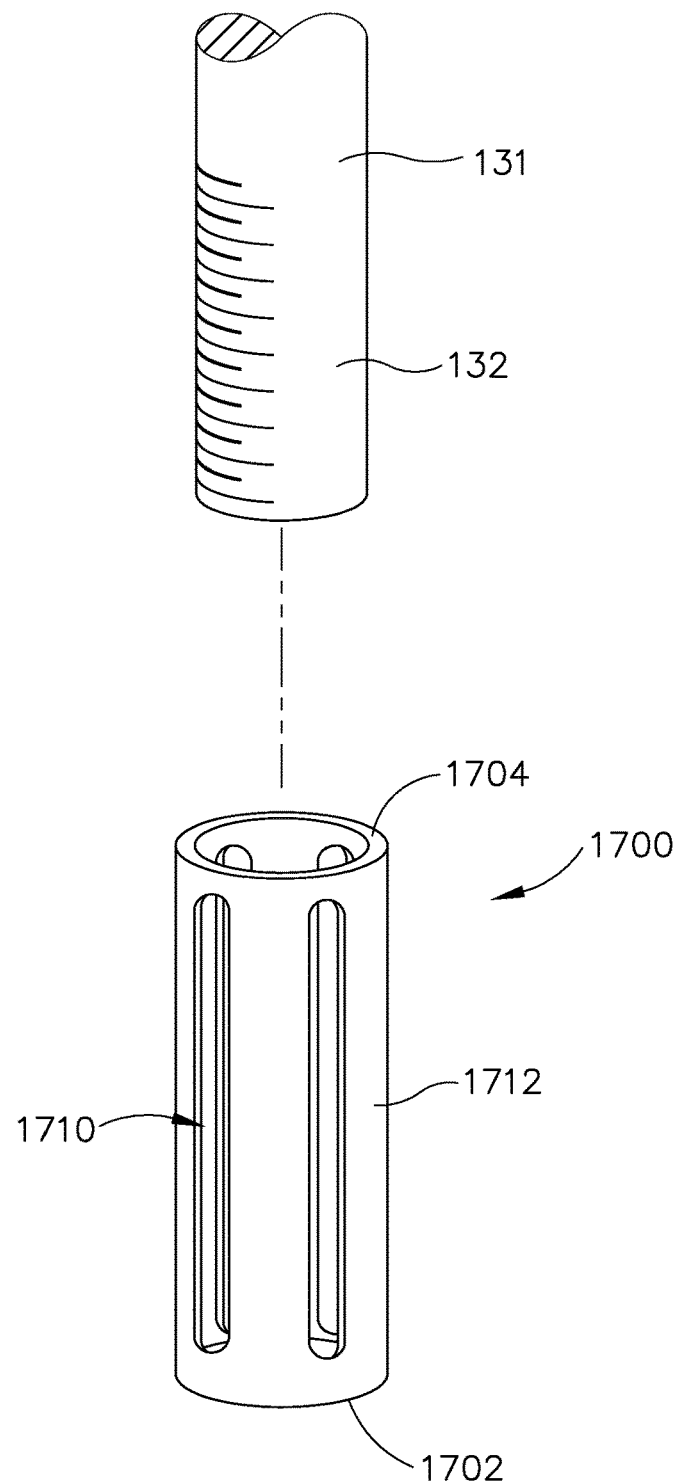
FIG. 43 depicts an exploded perspective view of another exemplary conductor and bolt assembly.
Figure 44:
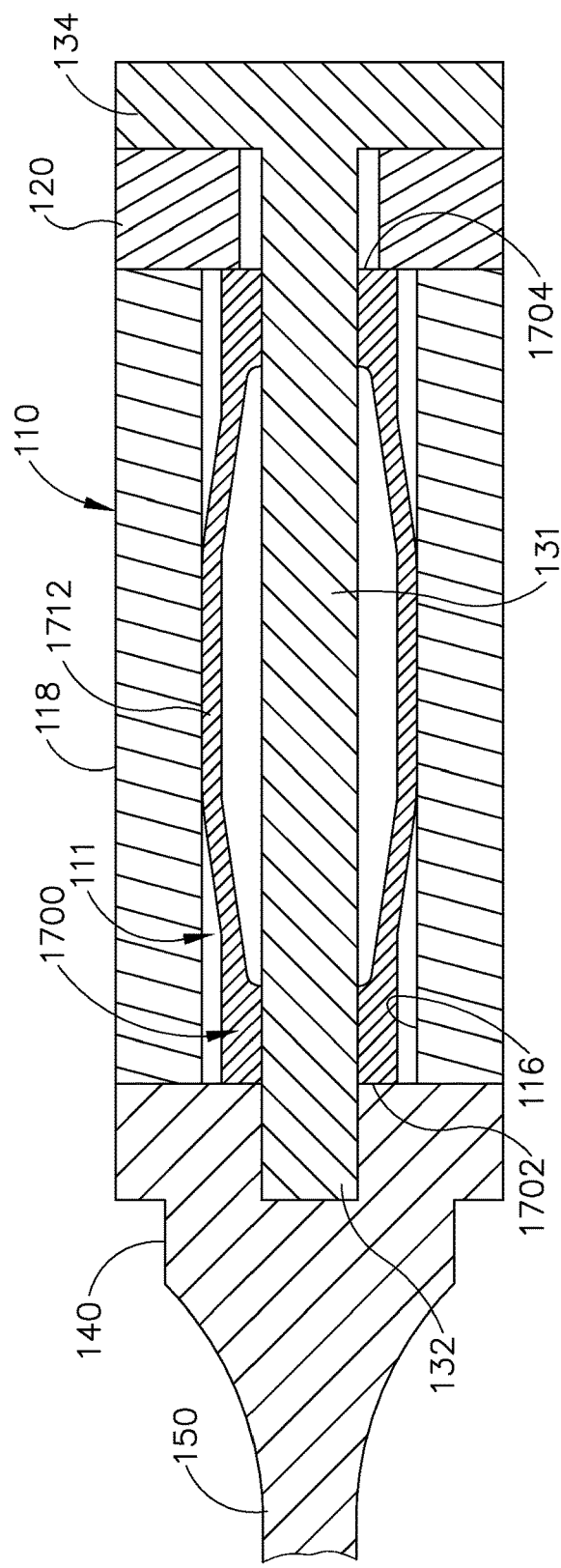
FIG. 44 depicts a cross-sectional side view of an exemplary acoustic assembly incorporating the conductor and bolt assembly of FIG. 43.

FIGS. 43-44 show another exemplary deformable electrical contact member (1700). Contact member (1700) of this example is cylindraceous in shape and has a distal end (1702) and a proximal end (1702). A plurality of longitudinally extending slots (1710) are formed along a portion of the length of contact member (1700). Slots (1710) define an array of ribs (1712). Contact member (1700) is sized to fit within bore (111) of transducer element (110). Contact member (1700) is further sized to insertingly receive shank (131) of bolt (130). Contact member (1700) is formed of a conductive and deformable material. Various suitable materials and processes that may be used to form contact member (1700) will be apparent to those of ordinary skill in the art in view of the teachings herein.

Contact member (1700) initially has a substantially straight, cylindraceous configuration as shown in FIG. 43. In this configuration, contact member (1700) has a height that is greater than the height of transducer element (110). Thus, when contact member (1700) is initially inserted in bore (111) while still in this straight configuration, distal end (1702) contacts horn (140) and proximal end (1704) protrudes proximally from transducer element (110). As endmass (120) is then engaged with proximal end (1704) and bolt (130) is secured to horn (140), head (134) of bolt (130)

and endmass (120) drive proximal end (1704) toward horn (140), thereby compressing the body of contact member (1700) longitudinally. This causes the body of contact member (1700) to buckle, such that ribs (1712) deform outwardly and into contact with the inner diameter surface (116) of transducer element (110) as shown in FIG. 44. Contact member (1700) thus operates similar to a deformable feature of a molly bolt, with an expanding effective outer diameter. Because contact member (1700) is formed of a conductive material, contact member (1700) thus provides electrical continuity between bolt (130) and inner diameter surface (116) of transducer element (110). Other variations of contact member (1700) will be apparent to those of ordinary skill in the art in view of the teachings herein.

3. Exemplary Bolt Feature with Buckling Arms

Figure 45:
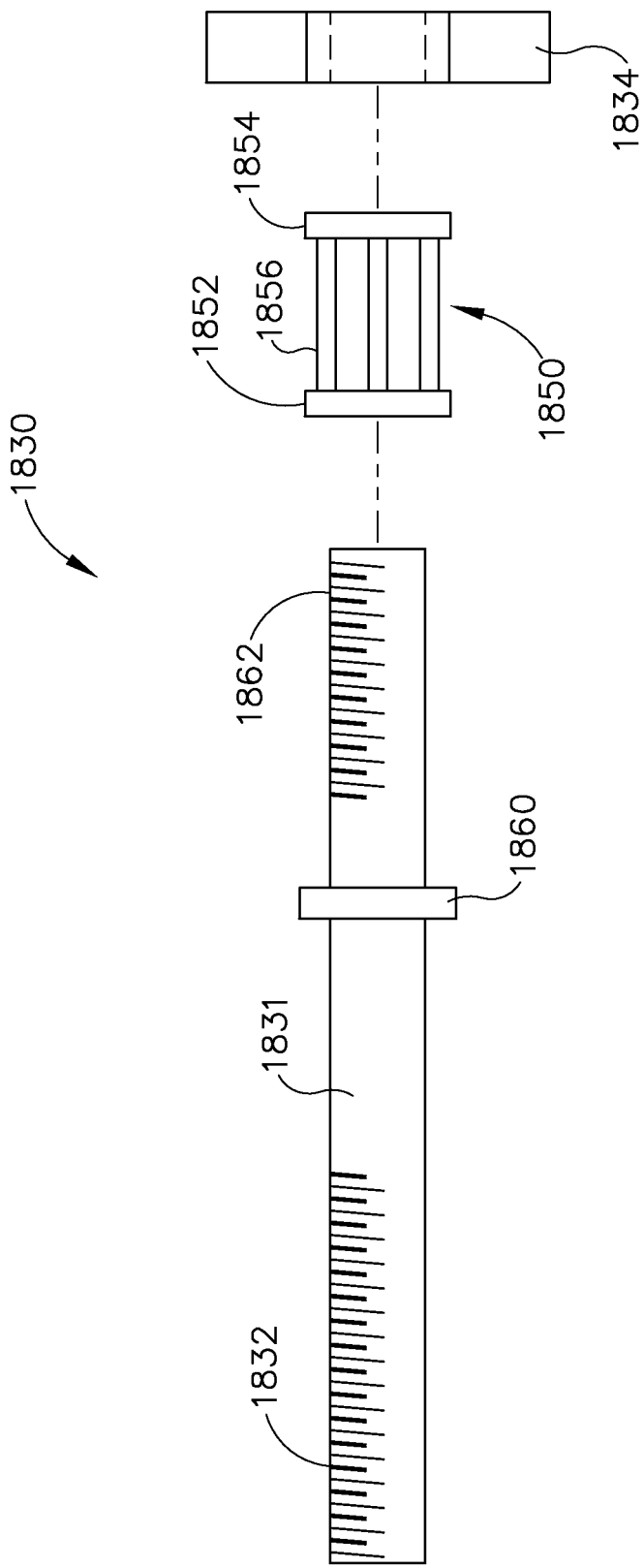
FIG. 45 depicts an exploded side view of another exemplary conductor and bolt assembly.
Figure 46:
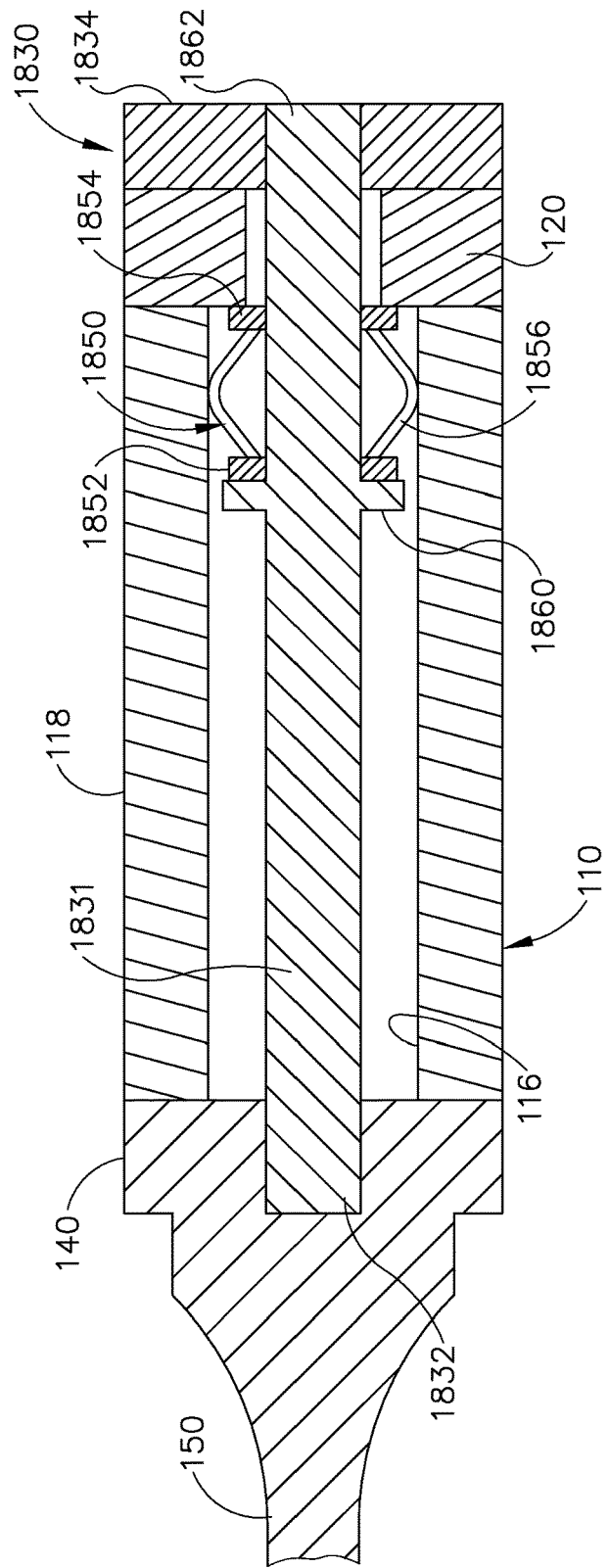
FIG. 46 depicts a cross-sectional side view of an exemplary acoustic assembly incorporating the conductor and bolt assembly of FIG. 45.

FIGS. 45-46 show an exemplary alternative bolt assembly (1830) that includes a deformable electrical contact member (1850). Bolt assembly (1830) further includes a shank (1831) having a threaded distal end (1832), a threaded proximal end (1862), and an outwardly extending flange (1860) located between ends (1832, 1862). Threaded distal end (1832) is configured to screw into the proximal end of horn (140) like threaded distal end (132) of bolt (130). Threaded proximal end (1862) is configured to receive a nut (1834), which acts like head (134) when secured to threaded proximal end (1862). Contact member (1850) comprises a distal annular member (1852), a proximal annular member (1854), and a plurality of legs (1856) extending between annular members (1852, 1854). The entire bolt assembly (1830), including contact member (1850), is formed of an electrically conductive and deformable material. Various suitable materials and processes that may be used to form bolt assembly (1830) will be apparent to those of ordinary skill in the art in view of the teachings herein. It should be understood that bolt assembly (1830) may be used as a substitute for bolt (130).

Contact member (1850) initially has a substantially straight configuration as shown in FIG. 45. In this configuration, contact member (1850) is slid over proximal end (1862) of shank (1831) until distal annular member (1852) engages flange (1860). Flange (1860) has a larger outer diameter than distal annular member (1852). Shank (1831) and contact member (1850) are inserted into bore (111). At this stage, the effective outer diameter of contact member (1850) is smaller than the inner diameter of bore (111). Endmass (120) is then slid over proximal end (1862), and then nut (1834) is secured to proximal end (1862). Distal end (1832) may be screwed into horn (140) at any suitable time during this assembly process. As nut (1834) is driven down proximal end (1862) toward distal end (1832), contact member (1850) is longitudinally compressed between flange (1860) and endmass (120). This causes legs (1856) of contact member (1850) to buckle, such that legs (1856) deform outwardly and into contact with the inner diameter surface (116) of transducer element (110) as shown in FIG. 46. Contact member (1850) thus operates similar to a deformable feature of a molly bolt, with an expanding effective outer diameter. Because contact member (1850) is formed of a conductive material, contact member (1850) thus provides electrical continuity between bolt assembly (1830) and inner diameter surface (116) of transducer element (110). Other variations of contact member (1850) and other portions of bolt assembly (1830) will be apparent to those of ordinary skill in the art in view of the teachings herein. By way of example only, while legs (1856) of the present example deform by bending, some other versions may have legs (1856) that have pinned hinges, living hinges, and/or other features that provide collapse and outward expansion of legs (1856) in some other fashion in response to longitudinal compression. As another merely illustrative variation, shank (1831) may be an integral feature of horn (140).

D. Exemplary Conductive Liquid Filler

Figure 47:
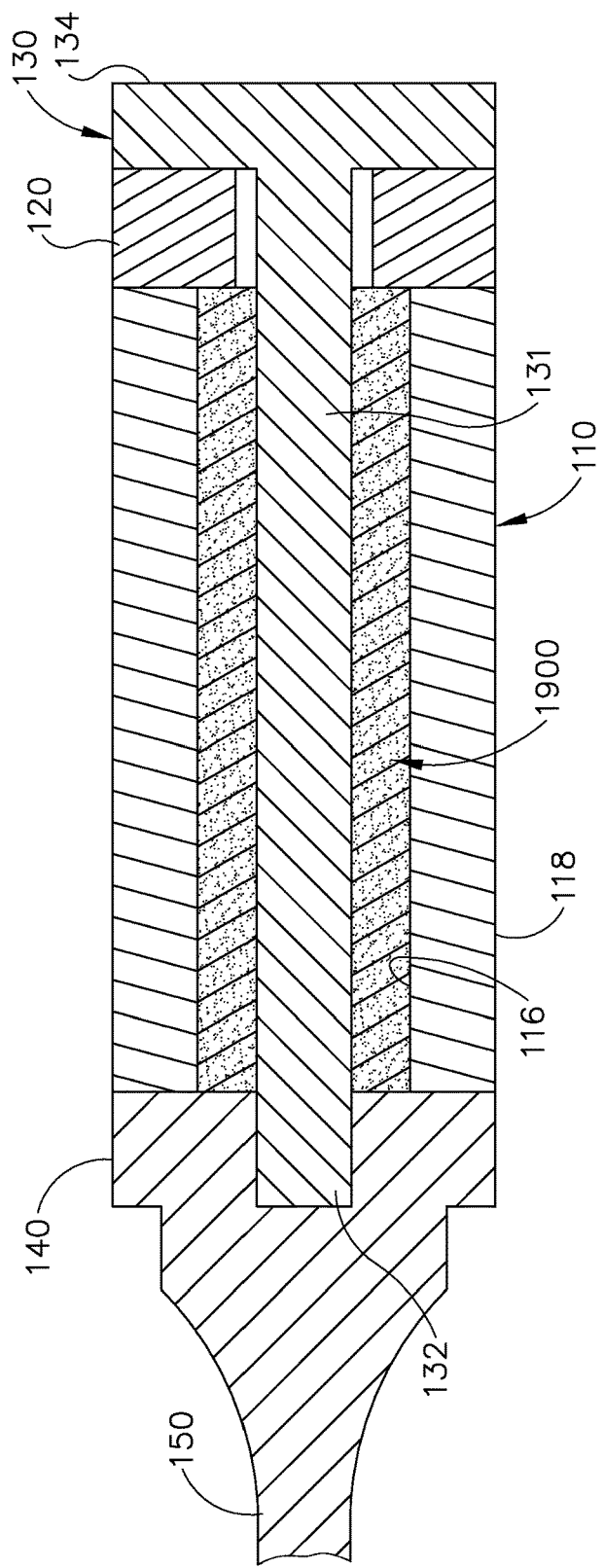
FIG. 47 depicts a cross-sectional side view of another exemplary acoustic assembly.

The above-described examples of resilient and/or otherwise deformable contact members contact only certain portions of inner diameter surface (116) of transducer element (110). In some instances, it may be desirable to contact the entire inner diameter surface (116) with a conductive member. One merely illustrative way in which this may be done is depicted in FIG. 47. In particular, FIG. 47 shows a filler material (1900) disposed within bore (111) of transducer element (110), between shank (131) and inner diameter surface (116). Filler material (1900) may comprise any suitable electrically conductive material, such as saline, silver epoxy, etc. Filler material (1900) may also have any suitable consistency, including but not limited to a liquid, a foam, a powder, a monolithic solid, etc. Various suitable kinds of material that may be used for filler material (1900) will be apparent to those of ordinary skill in the art in view of the teachings herein.

Similarly, various suitable ways in which filler material (1900) may be introduced into bore (111) will be apparent to those of ordinary skill in the art in view of the teachings herein. In some versions, filler material (1900) is introduced into bore (111) before shank (131) is inserted into bore (111). In some other versions, a shank like shank (1831) is introduced into bore, then filler material (1900) is introduced in the gap between shank (1831) and inner diameter surface (116), then a nut like nut (1834) is secured to shank (1831). Regardless of how filler material (1900) is introduced, it should be understood that the conductivity of filler material (1900) provides electrical continuity between bolt (130) and inner diameter surface (116) of transducer element (110).

E. Exemplary Annular Conductor about Bolt

Figure 48:
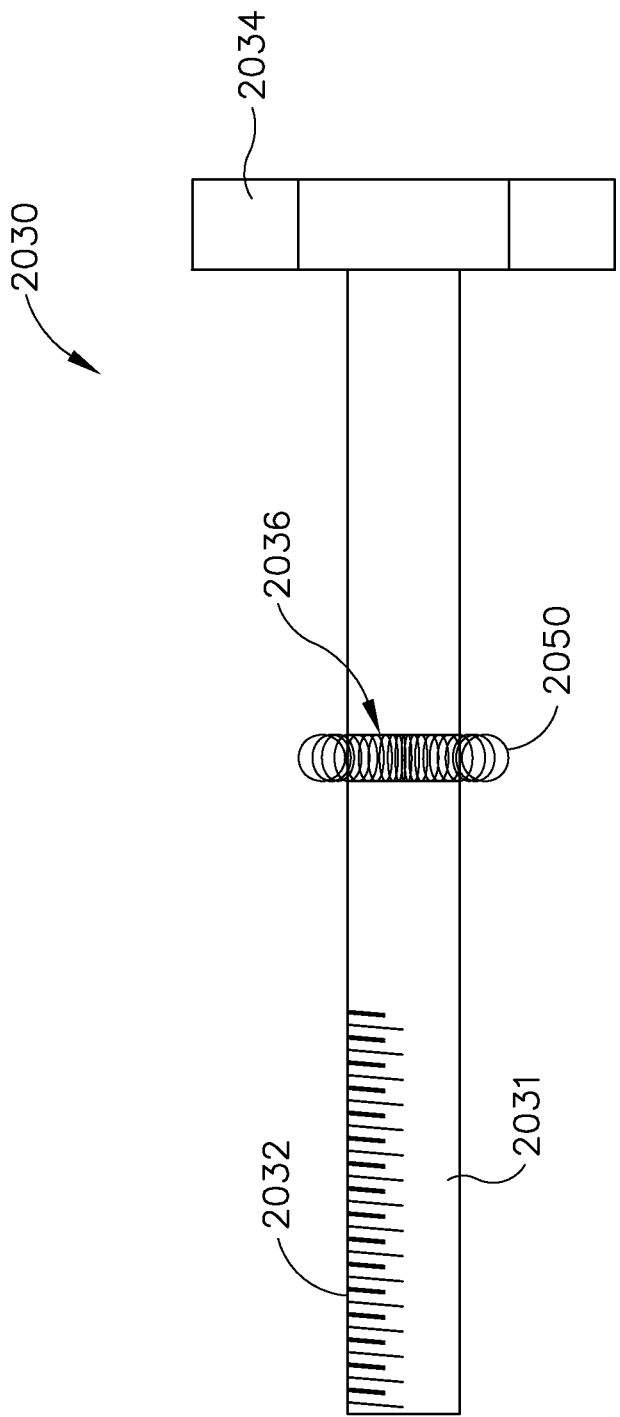
FIG. 48 depicts a side elevational view of another exemplary conductor and bolt assembly.
Figure 49:
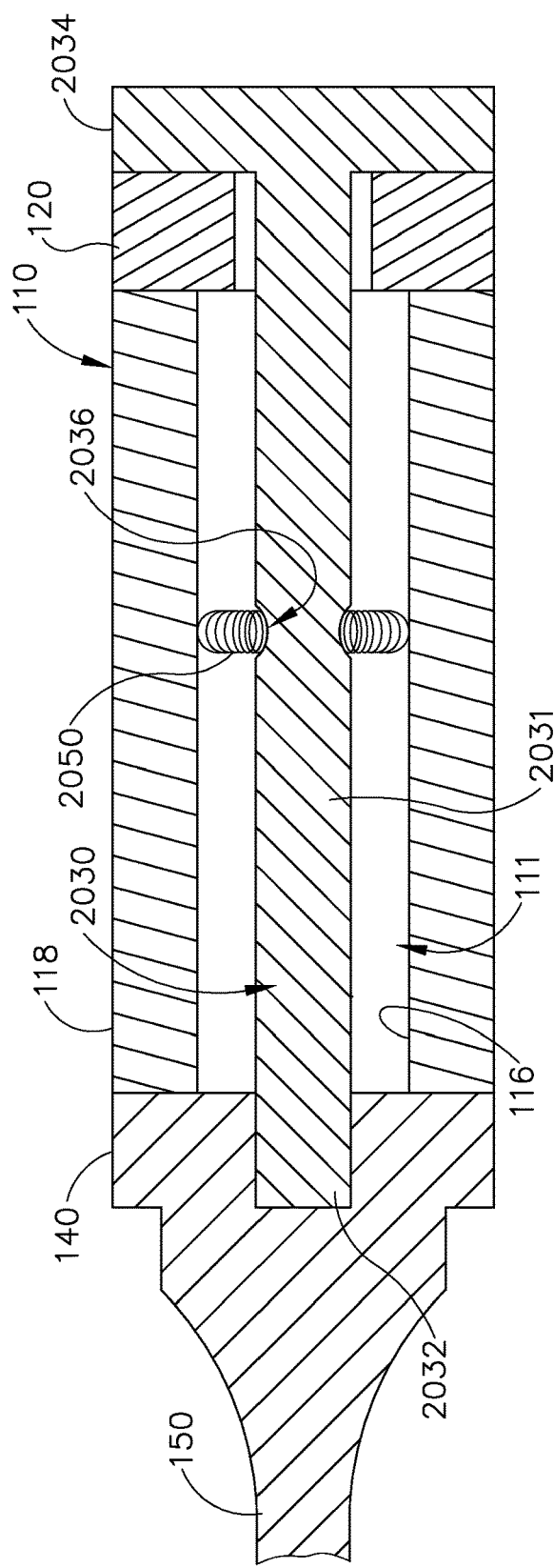
FIG. 49 depicts a cross-sectional side view of an exemplary acoustic assembly incorporating the conductor and bolt assembly of FIG. 48.

FIGS. 48-49 show an exemplary alternative bolt (2030) with an exemplary alternative electrical contact member (2050). Bolt (2030) of this example is substantially identical to bolt (130), and includes a shank (2031), a threaded distal end (2032), and a head (2034). Unlike bolt (130), bolt (2030) of this example includes an annular recess (2036) in shank (2031). Contact member (2050) is disposed in recess (2036). Contact member (2050) of this example comprises a continuous coil spring that is formed in an annular shape. The effective inner diameter of contact member (2050) is less than the outer diameter of shank (2031). In some versions contact member (2050) is resiliently biased to assume shape having an effective inner diameter that is less than the outer diameter of recess (2036), such that contact member (2050) fits snugly in recess (2036). Bolt (2030) and contact member (2050) are both formed of an electrically conductive material. Various suitable materials and processes that may be used to form bolt (2030) and contact member (2050) will be apparent to those of ordinary skill in the art in view of the teachings herein.

The effective outer diameter of contact member (2050) is less than the inner diameter of bore (111). Thus, when bolt (2030) and contact member (2050) are inserted into bore (111) as shown in FIG. 49, contact member (2050) is compressed between bolt (2030) and inner diameter surface (116). Because contact member (2050) is formed of a conductive material, contact member (2050) thus provides electrical continuity between bolt (2030) and inner diameter surface (116) of transducer element (110). Other variations of contact member (2050) will be apparent to those of ordinary skill in the art in view of the teachings herein.

F. Exemplary Conductive Foam Tube

Figure 50:
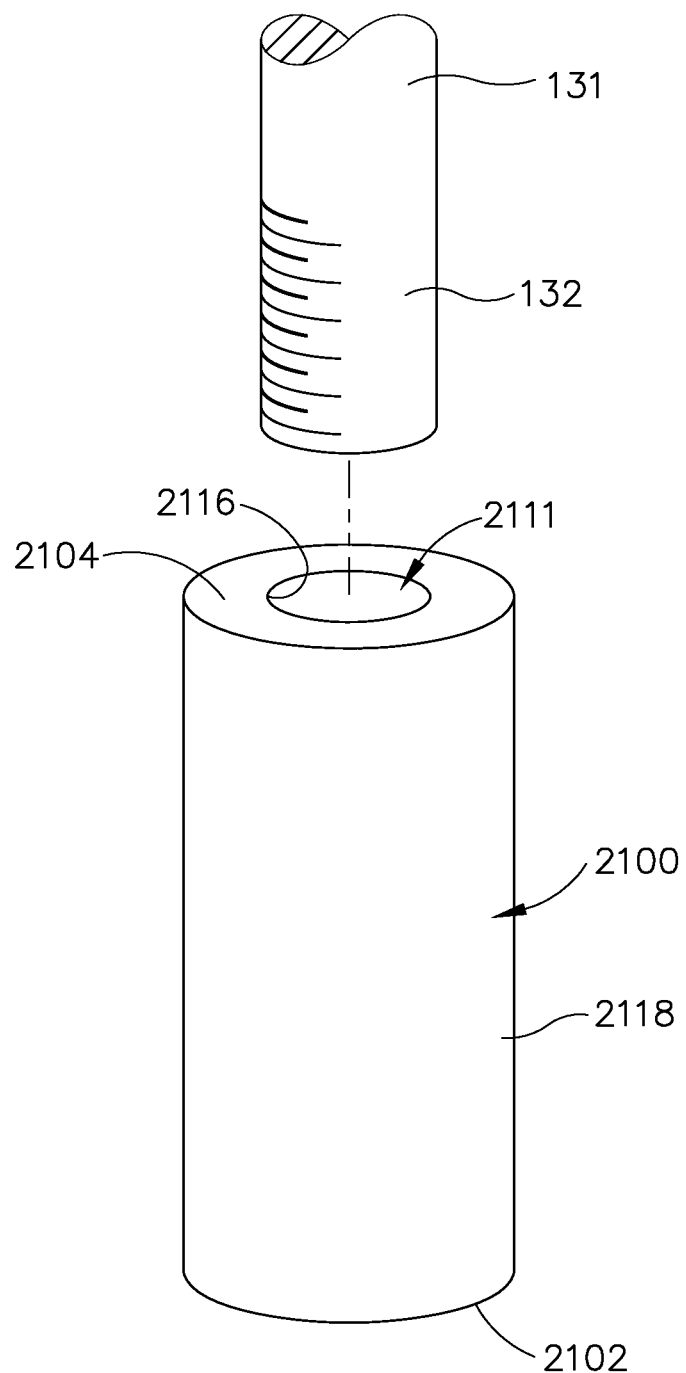
FIG. 50 depicts an exploded perspective view of another exemplary conductor and bolt assembly.
Figure 51:
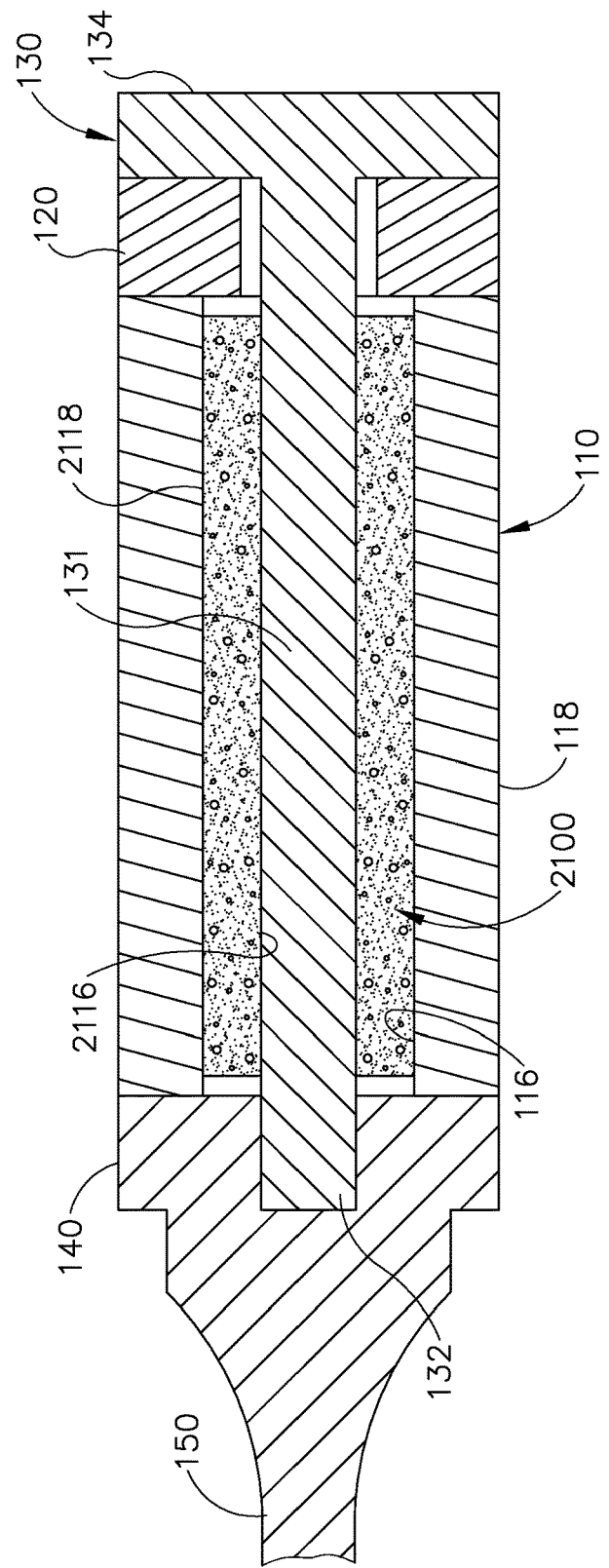
FIG. 51 depicts a cross-sectional side view of an exemplary acoustic assembly incorporating the conductor and bolt assembly of FIG. 50.

FIGS. 50-51 show an exemplary electrically conductive foam tube (2100) that may be interposed between shank (131) of bolt (130) and inner diameter surface (116) of transducer element (110). Foam tube (2100) has a distal end (2102), a proximal end (2104), an outer diameter surface (2118), and an inner diameter surface (2116) defining a bore (2111). Foam tube (2100) is formed of an electrically conductive material that is compressible. By way of example only, foam tube (2100) may be formed of steel wool and/or some other metallic material formed like steel wool. Various suitable materials and processes that may be used to form foam tube (2100) will be apparent to those of ordinary skill in the art in view of the teachings herein.

In some versions, the inner diameter of bore (2111) is less than the outer diameter of shank (131) before shank (131) is inserted into bore (2111). Inner diameter surface (2116) thus fully contacts shank (131) when shank (131) is inserted into bore (2111). In addition, the outer diameter of foam tube (2100) is less than the inner diameter of bore (111) before foam tube (2100) is inserted into bore (111). Outer diameter surface (2118) of foam tube (2100) thus fully contacts inner diameter surface (116) of transducer element (110) when foam tube (2100) is inserted into bore (111) as shown in FIG. 51. It should therefore be understood that foam tube (2100) fully contacts both shank (131) and inner diameter surface (116) when assembled as shown in FIG. 51. Because foam tube (2100) is formed of a conductive material, foam tube (2100) thus provides electrical continuity between bolt (130) and inner diameter surface (116) of transducer element (110). Other variations of foam tube (2100) will be apparent to those of ordinary skill in the art in view of the teachings herein.

By way of example only, some versions of foam tube (2100) may have a height that is greater than the length of bore (111) before foam tube (2100) is inserted into bore (111). In some such versions, when bolt (130) is secured to horn (140), bolt (130), endmass (120), and horn (140) may cooperate to longitudinally compress foam tube (2100), which may drive inner diameter surface (2116) inwardly into further contact with shank (131) and/or outer diameter surface (2118) outwardly into further contact with inner diameter surface (116). As one merely illustrative variation of such a version, foam tube (2100) may have an accordion-like profile that promotes even inward/outward deflection in response to longitudinal compression. It should also be understood that such a configuration need not necessarily be formed of a foam material. For instance, such a configuration may be formed of sheet metal and/or some other kind/form of material(s). In some other variations, foam tube (2100) is configured more like a relatively short washer, rather than being configured as an elongate tube.

Figure 52:
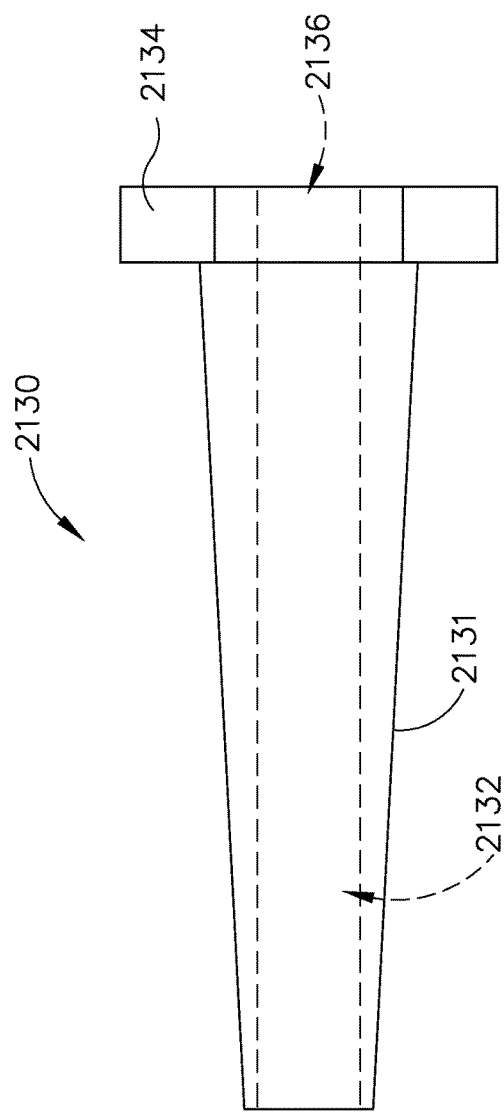
FIG. 52 depicts a side elevational view of an exemplary nut with a hollow shank.
Figure 53:
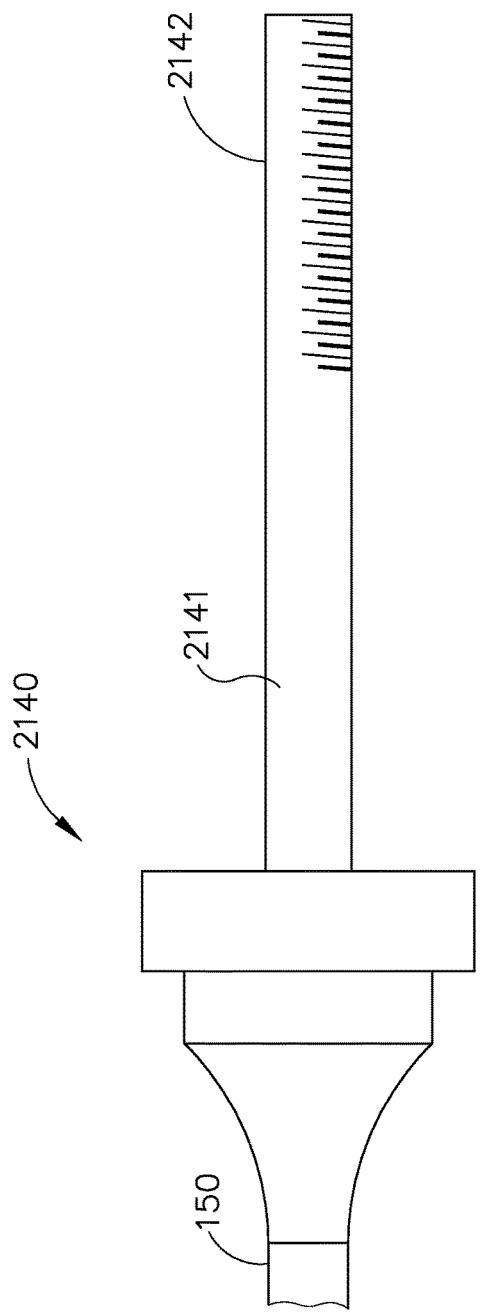
FIG. 53 depicts a side elevational view of an exemplary horn with a threaded shank.
Figure 54:
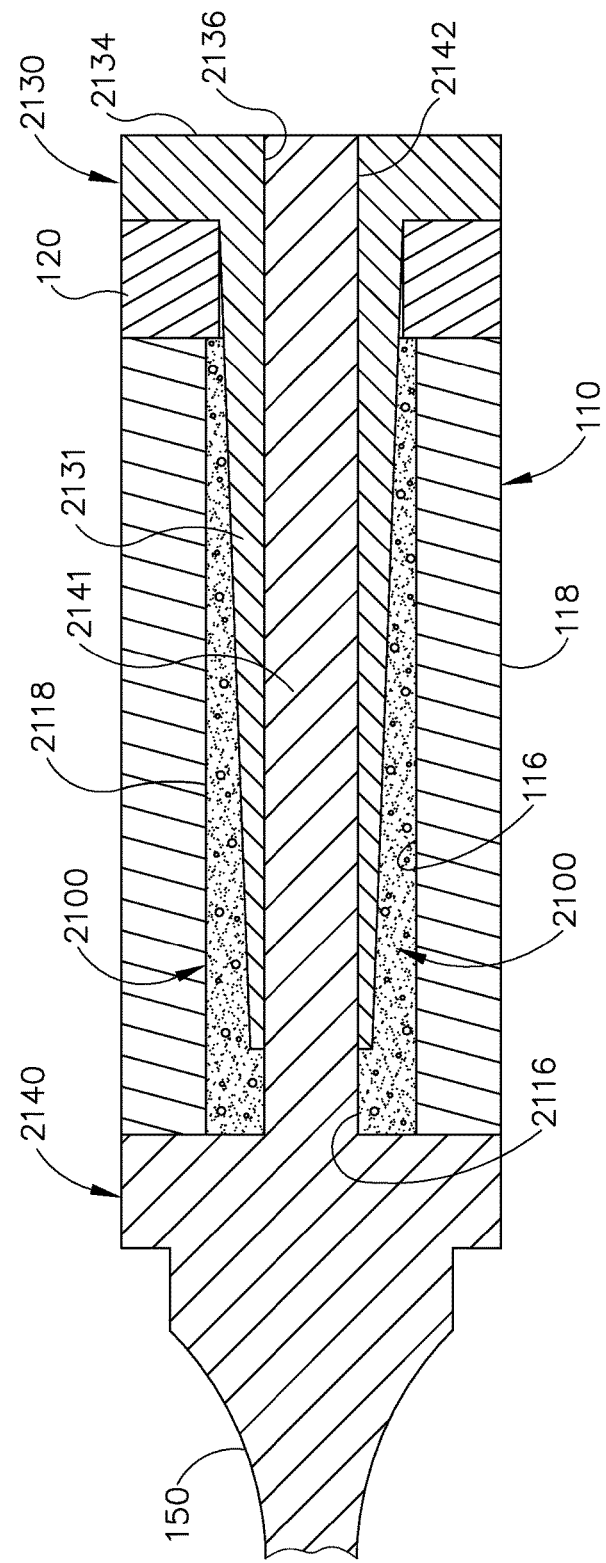
FIG. 54 depicts a cross-sectional side view of an exemplary acoustic assembly incorporating the nut of FIG. 52 and the horn of FIG. 53.

FIGS. 52-54 show another merely illustrative variation. In particular, FIGS. 52-54 show foam tube (2100) being used with an exemplary alternative horn (2140) and an exemplary alternative nut (2130). As best seen in FIG. 52, nut (2130) includes a tapered shank (2131) that defines a bore (2132). The proximal end (2136) of bore (2132) is threaded. The proximal end of shank (2131) includes a head (2134). As best seen in FIG. 53, horn (2140) includes a proximally extending shank (2141) having a threaded proximal end (2142). Waveguide (150) extends distally from horn (2140). Shank (2141) of horn (2140) is sized to fit in bore (2132) of nut (2130). The threading at proximal end (2136) of bore (2132) is configured to complement the threading at proximal end (2142) of shank (2131). Nut (2130) of the present example is formed of an electrically conductive material. Horn (2140) may also be formed of an electrically conductive material.

As shown in FIG. 54, foam tube (2100) fits between the exterior of shank (2131) and inner diameter surface (116) of transducer element (110). During assembly, foam tube (2100) may be initially disposed about shank (2141). Shank (2131) may then be inserted over shank (2141), between shank (2141) and inner diameter surface (2116) of foam tube (2100). The tapered configuration of shank (2131) assists in further compressing outer diameter surface (2118) of foam tube (2100) against inner diameter surface (116) of transducer element (110). Because foam tube (2100) is formed of a conductive material, foam tube (2100) thus provides electrical continuity between nut (2130) and inner diameter surface (116) of transducer element (110). Still other variations of foam tube (2100) and components that may be used therewith will be apparent to those of ordinary skill in the art in view of the teachings herein.

Figure 55:
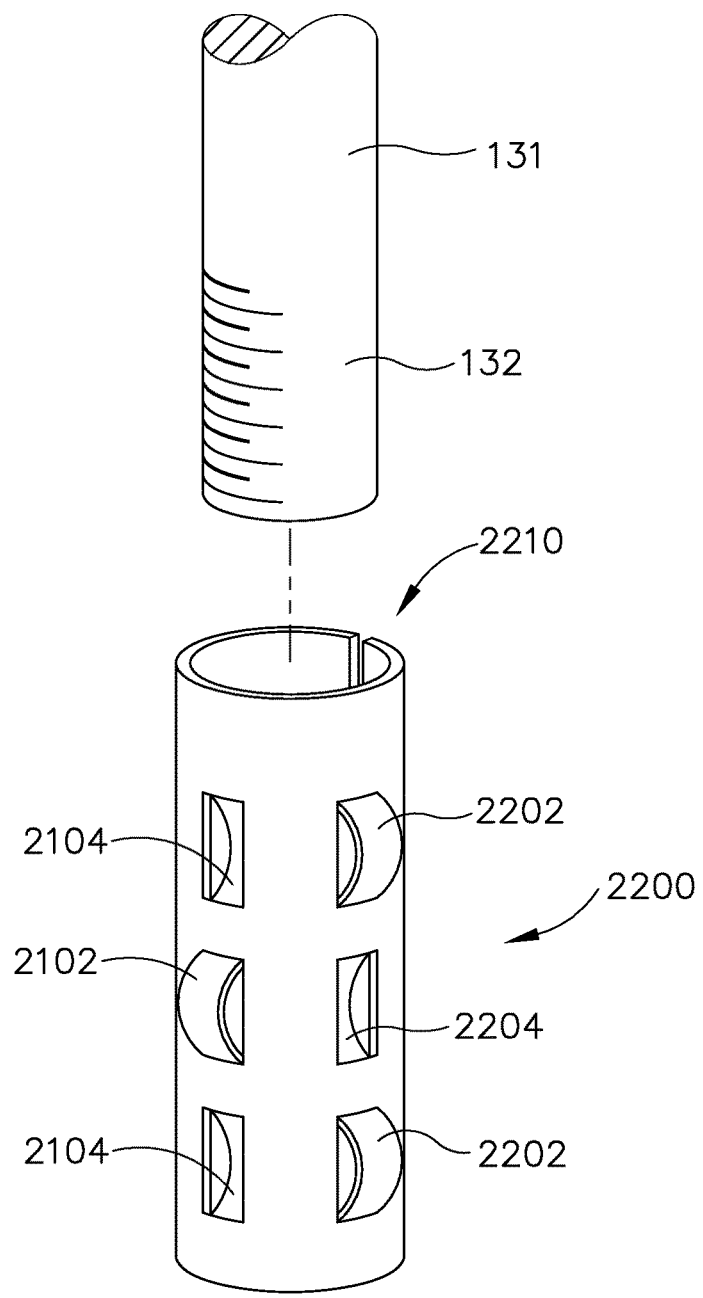
FIG. 55 depicts an exploded perspective view of another exemplary conductor and bolt assembly.
Figure 56:
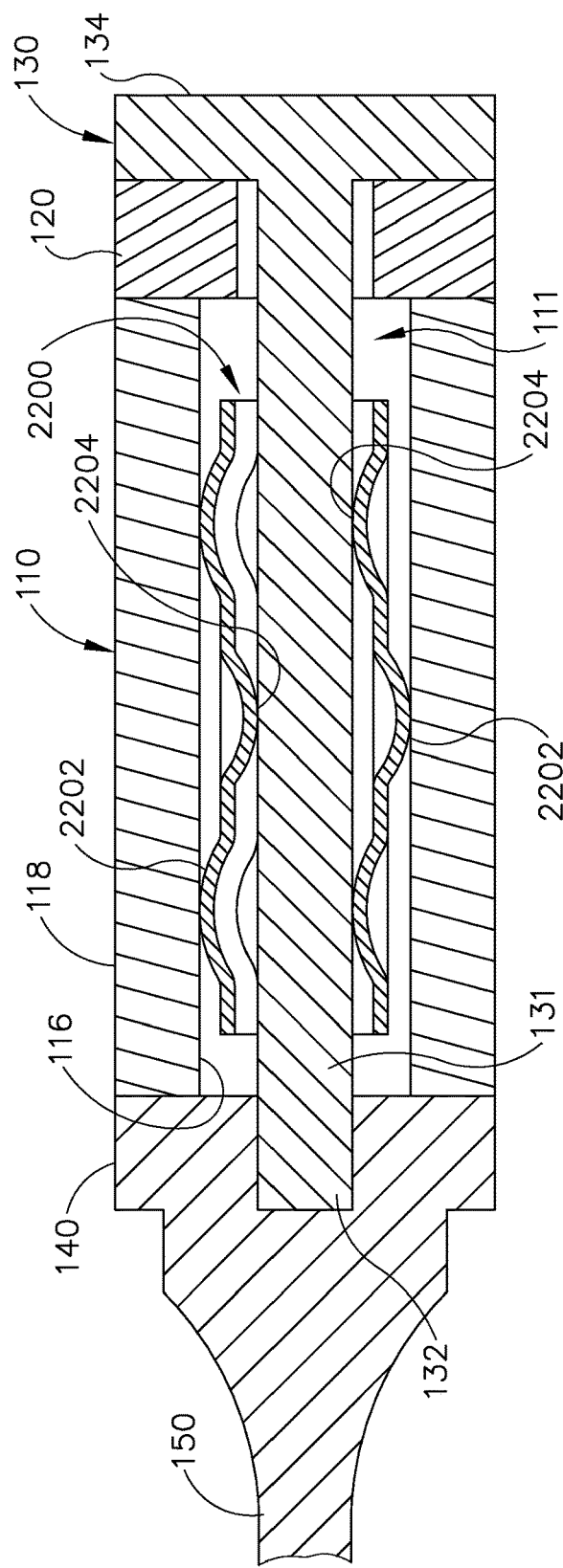
FIG. 56 depicts a cross-sectional side view of an exemplary acoustic assembly incorporating the conductor and bolt assembly of FIG. 55.

G. Exemplary Alternating Contact Features for Inner and Outer Diameters of Cylindraceous Piezoelectric Transducer Element FIGS. 55-56 show another exemplary electrical contact member (2200) that is configured to simultaneously contact bolt (130) and inner diameter surface (116) of transducer element (110). Contact member (2200) of this example comprises a sheet of metal that is stamped and then rolled into a cylindraceous configuration, presenting a seam (2210). The material forming contact member (2200) may be resilient, such that contact member (2200) may be biased to return to a generally flat configuration after contact member (2200) is rolled into the cylindraceous configuration. In some other versions, contact member (2200) is formed as a seamless tube. Various suitable materials and processes that may be used to form contact member (2200) will be apparent to those of ordinary skill in the art in view of the teachings herein.

Contact member (2200) of the present example further includes a plurality of outwardly projecting features (2202) and a plurality of inwardly projecting features (2204). Outwardly projecting features (2202) have a convex configuration while inwardly projecting features (2204) have a concave configuration. In the example shown in FIGS. 55-56, the positioning of features (2202, 2204) alternates along the length and circumference of contact member (2200). Of course, any other suitable arrangement may be used. For instance, in some other versions, the distal-most band of features (2202, 2204) consists solely of inwardly projecting features (2204), the intermediate band of features (2202, 2204) consists solely of outwardly projecting features (2202), and the proximal-most band of features (2202, 2204) consists solely of inwardly projecting features (2204). Other suitable arrangements will be apparent to those of ordinary skill in the art in view of the teachings herein.

Contact member (2200) is configured to fit in bore (111) of transducer element (110), between shank (131) of bolt (130) and inner diameter surface (116) of transducer element. With contact member (2200) in the rolled configuration, outwardly projecting features (2202) together define an effective outer diameter that is greater than the inner diameter of bore (1110). Outwardly projecting features (2202) thus contact inner diameter surface (116) when contact member (2200) is inserted in bore (111) as shown in FIG. 56. In some versions, each outwardly projecting feature (2202) contacts inner diameter surface (116) at a location corresponding to a node associated with resonant ultrasonic vibrations communicated through acoustic assembly (100).

In addition, when contact member (2200) is in the rolled configuration, inwardly projecting features (2204) together define an effective inner diameter that is less than the outer diameter of shank (131). Inwardly projecting features (2204) thus contact shank (131) when contact member (2200) is disposed about shank (131) as shown in FIG. 56. In some versions, features (2202, 2204) are resiliently biased such that outwardly projecting features (2202) resiliently bear against inner diameter surface (116) and inwardly projecting features (2204) resiliently bear against shank (131). Because contact member (2200) is formed of a conductive material, contact member (2200) provides electrical continuity between bolt (130) and inner diameter surface (116) of transducer element (110) when assembled as shown in FIG. 56. Other variations of contact member (2200) will be apparent to those of ordinary skill in the art in view of the teachings herein.

IV. Exemplary Alternative Contact Features for Outer Diameter of Cylindraceous Piezoelectric Transducer Element Several of the foregoing examples relate specifically to components and features that may be used to provide electrical continuity between a bolt (130) (or a variation thereof) and inner diameter surface (116) of transducer element (110), with some other components/features further providing electrical continuity between a bolt (130) (or variation thereof) and generator (14) (or some other power source). As noted above, outer diameter surface (118) of transducer element (110) will also need to be placed in electrical continuity with generator (14) (or some other power source) in order to generate a voltage in transducer element (110) to thereby induce ultrasonic vibrations in acoustic assembly (100). The examples described below include various features that are configured to contact either outer diameter surface (118) directly or some conductive material that is deposited on or otherwise applied to outer diameter surface (118), to thereby provide electrical continuity between outer diameter surface (118) and generator (14) (or some other power source). It should be understood that the examples described below may be readily combined with any of the teachings herein relating to ways in which electrical communication may be provided to inner diameter surface (116). Other suitable instrument configurations in which the below teachings may be applied will be apparent to those of ordinary skill in the art.

By way of example only, outer diameter surface (118) may include a conductive coating or insert (e.g., BeCu, brass, some other copper alloy, etc.) that is in contact with any of the various features described below, in order to provide electrical communication with outer diameter surface (118). It should also be understood that each of the various below-described electrical contact features may be longitudinally positioned at (or positioned to make contact at) a location corresponding to a node associated with resonant ultrasonic vibrations communicated through acoustic assembly (100). To the extent that the electrical contact features are not initially positioned at such nodal locations, some such electrical contact features may eventually migrate to such positions after a certain time period during which acoustic assembly (100) is activated. In other words, the vibrations communicated through acoustic assembly (100) may eventually drive electrical contact features to nodal locations.

A. Exemplary Conductive Cuff

Figure 57:
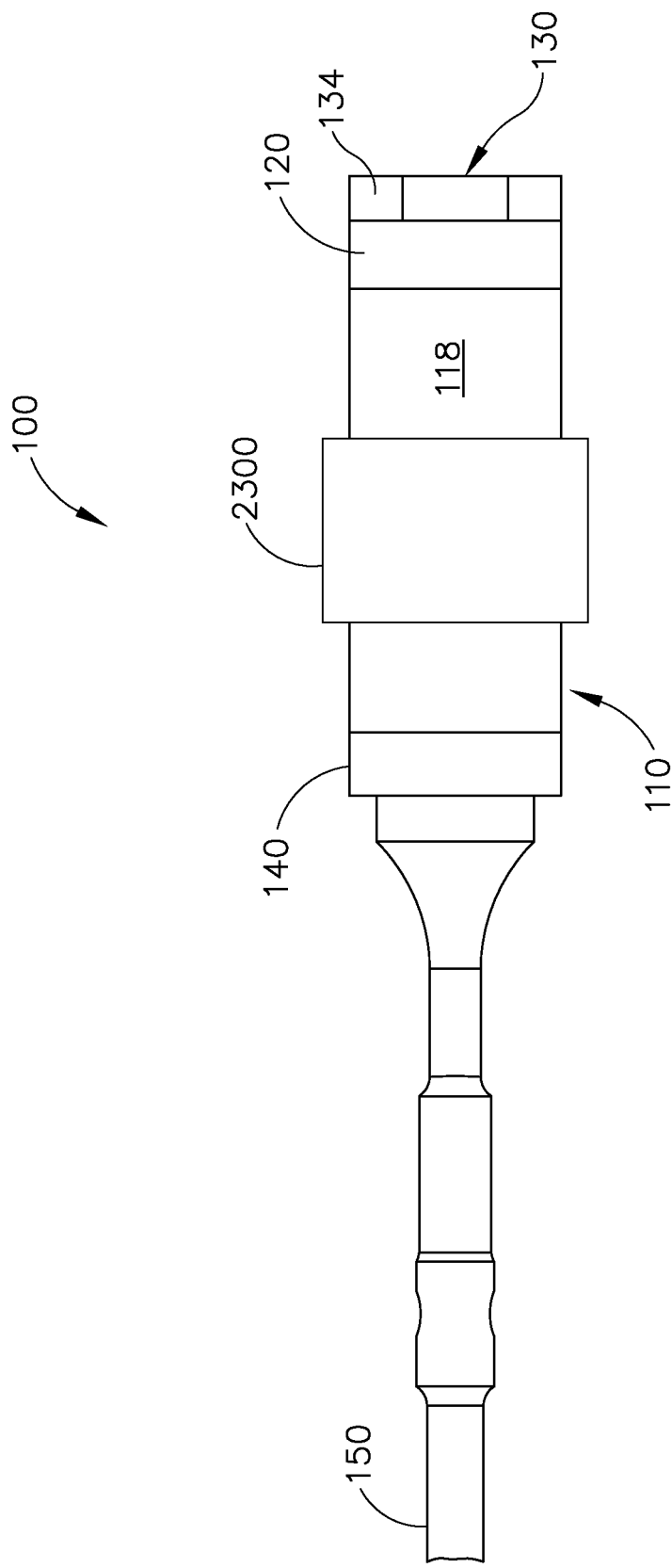
FIG. 57 depicts a partial side elevational view of another exemplary acoustic assembly, with a conductive cuff disposed about the transducer element.

FIG. 57 shows an exemplary cuff (2300) disposed about outer diameter surface (118) of transducer element (110). Cuff (2300) is formed of a conductive material and is configured to provide a structurally robust point of contact for a brush, leaf spring, or other conductive component that is coupled with generator (14) or some other power source. In particular, cuff (2300) has a hardness and/or thickness selected to permit transducer element (110) to be rotated relative to the external contact (e.g., brush, leaf spring, etc.) without compromising the structural integrity of cuff (2300) and without compromising the electrically communicative contact between cuff (2300) and the external contact. By way of example only, cuff (2300) may be formed using a plating, screen printing, or lamination process. Various suitable materials and processes that may be used to form cuff (2300) will be apparent to those of ordinary skill in the art in view of the teachings herein. Similarly, various kinds of external contacts that may be used to mechanically and electrically engage cuff (2300) will be apparent to those of ordinary skill in the art in view of the teachings herein.

B. Exemplary Winding Conductive Assembly

Figure 58A:
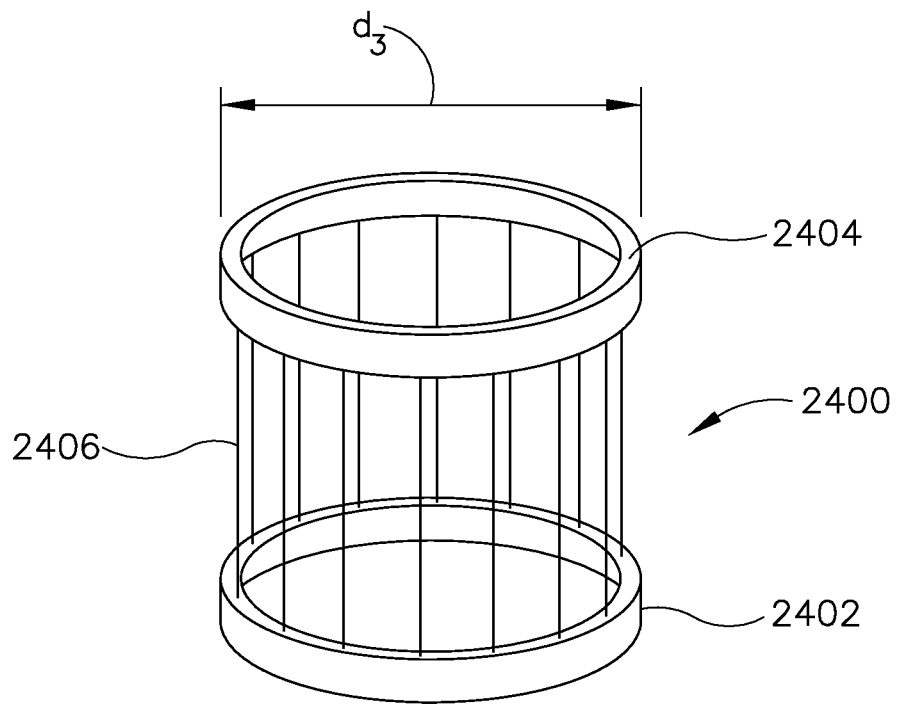
FIG. 58A depicts a perspective view of an exemplary conductor assembly in an unwound state.
Figure 58B:
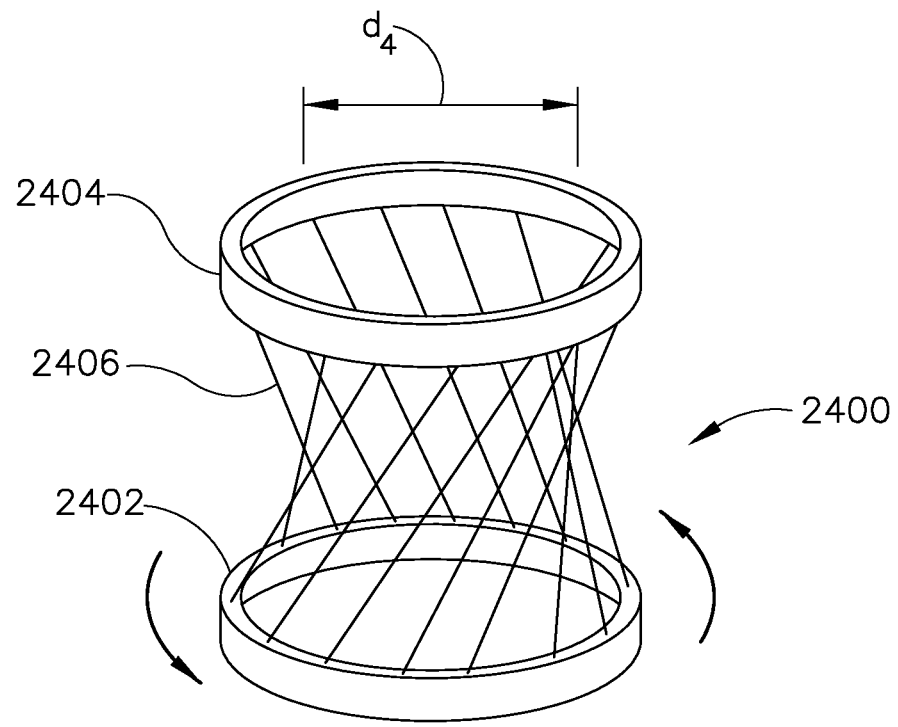
FIG. 58B depicts a perspective view of the conductor assembly of FIG. 58A in a wound state.
Figure 59:
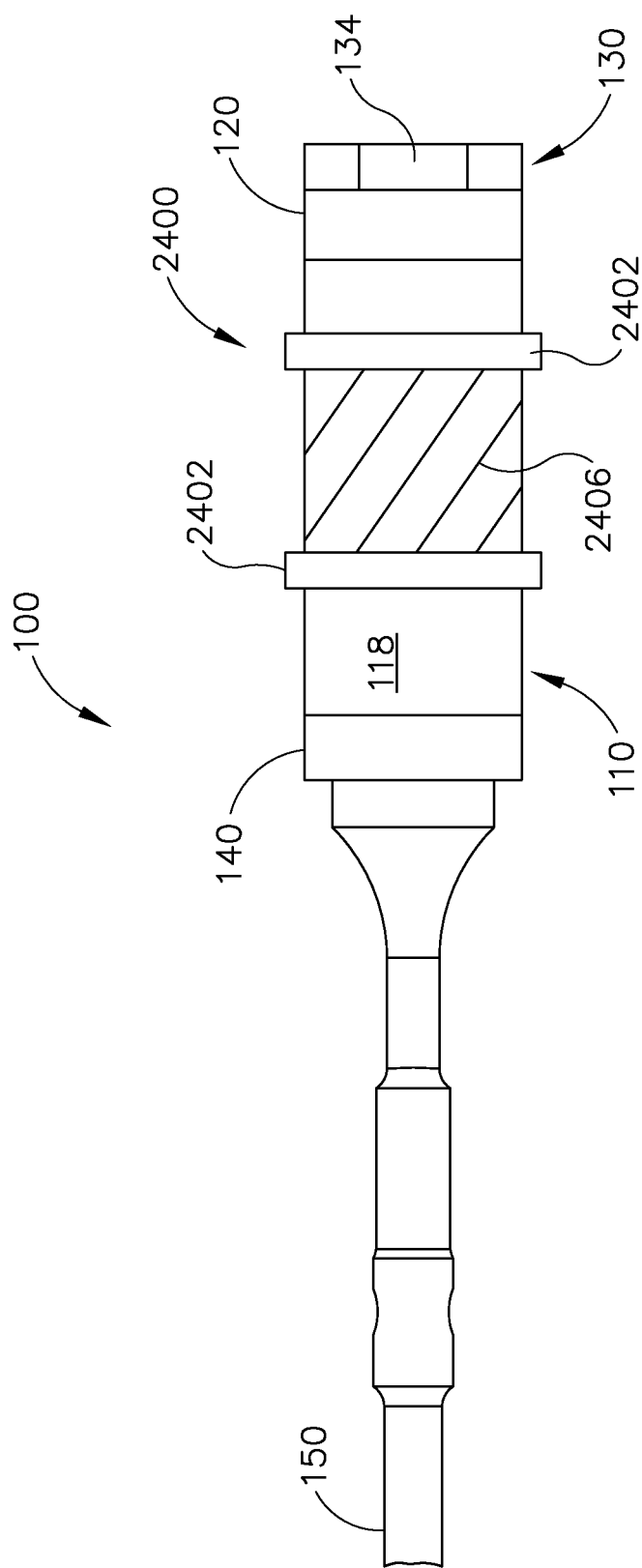
FIG. 59 depicts a partial side elevational view of another exemplary acoustic assembly, with the conductor assembly of FIG. 58B disposed about the transducer element.

FIGS. 58A-59 show an exemplary contact member (2400) that may be used to contact outer diameter surface (118) or some feature that is already in contact with outer diameter surface (118) (e.g., cuff (2300), etc.). Contact member (2400) of this example comprises a distal annular member (2402), a proximal annular member (2404), and a plurality of wires (2406) extending longitudinally between annular members (2404). Annular members (2402, 2404) and wires (2406) are all formed of electrically conductive material in the present example. Contact member (2400) is configured to transition between a first state (as shown in FIG. 58A) and a second state (as shown in FIG. 58B) by rotating one annular member (2402, 2404) relative to the other annular member (2402, 2404) about a longitudinal axis extending through the center of contact member (2400). Wires (2406) are oriented obliquely relative to annular members (2402, 2404) when contact member (2400) is in the second state. As shown in FIG. 58A, wires (2406) together define a first effective outer diameter ($d_3$) when contact member (2400) is in the first state. As shown in FIG. 58B, wires (2406) together define a second effective outer diameter ($d_4$) when contact member (2400) is in the second state. The second effective outer diameter ($d_4$) is less than the first effective outer diameter ($d_3$).

In the present example, the first effective outer diameter ($d_3$) is greater than the outer diameter of transducer element (110). Contact member (2400) may thus be positioned about outer diameter surface (118) of transducer element (110) when contact member (2400) is in the first state. When contact member (2400) is suitably positioned about outer diameter surface (118) one annular member (2402, 2404) may be rotated relative to the other annular member (2402, 2404) to transition contact member (2400) to the second state. While transitioning to the second state, wires (2406) are brought into contact with outer diameter surface (118) as shown in FIG. 59. The positions of annular members (2402, 2404) may then be fixed (e.g., secured to shroud housing (52), etc.). Either or both of annular members (2402, 2404) may further be coupled with generator (14) (or some other power source) using any suitable components and arrangements as will be apparent to those of ordinary skill in the art in view of the teachings herein. Since contact member (2400) is electrically conductive, contact member (2400)

provides electrical continuity between outer diameter surface (118) generator (14) (or some other power source) via wires (2406).

It should be understood that the second effective outer diameter ($d_4$) is defined at a region corresponding to the longitudinal mid-point of each wire (2406). Contact member (2400) may be positioned about transducer element (110) such that this region of contact is positioned at a location corresponding to a node associated with resonant ultrasonic vibrations communicated through acoustic assembly (100). In some versions, wires (2406) are configured to have inwardly projecting features that further localize the contact with outer diameter surface (118) at a location corresponding to a node associated with resonant ultrasonic vibrations communicated through acoustic assembly (100) when contact member (2400) reaches the second state. In some versions where acoustic assembly (100) is rotatable relative to handle assembly (20) about the longitudinal axis defined by waveguide (150), contact member (2400) rotates with acoustic assembly (100). In some other versions where acoustic assembly (100) is rotatable relative to handle assembly (20) about the longitudinal axis defined by waveguide (150), acoustic assembly (100) further rotates relative to contact member (2400), which remains rotationally fixed relative to handle assembly (20). Still other suitable variations of contact member (2400) will be apparent to those of ordinary skill in the art in view of the teachings herein.

C. Exemplary Transducer with Annular Conductive Groove

Figure 60:
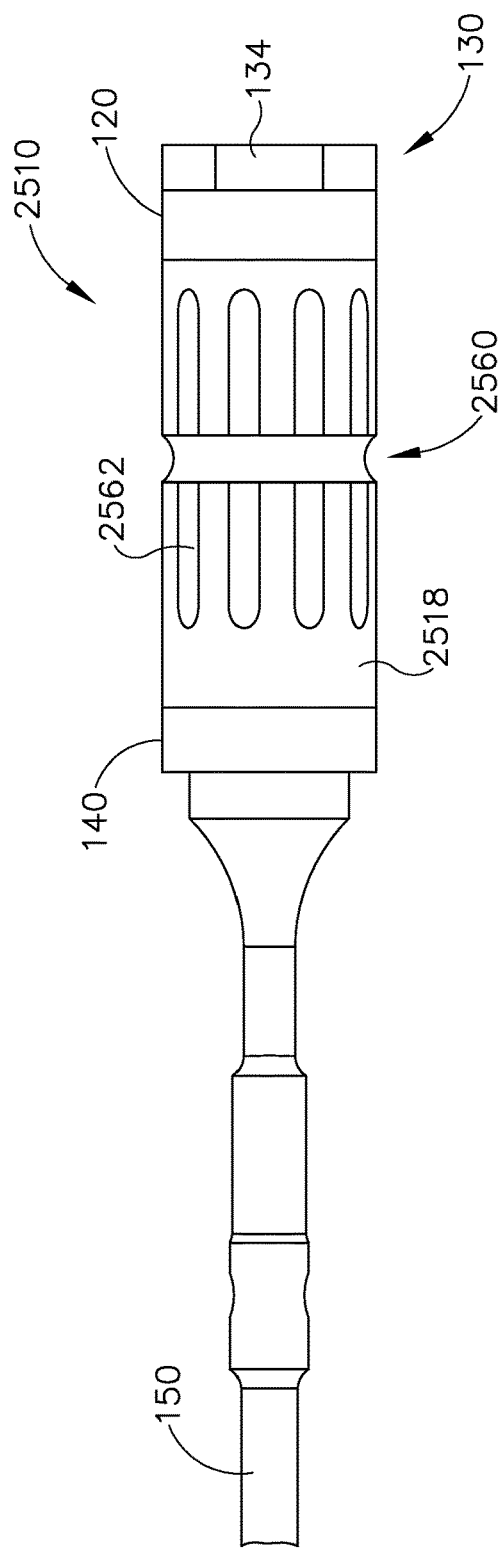
FIG. 60 depicts a partial side elevational view of another exemplary acoustic assembly, with an annular groove formed in the transducer element and conductive fingers extending from the annular groove.

FIG. 60 shows an exemplary alternative transducer element (2510). Transducer element (2510) of this example is identical to transducer element (110) described above, except that transducer element (2510) of this example includes an annular recess (2560) and an array of electrode fingers (2562) extending distally and proximally from annular recess (2560). It should be understood that transducer element (2510) may be readily substituted for any transducer element (110) referred to herein. Annular recess (2560) is located at a position along the length of transducer element (2510) corresponding to a node associated with resonant ultrasonic vibrations communicated through acoustic assembly (100). In some versions, annular recess (2560) is sputter coated with a conductive material (e.g., BeCu, silver, etc.), with the same sputter coating being used to form electrode fingers (2562). In some such versions, the sputter coating is thicker in annular recess (2560) than it is at fingers (2562). Of course, sputter coating is just one merely illustrative example. Any other suitable process(es) may be used. Fingers (2562) may assist in distributing electrical communication from recess (2560) along the length of outer diameter surface (2518). While fingers (2562) of the present example extend longitudinally, it should be understood that fingers (2562) may have any other suitable configuration and orientation. It should also be understood that fingers (2562) are merely optional, such that fingers (2562) may be omitted if desired.

Figure 61:
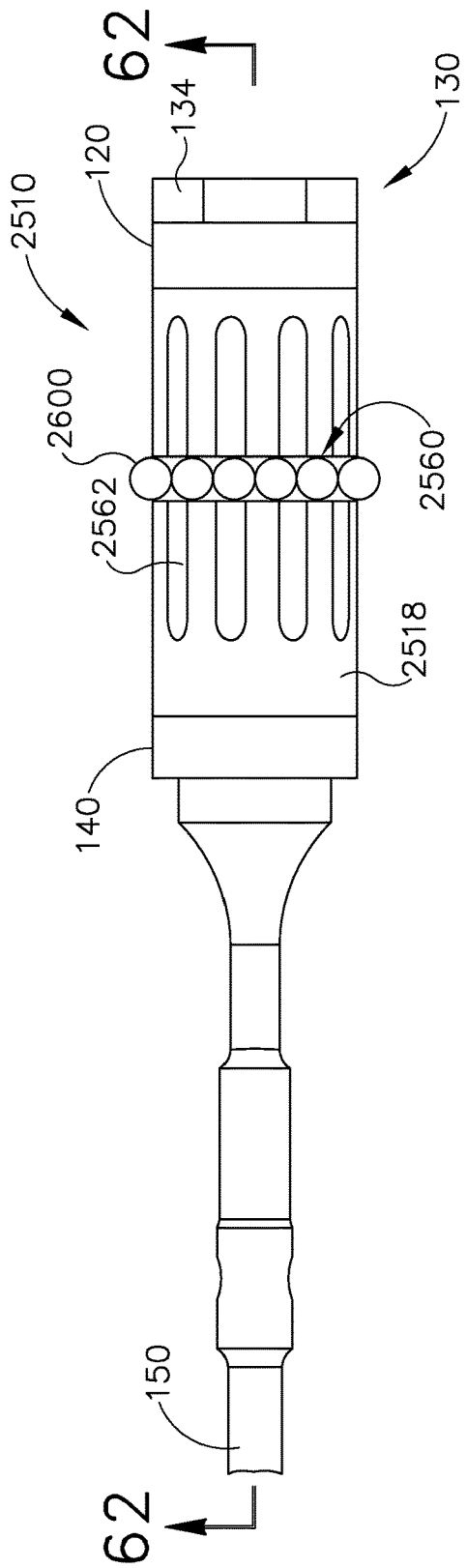
FIG. 61 depicts a partial side elevational view of the acoustic assembly of FIG. 60, with a set of bearings disposed in the groove.
Figure 62:
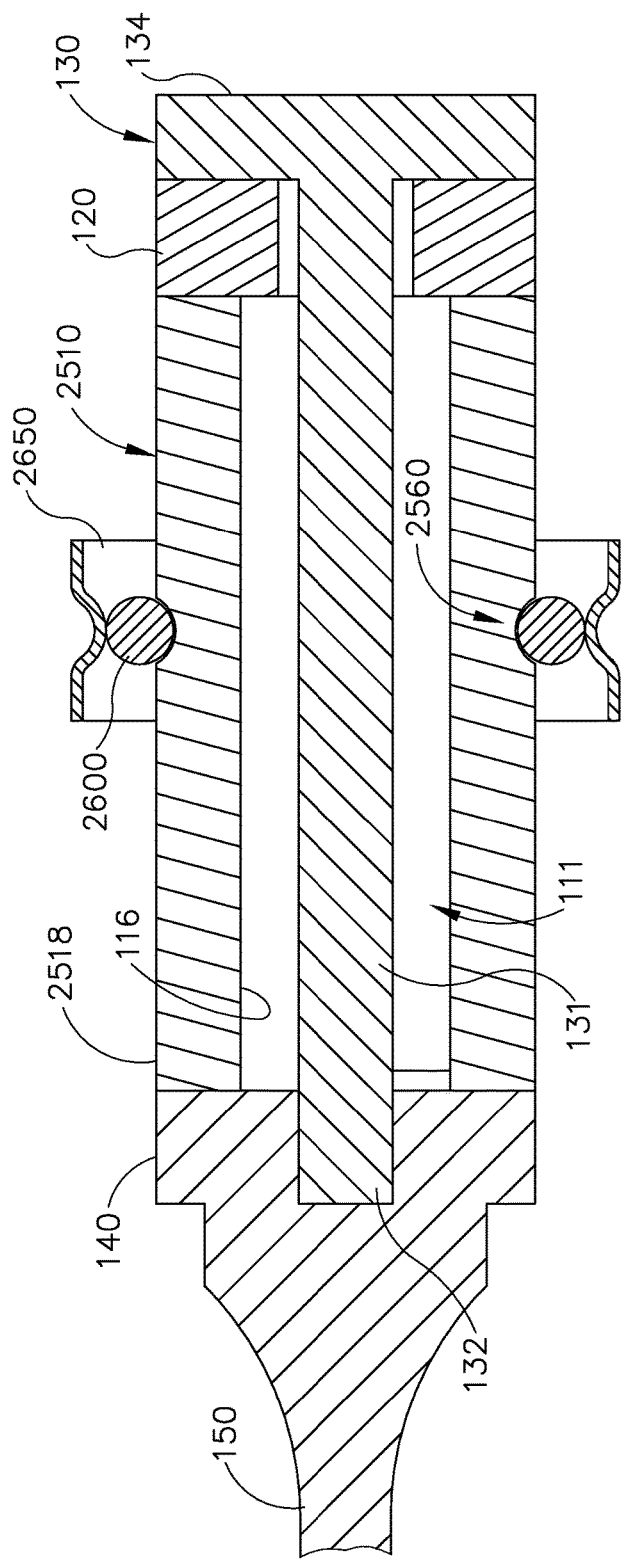
FIG. 62 depicts a cross-sectional side view of the acoustic assembly of FIG. 61, with an outer conductor disposed about the bearings.

FIGS. 61-62 show an exemplary set of conductive ball bearings (2600) disposed in recess (2560), such that recess (2560) serves as a race. An annular conductive member (2650) is disposed about ball bearings (2600). As shown in FIG. 62, a conductive member (2650) is fixedly secured in shroud housing (52) and resiliently bears inwardly against ball bearings (2600). By way of example only, conductive member (2650) may be separately formed and then snapped into (or otherwise secured to) shroud housing (52), may be molded in as an integral feature of shroud housing (52), may be formed by exposed traces of a flex circuit that is located in shroud housing (52), or may be otherwise formed. Conductive member (2650) is electrically coupled with generator (14) (or some other power source) using any suitable component(s). Since bearings (2600) and conductive member (2650) are electrically conductive, bearings (2600) and conductive member (2650) cooperate to provide a path for electrical continuity between outer diameter surface (2518) and generator (14) (or some other power source). It should also be understood that bearings (2600) may facilitate rotation of transducer element (2560) (along with other components of acoustic assembly (100)) about the longitudinal axis defined by waveguide (150) relative to handle assembly (20). Transducer element (2560) may thus be rotated while still maintaining electrical continuity with generator (14) (or some other power source).

Figure 63:
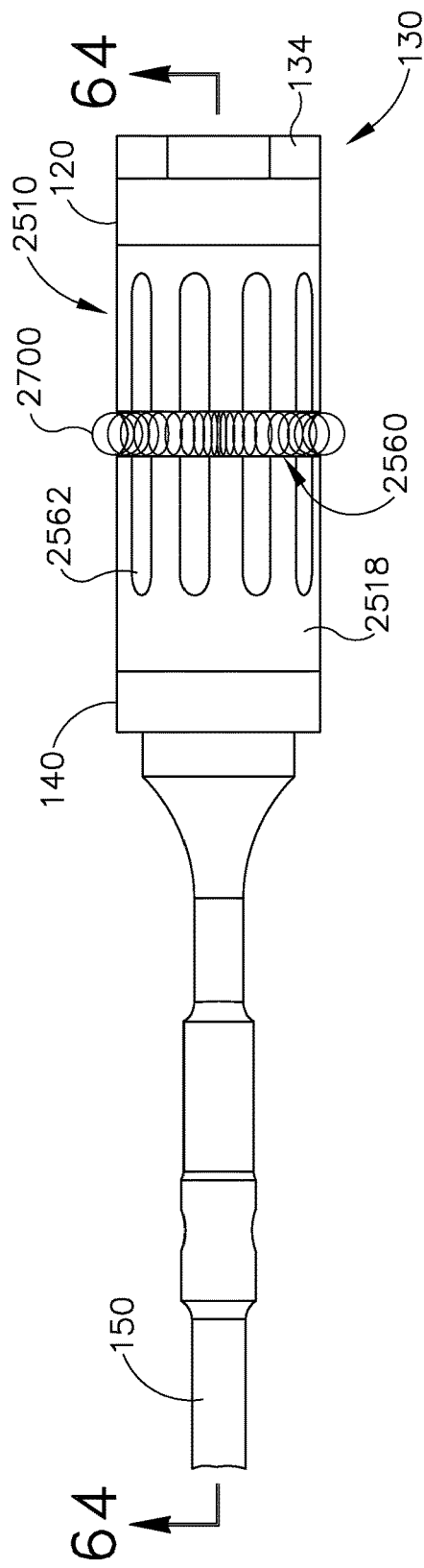
FIG. 63 depicts a partial side elevational view of the acoustic assembly of FIG. 60, with a coil spring disposed in the groove.
Figure 64:
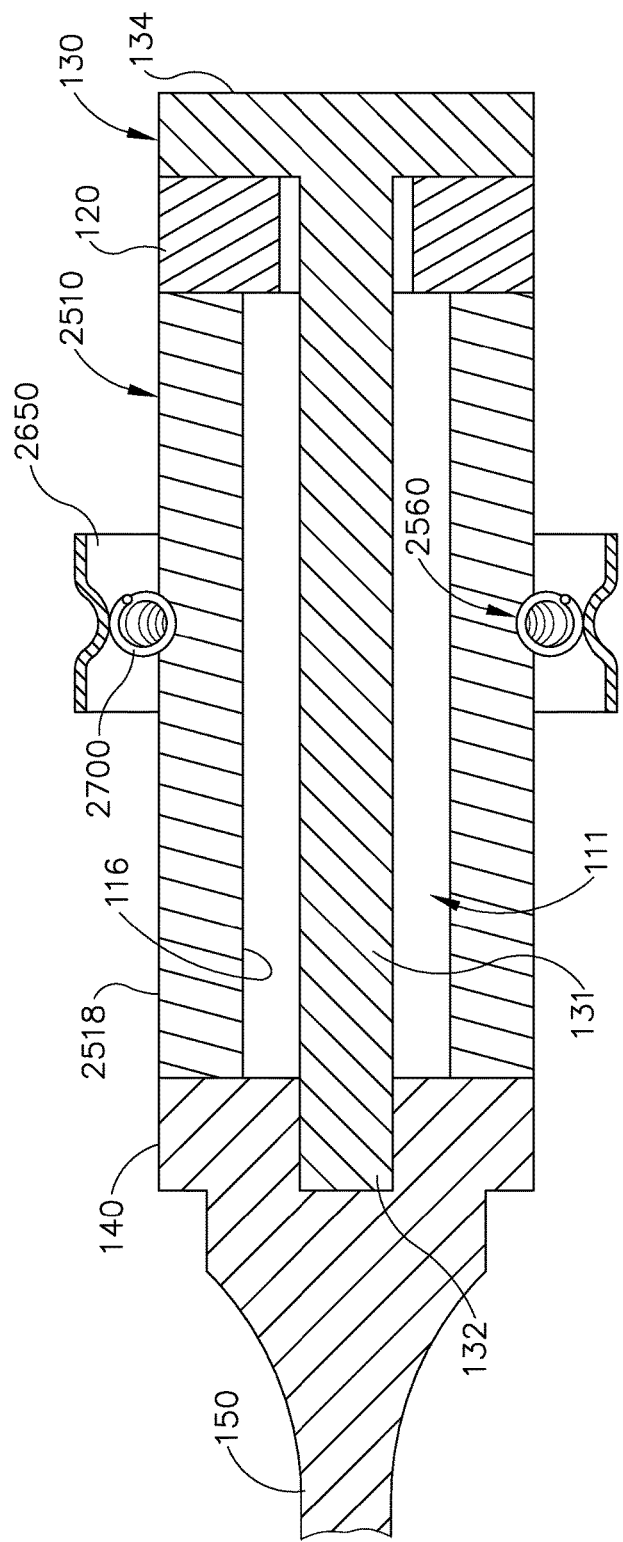
FIG. 64 depicts a cross-sectional side view of the acoustic assembly of FIG. 63, with an outer conductor disposed about the coil spring.

FIGS. 63-64 show an exemplary continuous coil spring (2700) disposed in recess (2560). Coil spring (2700) comprises an electrically conductive material and is formed in an annular shape. The effective inner diameter of coil spring (2700) is less than the outer diameter of transducer element (2510). In some versions coil spring (2700) is resiliently biased to assume shape having an effective inner diameter that is less than the outer diameter of recess (2560), such that coil spring (2700) fits snugly in recess (2560). Various suitable materials and processes that may be used to form coil spring (2700) will be apparent to those of ordinary skill in the art in view of the teachings herein. As shown in FIG. 64, conductive member (2650) is disposed about coil spring (2700). As noted above, conductive member (2650) is electrically coupled with generator (14) (or some other power source) using any suitable component(s). Since coil spring (2700) and conductive member (2650) are electrically conductive, coil spring (2700) and conductive member (2650) cooperate to provide a path for electrical continuity between outer diameter surface (118) and generator (14) (or some other power source). It should also be understood that coil spring (2700) may permit rotation of transducer element (2560) (along with other components of acoustic assembly (100)) about the longitudinal axis defined by waveguide (150) relative to handle assembly (20). Transducer element (2560) may this be rotated while still maintaining electrical continuity with generator (14) (or some other power source).

Figure 65:
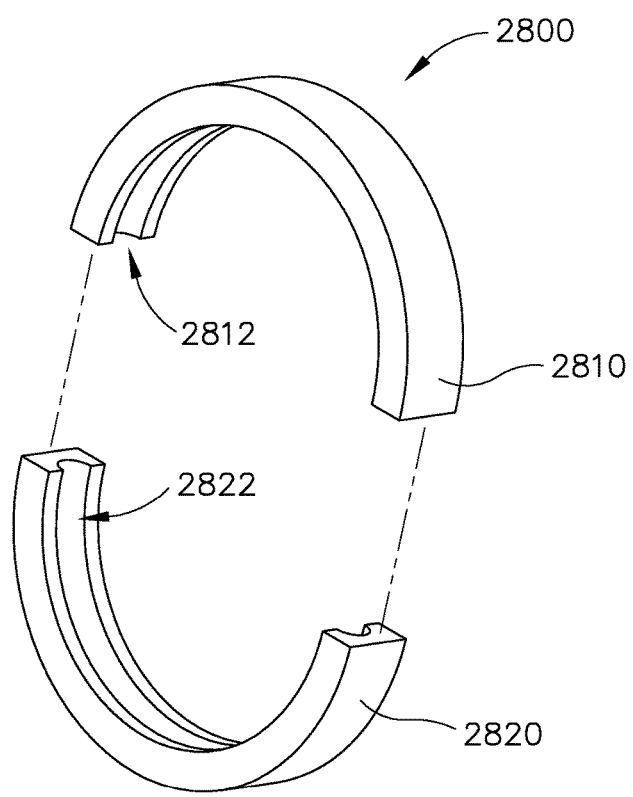
FIG. 65 depicts an exploded perspective view of an exemplary outer conductor assembly.
Figure 66:
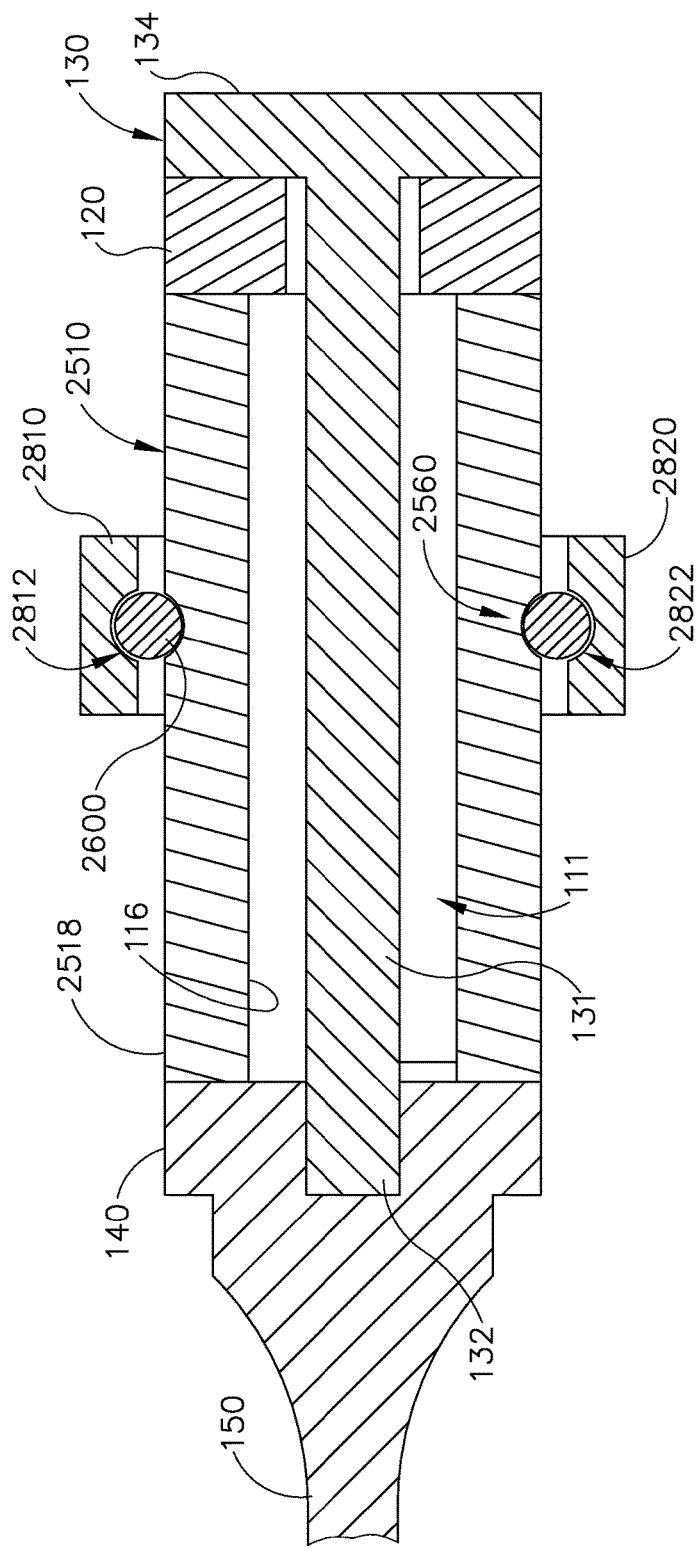
FIG. 66 depicts a cross-sectional side view of the acoustic assembly of FIG. 61 with the outer conductor assembly of FIG. 65 disposed about the bearings.

FIGS. 65-66 show an exemplary race assembly (2800) that may be used as a substitute for conductive member (2650). While race assembly (2800) is shown in FIG. 66 as being combined with bearings (2600), it should be understood that race assembly (2800) may also be combined with coil spring (2700) or other structures disposed in recess (2560). Race assembly (2800) comprises a first portion (2810) and a second portion (2820). Each portion (2810, 2820) defines a respective semi-annular recess (2812, 2822). Portions (2810, 2820) are configured to fit together to define an annular shape, with recesses (2812, 2822) also aligning with each other to define an annular shape. Portions (2810, 2820) are configured to be secured within shroud housing (52) after portions (2810, 2820) are positioned about bearings (2600). In this configuration, bearings (2600) are interposed between recesses (2812, 2822) and recess (2560). Race assembly (2800) may be coupled with shroud housing (52) through a snap fitting or any other suitable relationship. In some instances, race assembly (2800) includes one or more leaf springs to resiliently bias race assembly (2800) against bearings (2600).

Race assembly (2800) is electrically conductive and is electrically coupled with generator (14) (or some other power source) using any suitable component(s). Bearings (2600) and race assembly (2800) thus cooperate to provide a path for electrical continuity between outer diameter surface (2518) and generator (14) (or some other power source). Other variations of race assembly (2800) will be apparent to those of ordinary skill in the art in view of the teachings herein.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a shaft assembly;
   (b) an ultrasonic blade disposed at a distal end of the shaft assembly; and
   (c) an acoustic assembly, comprising:
      (i) an acoustic waveguide coupled with the blade,
      (ii) a piezoelectric transducer element, wherein the piezoelectric transducer element defines an inner diameter surface and an outer diameter surface that surrounds the inner diameter surface,
      (iii) a fastener configured to secure the piezoelectric transducer element relative to the acoustic waveguide, and
      (iv) a coupling member positioned in contact with the inner diameter surface of the piezoelectric transducer element, wherein the coupling member is configured to provide electrical continuity between the fastener and the inner diameter surface.

2. The apparatus of claim 1, wherein the piezoelectric transducer element has an elongate cylindraceous shape.

3. The apparatus of claim 1, wherein at least a portion of the inner diameter surface of the piezoelectric transducer element comprises an electrically conductive coating.

4. The apparatus of claim 1, further comprising a cap secured to the fastener, wherein the cap is in electrical communication with a power source, wherein the cap is configured to provide electrical continuity between the fastener and the power source.

5. The apparatus of claim 4, wherein the fastener is rotatable relative to the cap.

6. The apparatus of claim 1, wherein the coupling member is resiliently biased to bear against the inner diameter surface of the piezoelectric transducer element.

7. The apparatus of claim 6, wherein the coupling member comprises a first set of arms and a second set of arms, wherein the first set of arms resiliently bear against the inner diameter surface of the piezoelectric transducer element, wherein the second set of arms resiliently bear against the fastener.

8. The apparatus of claim 6, wherein the coupling member comprises a hub member and a set of arms extending from the hub member, wherein the hub member is secured to the fastener, wherein the arms are resiliently biased outwardly to bear against the inner diameter surface of the piezoelectric transducer element.

9. The apparatus of claim 8, wherein the arms extend proximally from the hub member at respective living hinges.

10. The apparatus of claim 8, wherein the arms are resiliently biased to assume a flat shape where the arms extend along a common plane with the hub member.

11. The apparatus of claim 6, wherein the coupling member comprises a rolled sheet resiliently biased to unroll against the inner diameter surface of the piezoelectric transducer element.

12. The apparatus of claim 6, wherein the coupling member comprises a coil spring.

13. The apparatus of claim 12, wherein the coil spring extends along a longitudinal axis defined by the piezoelectric transducer element and is extendable along the longitudinal axis defined by the piezoelectric transducer element.

14. The apparatus of claim 1, wherein the fastener is operable to deform the coupling member into engagement with the inner diameter surface of the piezoelectric transducer element.

15. The apparatus of claim 14, wherein the coupling member includes a buckling feature configured to buckle outwardly in response to longitudinal compression exerted on the coupling member by the fastener.

16. The apparatus of claim 1, wherein the coupling member comprises a filler material filling a gap defined between the fastener and the inner diameter surface of the piezoelectric transducer element.

17. The apparatus of claim 1, wherein the fastener comprises a bolt.

18. An apparatus for operating on tissue, the apparatus comprising:
   (a) a body;
   (b) a shaft assembly extending distally from the body;
   (c) an ultrasonic blade disposed at a distal end of the shaft assembly; and
   (d) an acoustic assembly, comprising:
      (i) an acoustic waveguide coupled with the blade,
      (ii) a piezoelectric transducer element, wherein the piezoelectric transducer element defines an inner diameter surface and an outer diameter surface opposed therefrom, wherein the outer diameter surface includes an annular recess formed in the outer diameter surface and extending circumferentially about a longitudinal axis of the piezoelectrical transducer element,
      (iii) a fastener configured to secure the piezoelectric transducer element relative to the acoustic waveguide, and
      (iv) a coupling member positioned in contact with the annular recess of the piezoelectric transducer element, wherein the coupling member extends circumferentially about the longitudinal axis and is configured to provide electrical continuity between the annular recess and a power source while permitting the piezoelectric transducer element to rotate relative to the body.

19. The apparatus of claim 18, wherein the acoustic assembly further comprises an end mass coupled to an end of the piezoelectric transducer element.

20. An apparatus for operating on tissue, the apparatus comprising:
   (a) a shaft assembly;
   (b) an ultrasonic blade disposed at a distal end of the shaft assembly; and
   (c) an acoustic assembly, comprising:
      (i) an acoustic waveguide coupled with the blade,
      (ii) a piezoelectric transducer element, wherein the piezoelectric transducer element defines an inner diameter surface and an outer diameter surface opposed therefrom,
      (iii) a fastener configured to secure the piezoelectric transducer element relative to the acoustic waveguide, and
      (iv) a coupling member configured to provide electrical continuity between the fastener and the inner diameter surface of the piezoelectric transducer element,
   wherein the piezoelectric transducer element, the fastener, and the coupling member are arranged concentrically.

* * * * *